United States Patent
Lau et al.

(10) Patent No.: US 9,732,137 B2
(45) Date of Patent: Aug. 15, 2017

(54) SEMI-RECOMBINANT PREPARATION OF GLP-1 ANALOGUES

(75) Inventors: Jesper Færgeman Lau, Farum (DK); Asser Sloth Andersen, Herlev (DK); Paw Bloch, Jyllinge (DK); Jesper Lau, Farum (DK); Patrick William Garibay, Holte (DK); Thomas Kruse, Herlev (DK); Inga Sig Nielsen Nørby, Birkerød (DK); Claus Ulrich Jessen, Slangerup (DK); Caspar Christensen, Brønshøj (DK); Jens Christian Norrild, Birkerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 201 days.

(21) Appl. No.: 12/810,934

(22) PCT Filed: Dec. 22, 2008

(86) PCT No.: PCT/EP2008/068211
§ 371 (c)(1),
(2), (4) Date: Aug. 31, 2010

(87) PCT Pub. No.: WO2009/083549
PCT Pub. Date: Jul. 9, 2009

(65) Prior Publication Data
US 2010/0317057 A1      Dec. 16, 2010

Related U.S. Application Data

(60) Provisional application No. 61/018,559, filed on Jan. 2, 2008.

(30) Foreign Application Priority Data

Dec. 28, 2007   (EP) .................................... 07124141

(51) Int. Cl.

| | |
|---|---|
| C07K 14/605 | (2006.01) |
| C07K 1/107 | (2006.01) |
| C07K 1/02 | (2006.01) |
| C07K 1/06 | (2006.01) |
| C07K 1/36 | (2006.01) |
| C07K 1/00 | (2006.01) |

(52) U.S. Cl.
CPC ............ *C07K 14/605* (2013.01); *C07K 1/006* (2013.01); *C07K 1/02* (2013.01); *C07K 1/061* (2013.01); *C07K 1/107* (2013.01); *C07K 1/1077* (2013.01)

(58) Field of Classification Search
None
See application file for complete search history.

(56) References Cited

U.S. PATENT DOCUMENTS

| | | |
|---|---|---|
| 6,277,819 B1 | 8/2001 | Efendic |
| 2001/0011071 A1 | 8/2001 | Knudsen et al. |
| 2003/0144471 A1* | 7/2003 | Jonassen et al. ............. 530/300 |
| 2004/0198654 A1* | 10/2004 | Glaesner et al. ............... 514/12 |
| 2006/0160740 A1* | 7/2006 | Efendic .................. A61K 38/26 514/7.2 |
| 2008/0004429 A1* | 1/2008 | Roberts et al. ............... 530/330 |

FOREIGN PATENT DOCUMENTS

| | | |
|---|---|---|
| EP | 733644 A1 | 9/1996 |
| EP | 869135 A1 | 10/1998 |
| JP | 2005503141 A | 2/2005 |
| JP | 2005504527 A | 2/2005 |
| WO | WO 98/08871 | 3/1998 |
| WO | WO 2005/027978 | 3/2005 |
| WO | WO 2005/058958 | 6/2005 |
| WO | WO 2006/005667 | 1/2006 |
| WO | WO 2006/037810 | * 4/2006 |
| WO | WO 2006/097536 | 9/2006 |
| WO | WO 2006/097537 | 9/2006 |
| WO | WO 2006/097538 | 9/2006 |
| WO | 2007/113205 A1 | 10/2007 |
| WO | 2007147816 A1 | 12/2007 |

OTHER PUBLICATIONS

Montalbetti et al., Tetrahedron, 2005, vol. 61:10827-10852.*
Margolin et al., J. Am. Chem. Soc., 1987, vol. 109(25):7885-7887.*
Hodgson D R W et al., "The Synthesis of Peptides and Proteins Containing Non-Natural Amino Acids," Chemical Reviews, 2004, vol. 33, No. 7, pp. 422-430.
Makino Tomohiro et al., "Semisynthesis of Human Ghrelin: Condensation of a BOC-Protected Recombinant Peptide With a Synthetic O-Acylated Fragment," Biopolymers, 2005, vol. 79, No. 5, pp. 238-247.
Okada Y, "Synthesis of Peptides by Solution Methods," Current Organic Chemistry, 2001, vol. 5, No. 1, pp. 1-43.
Wallace C J A, "Peptide Ligation and Semisynthesis," Current Opinion in Biotechnology, 1995, vol. 6, No. 4, pp. 403-410.
Gabor et al. "The first semi-synthetic serine protease made by native chemical ligation." Protein Expression and Purification. 2003. vol. 29. pp. 185-192.
Weng C. Chan et al.Fmoc Solid Phase Peptide Synthesis: A Practical Approach,Oxford University Press, 2000, pp. 41-74.

* cited by examiner

*Primary Examiner* — Xiaozhen Xie
(74) *Attorney, Agent, or Firm* — Rosemarie R. Wilk-Orescan

(57) ABSTRACT

A semi-recombinant method for the production of GLP-1 analogues and derivatives with non-proteogenic amino acids in the N-terminal part combining the use of recombinant expression techniques and chemical peptide synthesis.

11 Claims, 15 Drawing Sheets a)
```
                NcoI
                ~~~~~~~
        GlyThrSerMet AlaLysArg ThrPheThr SerAspValSer SerTyrLeu GluGlyGln
     1  GGTACCTCCA TGGCTAAAAG AACTTTTACT TCTGATGTTT CTTCTTATTT GGAAGGTCAA
        CCATGGAGGT ACCGATTTTC TTGAAAATGA AGACTACAAA GAAGAATAAA CCTTCCAGTT
                                                              XbaI
                                                              ~~~~~~~
        AlaAlaLysGlu PheIleAla TrpLeuVal ArgGlyArgGly ***
    61  GCTGCTAAAG AATTTATTGC TTGGTTGGTT AGAGGTAGAG GTTAGATCTA GAGATCAT
        CGACGATTTC TTAAATAACG AACCAACCAA TCTCCATCTC CAATCTAGAT CTCTAGTA
``` b)
```
                NcoI
                ~~~~~~~
        GlyThrSerMet AlaLysArg GluGluAla GluLysAlaGlu GlyThrPhe ThrSerAsp
     1  GGTACCTCCA TGGCTAAAAG AGAAGAAGCT GAAAAGGCTG AAGGTACTTT TACTTCTGAT
        CCATGGAGGT ACCGATTTTC TCTTCTTCGA CTTTTCCGAC TTCCATGAAA ATGAAGACTA

ValSerSerTyr LeuGluGlu GlnAlaAla ArgGluPheIle AlaTrpLeu ValArgGly
    61  GTTTCTTCTT ATTTGGAAGA ACAAGCTGCT AGAGAATTTA TTGCTTGGTT GGTTAGAGGT
        CAAAGAAGAA TAAACCTTCT TGTTCGACGA TCTCTTAAAT AACGAACCAA CCAATCTCCA
                         XbaI
                         ~~~~~~~
        ArgGlyLysGlu AlaGlu***
   121  AGAGGTAAAG AAGCTGAATA GAATCTAGAG ATCAT
        TCTCCATTTC TTCGACTTAT CTTAGATCTC TAGTA
``` c)
```
                NcoI
                ~~~~~~~
        GlyThrSerMet AlaLysArg GluGluAla GluLysAlaGlu GlyThrPhe ThrSerAsp
     1  GGTACCTCCA TGGCTAAAAG AGAAGAAGCT GAAAAGGCTG AAGGTACTTT TACTTCTGAT
        CCATGGAGGT ACCGATTTTC TCTTCTTCGA CTTTTCCGAC TTCCATGAAA ATGAAGACTA

ValSerSerTyr LeuGluGlu GlnAlaAla ArgGluPheIle AlaTrpLeu ValArgGly
    61  GTTTCTTCTT ATTTGGAAGA ACAAGCTGCT AGAGAATTTA TTGCTTGGTT GGTTAGAGGT
        CAAAGAAGAA TAAACCTTCT TGTTCGACGA TCTCTTAAAT AACGAACCAA CCAATCTCCA
                         XbaI
                         ~~~~~~~
        ArgLysGluAla Glu***
   121  AGAAAAGAAG CTGAATAGAA TCTAGAGATC AT
        TCTTTTCTTC GACTTATCTT AGATCTCTAG TA
```

```
             NcoI
          ~~~~~~~
   GlyValSerMet AlaLysArg GluGlyThr PheThrSerAsp ValSerSer TyrLeuGlu
 1 GGGGTATCCA TGGCTAAGAG AGAAGGTACC TTCACCTCTG ACGTCTCGAG TTACTTGGAA
   CCCCATAGGT ACCGATTCTC TCTTCCATGG AAGTGGAGAC TGCAGAGCTC AATGAACCTT

GlyGlnAlaAla LysGluPhe IleAlaTrp LeuValArgGly ArgGly***
61 GGCCAAGCTG CTAAGGAGTT CATCGCTTGG TTGGTTAGAG GCCGCGGTTA GACGCAGCCC
   CCGGTTCGAC GATTCCTCAA GTAGCGAACC AACCAATCTC CGGCGCCAAT CTGCGTCGGG
           XbaI
        ~~~~~~~
121 GCAGGCTCTA GAAACTAA
    CGTCCGAGAT CTTTGATT
```

Fig. 2  d)

KR)
```
              NcoI
           ~~~~~~~
    GlyValSerMet AlaLysArg ThrPheThr SerAspValSer SerTyrLeu GluGlyGln
235 GGGGTATCCA TGGCTAAAAG AACTTTTACT TCTGATGTTT CTTCTTATTT GGAAGGTCAA
    CCCCATAGGT ACCGATTTTC TTGAAAATGA AGACTACAAA GAAGAATAAA CCTTCCAGTT
                                                           XbaI
                                                        ~~~~~~~
    AlaAlaLysGlu PheIleAla TrpLeuVal ArgGlyArgGly ***
295 GCTGCTAAAG AATTTATTGC TTGGTTGGTT AGAGGTAGAG GTTAGATCTA GA
    CGACGATTTC TTAAATAACG AACCAACCAA TCTCCATCTC CAATCTAGAT CT
```

Fig. 3

A)
```
                  NcoI
                  ~~~~~~~
    GlyValSerMet AlaArgAla ArgTyrLys ArgThrPheThr SerAspVal SerSerTyr
235 GGGGTATCCA TGGCTAGAGC TAGATATAAA AGAACTTTTA CTTCTGATGT TTCTTCTTAT
    CCCCATAGGT ACCGATCTCG ATCTATATTT TCTTGAAAAT GAAGACTACA AAGAAGAATA
                                                                XbaI
                                                                ~~
    LeuGluGlyGln AlaAlaLys GluPheIle AlaTrpLeuVal ArgGlyArg Gly***
295 TTGGAAGGTC AAGCTGCTAA AGAATTTATT GCTTGGTTGG TTAGAGGTAG AGGTTAGATC
    AACCTTCCAG TTCGACGATT TCTTAAATAA CGAACCAACC AATCTCCATC TCCAATCTAG
    XbaI
    ~~~~
355 TAGAAAC
    ATCTTTG
```

B)
```
                  NcoI
                  ~~~~~~~
    GlyValSerMet AlaArgAsp LeuGlyLys ArgThrPheThr SerAspVal SerSerTyr
235 GGGGTATCCA TGGCTAGAGA TTTGGGTAAA AGAACTTTTA CTTCTGATGT TTCTTCTTAT
    CCCCATAGGT ACCGATCTCT AAACCCATTT TCTTGAAAAT GAAGACTACA AAGAAGAATA
                                                                XbaI
                                                                ~~
    LeuGluGlyGln AlaAlaLys GluPheIle AlaTrpLeuVal ArgGlyArg Gly***
295 TTGGAAGGTC AAGCTGCTAA AGAATTTATT GCTTGGTTGG TTAGAGGTAG AGGTTAGATC
    AACCTTCCAG TTCGACGATT TCTTAAATAA CGAACCAACC AATCTCCATC TCCAATCTAG
    XbaI
    ~~~~
355 TAGAAAC
    ATCTTTG
```

C)
```
                  NcoI
                  ~~~~~~~
    GlyValSerMet AlaArgAsp LeuAlaLys ArgThrPheThr SerAspVal SerSerTyr
235 GGGGTATCCA TGGCTAGAGA TTTGGCTAAA AGAACTTTTA CTTCTGATGT TTCTTCTTAT
    CCCCATAGGT ACCGATCTCT AAACCGATTT TCTTGAAAAT GAAGACTACA AAGAAGAATA
                                                                XbaI
                                                                ~~
    LeuGluGlyGln AlaAlaLys GluPheIle AlaTrpLeuVal ArgGlyArg Gly***
295 TTGGAAGGTC AAGCTGCTAA AGAATTTATT GCTTGGTTGG TTAGAGGTAG AGGTTAGATC
    AACCTTCCAG TTCGACGATT TCTTAAATAA CGAACCAACC AATCTCCATC TCCAATCTAG
    XbaI
    ~~~~
355 TAGAAAC
    ATCTTTG
```

Fig. 4 A)–C)

D)
```
              NcoI
              ~~~~~~~
     GlyValSerMet AlaArgAla ArgAlaLys ArgThrPheThr SerAspVal SerSerTyr
235  GGGGTATCCA TGGCTAGAGC TAGAGCTAAA AGAACTTTTA CTTCTGATGT TTCTTCTTAT
     CCCCATAGGT ACCGATCTCG ATCTCGATTT TCTTGAAAAT GAAGACTACA AAGAAGAATA
                                                                  XbaI
                                                                  ~~

LeuGluGlyGln AlaAlaLys GluPheIle AlaTrpLeuVal ArgGlyArg Gly***
295  TTGGAAGGTC AAGCTGCTAA AGAATTTATT GCTTGGTTGG TTAGAGGTAG AGGTTAGATC
     AACCTTCCAG TTCGACGATT TCTTAAATAA CGAACCAACC AATCTCCATC TCCAATCTAG
     XbaI
     ~~~~
355  TAGAAAC
     ATCTTTG
```

E)
```
              NcoI
              ~~~~~~~
     GlyValSerMet AlaArgAla LeuAspLys ArgThrPheThr SerAspVal SerSerTyr
235  GGGGTATCCA TGGCTAGAGC TTTGGATAAA AGAACTTTTA CTTCTGATGT TTCTTCTTAT
     CCCCATAGGT ACCGATCTCG AAACCTATTT TCTTGAAAAT GAAGACTACA AAGAAGAATA
                                                                  XbaI
                                                                  ~~

LeuGluGlyGln AlaAlaLys GluPheIle AlaTrpLeuVal ArgGlyArg Gly***
295  TTGGAAGGTC AAGCTGCTAA AGAATTTATT GCTTGGTTGG TTAGAGGTAG AGGTTAGATC
     AACCTTCCAG TTCGACGATT TCTTAAATAA CGAACCAACC AATCTCCATC TCCAATCTAG
     XbaI
     ~~~~
355  TAGAAAC
     ATCTTTG
```

F)
```
              NcoI
              ~~~~~~~
     GlyValSerMet AlaArgAla LeuAlaLys ArgThrPheThr SerAspVal SerSerTyr
235  GGGGTATCCA TGGCTAGAGC TTTGGCTAAA AGAACTTTTA CTTCTGATGT TTCTTCTTAT
     CCCCATAGGT ACCGATCTCG AAACCGATTT TCTTGAAAAT GAAGACTACA AAGAAGAATA
                                                                  XbaI
                                                                  ~~

LeuGluGlyGln AlaAlaLys GluPheIle AlaTrpLeuVal ArgGlyArg Gly***
295  TTGGAAGGTC AAGCTGCTAA AGAATTTATT GCTTGGTTGG TTAGAGGTAG AGGTTAGATC
     AACCTTCCAG TTCGACGATT TCTTAAATAA CGAACCAACC AATCTCCATC TCCAATCTAG
     XbaI
     ~~~~
355  TAGAAAC
     ATCTTTG
```

Fig. 4 D)–F)

G)
```
                NcoI
                ~~~~~~~
     GlyValSerMet AlaArgAsp LeuGlyLys ArgGluAlaThr PheThrSer AspValSer
235  GGGGTATCCA TGGCTAGAGA TTTGGGTAAA AGAGAAGCTA CTTTTACTTC TGATGTTTCT
     CCCCATAGGT ACCGATCTCT AAACCCATTT TCTCTTCGAT GAAAATGAAG ACTACAAAGA
     SerTyrLeuGlu GlyGlnAla AlaLysGlu PheIleAlaTrp LeuValArg GlyArgGly
295  TCTTATTTGG AAGGTCAAGC TGCTAAAGAA TTTATTGCTT GGTTGGTTAG AGGTAGAGGT
     AGAATAAACC TTCCAGTTCG ACGATTTCTT AAATAACGAA CCAACCAATC TCCATCTCCA
            XbaI
            ~~~~~~~
     ***
355  TAGAATCTAG AAAC
     ATCTTAGATC TTTG
```

H)
```
                NcoI
                ~~~~~~~
     GlyValSerMet AlaProArg AspLeuGly LysArgThrPhe ThrSerAsp ValSerSer
235  GGGGTATCCA TGGCTCCAAG AGATTTGGGT AAAAGAACTT TTACTTCTGA TGTTTCTTCT
     CCCCATAGGT ACCGAGGTTC TCTAAACCCA TTTTCTTGAA AATGAAGACT ACAAAGAAGA
     TyrLeuGluGly GlnAlaAla LysGluPhe IleAlaTrpLeu ValArgGly ArgGly***
295  TATTTGGAAG GTCAAGCTGC TAAAGAATTT ATTGCTTGGT TGGTTAGAGG TAGAGGTTAG
     ATAAACCTTC CAGTTCGACG ATTTCTTAAA TAACGAACCA ACCAATCTCC ATCTCCAATC
         XbaI
         ~~~~~~~
355  AATCTAGAAA C
     TTAGATCTTT G
```

I)
```
                NcoI
                ~~~~~~~
     GlyValSerMet AlaArgPro LeuGlyLys ArgThrPheThr SerAspVal SerSerTyr
235  GGGGTATCCA TGGCTAGACC ATTGGGTAAA AGAACTTTTA CTTCTGATGT TTCTTCTTAT
     CCCCATAGGT ACCGATCTGG TAACCCATTT TCTTGAAAAT GAAGACTACA AAGAAGAATA

XbaI

LeuGluGlyGln AlaAlaLys GluPheIle AlaTrpLeuVal ArgGlyArg Gly***
295  TTGGAAGGTC AAGCTGCTAA AGAATTTATT GCTTGGTTGG TTAGAGGTAG AGGTTAGAAT
     AACCTTCCAG TTCGACGATT TCTTAAATAA CGAACCAACC AATCTCCATC TCCAATCTTA
     XbaI
     ~~~~~
355  CTAGAAAC
     GATCTTTG
```

Fig. 4 G)–I)

J)
```
                NcoI
                ~~~~~~~
        GlyValSerMet AlaArgAsp LeuGlyLys ArgGluAlaGln ThrPheThr SerAspVal
    235 GGGGTATCCA TGGCTAGAGA TTTGGGTAAA AGAGAAGCTC AAACTTTTAC TTCTGATGTT
        CCCCATAGGT ACCGATCTCT AAACCCATTT TCTCTTCGAG TTTGAAAATG AAGACTACAA
        SerSerTyrLeu GluGlyGln AlaAlaLys GluPheIleAla TrpLeuVal ArgGlyArg
    295 TCTTCTTATT TGGAAGGTCA AGCTGCTAAA GAATTTATTG CTTGGTTGGT TAGAGGTAGA
        AGAAGAATAA ACCTTCCAGT TCGACGATTT CTTAAATAAC GAACCAACCA ATCTCCATCT
                   XbaI
                   ~~~~~~~
        Gly***
    355 GGTTAGAATC TAGAAAC
        CCAATCTTAG ATCTTTG
```

K)
```
                NcoI
                ~~~~~~~
        GlyValSerMet AlaArgAsp LeuGlyLys ArgGluAlaGlu AlaThrPhe ThrSerAsp
    235 GGGGTATCCA TGGCTAGAGA TTTGGGTAAA AGAGAAGCTG AAGCTACTTT TACTTCTGAT
        CCCCATAGGT ACCGATCTCT AAACCCATTT TCTCTTCGAC TTCGATGAAA ATGAAGACTA
        ValSerSerTyr LeuGluGly GlnAlaAla LysGluPheIle AlaTrpLeu ValArgGly
    295 GTTTCTTCTT ATTTGGAAGG TCAAGCTGCT AAAGAATTTA TTGCTTGGTT GGTTAGAGGT
        CAAAGAAGAA TAAACCTTCC AGTTCGACGA TTTCTTAAAT AACGAACCAA CCAATCTCCA
                   XbaI
                   ~~~~~~
    355 AGAGGTTAGA ATCTAGAAAC
        TCTCCAATCT TAGATCTTTG
```

K5)
```
                NcoI
                ~~~~~~~
        GlyValSerMet AlaArgAsp LeuGlyLys ArgGluAlaGlu LeuGluLys ArgThrPhe
    235 GGGGTATCCA TGGCTAGAGA TTTGGGTAAA AGAGAAGCTG AATTGGAAAA AAGAACTTTT
        CCCCATAGGT ACCGATCTCT AAACCCATTT TCTCTTCGAC TTAACCTTTT TTCTTGAAAA
        ThrSerAspVal SerSerTyr LeuGluGly GlnAlaAlaLys GluPheIle AlaTrpLeu
    295 ACTTCTGATG TTTCTTCTTA TTTGGAAGGT CAAGCTGCTA AAGAATTTAT TGCTTGGTTG
        TGAAGACTAC AAAGAAGAAT AAACCTTCCA GTTCGACGAT TCTTAAATA ACGAACCAAC
                             XbaI
                             ~~~~~~
        ValArgGlyArg Gly***
    355 GTTAGAGGTA GAGGTTAGAA TCTAGAAAC
        CAATCTCCAT CTCCAATCTT AGATCTTTG
```

NcoI
   ~~~~~~~

GlyValSerMet AlaArgAsp LeuGlyArg ArgGluAlaGlu LeuGluLys ArgThrPhe
235 GGGGTATCCA TGGCTAGAGA TTTGGGTAGA AGAGAAGCTG AATTGGAAAA AAGAACTTTT
   CCCCATAGGT ACCGATCTCT AAACCCATCT TCTCTTCGAC TTAACCTTTT TTCTTGAAAA
   ThrSerAspVal SerSerTyr LeuGluGly GlnAlaAlaLys GluPheIle AlaTrpLeu
295 ACTTCTGATG TTTCTTCTTA TTTGGAAGGT CAAGCTGCTA AGAATTTAT TGCTTGGTTG
   TGAAGACTAC AAAGAAGAAT AAACCTTCCA GTTCGACGAT TCTTAAATA ACGAACCAAC
            XbaI
            ~~~~~~

ValArgGlyArg Gly***
355 GTTAGAGGTA GAGGTTAGAA TCTAGAAAC
   CAATCTCCAT CTCCAATCTT AGATCTTTG

K7)

NcoI
   ~~~~~~~

GlyValSerMet AlaArgAsp LeuGlyGlu AlaGluLeuGlu LysArgThr PheThrSer
235 GGGGTATCCA TGGCTAGAGA TTTGGGTGAA GCTGAATTGG AAAAAAGAAC TTTTACTTCT
   CCCCATAGGT ACCGATCTCT AAACCCACTT CGACTTAACC TTTTTTCTTG AAAATGAAGA
   AspValSerSer TyrLeuGlu GlnGlnAla AlaLysGluPhe IleAlaTrp LeuValArg
295 GATGTTTCTT CTTATTTGGA AGGTCAAGCT GCTAAAGAAT TTATTGCTTG GTTGGTTAGA
   CTACAAAGAA GAATAAACCT TCCAGTTCGA CGATTTCTTA AATAACGAAC CAACCAATCT
        XbaI
        ~~~~~~~

GlyArgGly***
355 GGTAGAGGTT AGAATCTAGA AAC
   CCATCTCCAA TCTTAGATCT TTG

L)

NcoI
   ~~~~~~~

GlyValSerMet AlaArgAsp LeuGlyLys ArgGluAlaGlu AlaGlnThr PheThrSer
235 GGGGTATCCA TGGCTAGAGA TTTGGGTAAA AGAGAAGCTG AAGCTCAAAC TTTTACTTCT
   CCCCATAGGT ACCGATCTCT AAACCCATTT TCTCTTCGAC TTCGAGTTTG AAAATGAAGA
   AspValSerSer TyrLeuGlu GlyGlnAla AlaLysGluPhe IleAlaTrp LeuValArg
295 GATGTTTCTT CTTATTTGGA AGGTCAAGCT GCTAAAGAAT TTATTGCTTG GTTGGTTAGA
   CTACAAAGAA GAATAAACCT TCCAGTTCGA CGATTTCTTA AATAACGAAC CAACCAATCT
        XbaI
        ~~~~~~~

GlyArgGly***
355 GGTAGAGGTT AGAATCTAGA AAC
   CCATCTCCAA TCTTAGATCT TTG

Fig. 4 K6)–L)

L2)
```
            NcoI
        ~~~~~~~
    GlyValSerMet AlaArgAsp LeuGlyLys ArgGluAlaGlu AlaGlnLys ArgThrPhe
235 GGGGTATCCA TGGCTAGAGA TTTGGGTAAA AGAGAAGCTG AAGCTCAAAA AAGAACTTTT
    CCCCATAGGT ACCGATCTCT AAACCCATTT TCTCTTCGAC TTCGAGTTTT TTCTTGAAAA
    ThrSerAspVal SerSerTyr LeuGluGly GlnAlaAlaLys GluPheIle AlaTrpLeu
295 ACTTCTGATG TTTCTTCTTA TTTGGAAGGT CAAGCTGCTA AGAATTTAT TGCTTGGTTG
    TGAAGACTAC AAAGAAGAAT AAACCTTCCA GTTCGACGAT TCTTAAATA ACGAACCAAC
                                XbaI
                             ~~~~~~
    ValArgGlyArg Gly***
355 GTTAGAGGTA GAGGTTAGAA TCTAGAAAC
    CAATCTCCAT CTCCAATCTT AGATCTTTG
```

L3)
```
            NcoI
        ~~~~~~~
    GlyValSerMet AlaArgAsp LeuGlyArg ArgGluAlaGlu AlaGlnLys ArgThrPhe
235 GGGGTATCCA TGGCTAGAGA TTTGGGTAGA AGAGAAGCTG AAGCTCAAAA AAGAACTTTT
    CCCCATAGGT ACCGATCTCT AAACCCATCT TCTCTTCGAC TTCGAGTTTT TTCTTGAAAA
    ThrSerAspVal SerSerTyr LeuGluGly GlnAlaAlaLys GluPheIle AlaTrpLeu
295 ACTTCTGATG TTTCTTCTTA TTTGGAAGGT CAAGCTGCTA AGAATTTAT TGCTTGGTTG
    TGAAGACTAC AAAGAAGAAT AAACCTTCCA GTTCGACGAT TCTTAAATA ACGAACCAAC
                                XbaI
                             ~~~~~~
    ValArgGlyArg Gly***
355 GTTAGAGGTA GAGGTTAGAA TCTAGAAAC
    CAATCTCCAT CTCCAATCTT AGATCTTTG
```

L4)
```
            NcoI
        ~~~~~~~~
    GlyValSerMet AlaArgAsp LeuGlyGlu AlaGluAlaGln LysArgThr PheThrSer
235 GGGGTATCCA TGGCTAGAGA TTTGGGTGAA GCTGAAGCTC AAAAAAGAAC TTTTACTTCT
    CCCCATAGGT ACCGATCTCT AAACCCACTT CGACTTCGAG TTTTTTCTTG AAAATGAAGA
    AspValSerSer TyrLeuGlu GlyGlnAla AlaLysGluPhe IleAlaTrp LeuValArg
295 GATGTTTCTT CTTATTTGGA AGGTCAAGCT GCTAAAGAAT TTATTGCTTG GTTGGTTAGA
    CTACAAAGAA GAATAAACCT TCCAGTTCGA CGATTTCTTA AATAACGAAC CAACCAATCT
                    XbaI
                 ~~~~~~~
    GlyArgGly***
355 GGTAGAGGTT AGAATCTAGA AAC
    CCATCTCCAA TCTTAGATCT TTG
```

Fig. 4  L2)–L4)

M)
```
                NcoI
                ~~~~~~~
      GlyValSerMet AlaGluArg LeuGluArg AspLeuGlyLys ArgThrPhe ThrSerAsp
  235 GGGGTATCCA TGGCTGAAAG ATTGGAAAGA GATTTGGGTA AAAGAACTTT TACTTCTGAT
      CCCCATAGGT ACCGACTTTC TAACCTTTCT CTAAACCCAT TTTCTTGAAA ATGAAGACTA
      ValSerSerTyr LeuGluGly GlnAlaAla LysGluPheIle AlaTrpLeu ValArgGly
  295 GTTTCTTCTT ATTTGGAAGG TCAAGCTGCT AAAGAATTTA TTGCTTGGTT GGTTAGAGGT
      CAAAGAAGAA TAAACCTTCC AGTTCGACGA TTTCTTAAAT AACGAACCAA CCAATCTCCA
                     XbaI
                     ~~~~~~~
      ArgGly***
  355 AGAGGTTAGA ATCTAGAAAC
      TCTCCAATCT TAGATCTTTG
```

N)
```
                NcoI
                ~~~~~~~
      GlyValSerMet AlaLysGlu ArgLeuGlu ArgAspLeuGly LysArgThr PheThrSer
  235 GGGGTATCCA TGGCTAAAGA AAGATTGGAA AGAGATTTGG GTAAAAGAAC TTTTACTTCT
      CCCCATAGGT ACCGATTTCT TTCTAACCTT TCTCTAAACC CATTTTCTTG AAAATGAAGA
      AspValSerSer TyrLeuGlu GlyGlnAla AlaLysGluPhe IleAlaTrp LeuValArg
  295 GATGTTTCTT CTTATTTGGA AGGTCAAGCT GCTAAAGAAT TTATTGCTTG GTTGGTTAGA
      CTACAAAGAA GAATAAACCT TCCAGTTCGA CGATTTCTTA ATAACGAAC CAACCAATCT
                   XbaI
                   ~~~~~~~
      GlyArgGly***
  355 GGTAGAGGTT AGAATCTAGA AAC
      CCATCTCCAA TCTTAGATCT TTG
```

O)
```
                NcoI
                ~~~~~~~
      GlyValSerMet AlaGluArg LeuGluLys ArgThrPheThr SerAspVal SerSerTyr
  235 GGGGTATCCA TGGCTGAAAG ATTGGAAAAA AGAACTTTTA CTTCTGATGT TTCTTCTTAT
      CCCCATAGGT ACCGACTTTC TAACCTTTTT TCTTGAAAAT GAAGACTACA AGAAGAATA

XbaI
                                                                  ~
      LeuGluGlyGln AlaAlaLys GluPheIle AlaTrpLeuVal ArgGlyArg Gly***
  295 TTGGAAGGTC AAGCTGCTAA AGAATTTATT GCTTGGTTGG TTAGAGGTAG AGGTTAGAAT
      AACCTTCCAG TTCGACGATT TCTTAAATAA CGAACCAACC AATCTCCATC TCCAATCTTA
      XbaI
      ~~~~~
  355 CTAGAAAC
      GATCTTTG
```

Fig. 4 M)–O)

P)
```
                NcoI
                ~~~~~~~
        GlyValSerMet AlaLysGlu ArgLeuGlu LysArgThrPhe ThrSerAsp ValSerSer
    235 GGGGTATCCA TGGCTAAAGA AAGATTGGAA AAAAGAACTT TTACTTCTGA TGTTTCTTCT
        CCCCATAGGT ACCGATTTCT TTCTAACCTT TTTTCTTGAA AATGAAGACT ACAAAGAAGA
        TyrLeuGluGly GlnAlaAla LysGluPhe IleAlaTrpLeu ValArgGly ArgGly***
    295 TATTTGGAAG GTCAAGCTGC TAAAGAATTT ATTGCTTGGT TGGTTAGAGG TAGAGGTTAG
        ATAAACCTTC CAGTTCGACG ATTTCTTAAA TAACGAACCA ACCAATCTCC ATCTCCAATC
           XbaI
           ~~~~~~
    355 AATCTAGAAA C
        TTAGATCTTT G
```

Q)
```
                NcoI
                ~~~~~~~
        GlyValSerMet AlaProGlu ArgLeuGlu ArgAspLeuGly LysArgThr PheThrSer
   .235 GGGGTATCCA TGGCTCCAGA AAGATTGGAA AGAGATTTGG GTAAAAGAAC TTTTACTTCT
        CCCCATAGGT ACCGAGGTCT TTCTAACCTT TCTCTAAACC CATTTTCTTG AAAATGAAGA
        AspValSerSer TyrLeuGlu GlyGlnAla AlaLysGluPhe IleAlaTrp LeuValArg
    295 GATGTTTCTT CTTATTTGGA AGGTCAAGCT GCTAAAGAAT TTATTGCTTG GTTGGTTAGA
        CTACAAAGAA GAATAAACCT TCCAGTTCGA CGATTTCTTA AATAACGAAC CAACCAATCT
                       XbaI
                       ~~~~~~~
        GlyArgGly***
    355 GGTAGAGGTT AGAATCTAGA AAC
        CCATCTCCAA TCTTAGATCT TTG
```

R)
```
                NcoI
                ~~~~~~~
        GlyValSerMet AlaProGlu ArgLeuGlu LysArgThrPhe ThrSerAsp ValSerSer
    235 GGGGTATCCA TGGCTCCAGA AAGATTGGAA AAAAGAACTT TTACTTCTGA TGTTTCTTCT
        CCCCATAGGT ACCGAGGTCT TTCTAACCTT TTTTCTTGAA AATGAAGACT ACAAAGAAGA
        TyrLeuGluGly GlnAlaAla LysGluPhe IleAlaTrpLeu ValArgGly ArgGly***
    295 TATTTGGAAG GTCAAGCTGC TAAAGAATTT ATTGCTTGGT TGGTTAGAGG TAGAGGTTAG
        ATAAACCTTC CAGTTCGACG ATTTCTTAAA TAACGAACCA ACCAATCTCC ATCTCCAATC
           XbaI
           ~~~~~~
    355 AATCTAGAAA C
        TTAGATCTTT G
```

```
            NcoI
         ~~~~~~~
     GlyValSerMet AlaGluAla GluAlaArg AspLeuGlyLys ArgThrPhe ThrSerAsp
235  GGGGTATCCA TGGCTGAAGC TGAAGCTAGA GATTTGGGTA AAAGAACTTT TACTTCTGAT
     CCCCATAGGT ACCGACTTCG ACTTCGATCT CTAAACCCAT TTTCTTGAAA ATGAAGACTA
     ValSerSerTyr LeuGluGly GlnAlaAla LysGluPheIle AlaTrpLeu ValArgGly
295  GTTTCTTCTT ATTTGGAAGG TCAAGCTGCT AAAGAATTTA TTGCTTGGTT GGTTAGAGGT
     CAAAGAAGAA TAAACCTTCC AGTTCGACGA TTTCTTAAAT AACGAACCAA CCAATCTCCA
                 XbaI
                ~~~~~~
     ArgGly***
355  AGAGGTTAGA ATCTAGAAAC
     TCTCCAATCT TAGATCTTTG
```

T)

```
            NcoI
         ~~~~~~~
     GlyValSerMet AlaProGlu AlaGluAla ArgAspLeuGly LysArgThr PheThrSer
235  GGGGTATCCA TGGCTCCAGA AGCTGAAGCT AGAGATTTGG GTAAAAGAAC TTTTACTTCT
     CCCCATAGGT ACCGAGGTCT TCGACTTCGA TCTCTAAACC CATTTTCTTG AAAATGAAGA
     AspValSerSer TyrLeuGlu GlyGlnAla AlaLysGluPhe IleAlaTrp LeuValArg
295  GATGTTTCTT CTTATTTGGA AGGTCAAGCT GCTAAAGAAT TTATTGCTTG GTTGGTTAGA
     CTACAAAGAA GAATAAACCT TCCAGTTCGA CGATTTCTTA AATAACGAAC CAACCAATCT
                 XbaI
                ~~~~~~~
     GlyArgGly***
355  GGTAGAGGTT AGAATCTAGA AAC
     CCATCTCCAA TCTTAGATCT TTG
```

U)

```
            NcoI
         ~~~~~~~
     GlyValSerMet AlaGluGlu AlaGluLys ArgThrPheThr SerAspVal SerSerTyr
235  GGGGTATCCA TGGCTGAAGA AGCTGAAAAA AGAACTTTTA CTTCTGATGT TTCTTCTTAT
     CCCCATAGGT ACCGACTTCT TCGACTTTTT TCTTGAAAAT GAAGACTACA AAGAAGAATA

XbaI
                                                                   ~
     LeuGluGlyGln AlaAlaLys GluPheIle AlaTrpLeuVal ArgGlyArg Gly***
295  TTGGAAGGTC AAGCTGCTAA AGAATTTATT GCTTGGTTGG TTAGAGGTAG AGGTTAGAAT
     AACCTTCCAG TTCGACGATT TCTTAAATAA CGAACCAACC AATCTCCATC TCCAATCTTA
     XbaI
     ~~~~~
355  CTAGAAAC
     GATCTTTG
```

Fig. 4 S)–U)

V)
```
              NcoI
              ~~~~~~~
    GlyValSerMet AlaGluGlu AlaGluArg AspLeuGlyLys ArgThrPhe ThrSerAsp
235 GGGGTATCCA TGGCTGAAGA AGCTGAAAGA GATTTGGGTA AAAGAACTTT TACTTCTGAT
    CCCCATAGGT ACCGACTTCT TCGACTTTCT CTAAACCCAT TTTCTTGAAA ATGAAGACTA
    ValSerSerTyr LeuGluGly GlnAlaAla LysGluPheIle AlaTrpLeu ValArgGly
295 GTTTCTTCTT ATTTGGAAGG TCAAGCTGCT AAAGAATTTA TTGCTTGGTT GGTTAGAGGT
    CAAAGAAGAA TAAACCTTCC AGTTCGACGA TTTCTTAAAT AACGAACCAA CCAATCTCCA
                    XbaI
                    ~~~~~~
    ArgGly***
355 AGAGGTTAGA ATCTAGAAAC
    TCTCCAATCT TAGATCTTTG
```

X)
```
              NcoI
              ~~~~~~~
    GlyValSerMet AlaArgAsp LeuGlyGlu GluAlaGluLys ArgThrPhe ThrSerAsp
235 GGGGTATCCA TGGCTAGAGA TTTGGGTGAA GAAGCTGAAA AAAGAACTTT TACTTCTGAT
    CCCCATAGGT ACCGATCTCT AAACCCACTT CTTCGACTTT TTTCTTGAAA ATGAAGACTA
    ValSerSerTyr LeuGluGly GlnAlaAla LysGluPheIle AlaTrpLeu ValArgGly
295 GTTTCTTCTT ATTTGGAAGG TCAAGCTGCT AAAGAATTTA TTGCTTGGTT GGTTAGAGGT
    CAAAGAAGAA TAAACCTTCC AGTTCGACGA TTTCTTAAAT AACGAACCAA CCAATCTCCA
                    XbaI
                    ~~~~~~
    ArgGly***
355 AGAGGTTAGA ATCTAGAAAC
    TCTCCAATCT TAGATCTTTG
```

Y)
```
              NcoI
              ~~~~~~~
    GlyValSerMet AlaGluGlu AlaGluLeu AlaLysArgThr PheThrSer AspValSer
235 GGGGTATCCA TGGCTGAAGA AGCTGAATTG GCTAAAAGAA CTTTTACTTC TGATGTTTCT
    CCCCATAGGT ACCGACTTCT TCGACTTAAC CGATTTTCTT GAAAATGAAG ACTACAAAGA
    SerTyrLeuGlu GlyGlnAla AlaLysGlu PheIleAlaTrp LeuValArg GlyArgGly
295 TCTTATTTGG AAGGTCAAGC TGCTAAAGAA TTTATTGCTT GGTTGGTTAG AGGTAGAGGT
    AGAATAAACC TTCCAGTTCG ACGATTTCTT AAATAACGAA CCAACCAATC TCCATCTCCA
                XbaI
                ~~~~~~
    ***
355 TAGAATCTAG AAAC
    ATCTTAGATC TTTG
```

```
            NcoI
         ~~~~~~~
    GlyValSerMet AlaGluGlu AlaGluLeu GlyLysArgThr PheThrSer AspValSer
235 GGGGTATCCA TGGCTGAAGA AGCTGAATTG GGTAAAAGAA CTTTTACTTC TGATGTTTCT
    CCCCATAGGT ACCGACTTCT TCGACTTAAC CCATTTTCTT GAAAATGAAG ACTACAAAGA
    SerTyrLeuGlu GlyGlnAla AlaLysGlu PheIleAlaTrp LeuValArg GlyArgGly
295 TCTTATTTGG AAGGTCAAGC TGCTAAAGAA TTTATTGCTT GGTTGGTTAG AGGTAGAGGT
    AGAATAAACC TTCCAGTTCG ACGATTTCTT AAATAACGAA CCAACCAATC TCCATCTCCA
            XbaI
         ~~~~~~~
    ***
355 TAGAATCTAG AAAC
    ATCTTAGATC TTTG
```

Fig. 4 z)

SEMI-RECOMBINANT PREPARATION OF GLP-1 ANALOGUES

CROSS-REFERENCE TO RELATED APPLICATIONS

This application is a 35U.S.C. §371 national stage application of International Patent Application PCT/EP2008/068211 (published as WO 2009/083549), filed Dec. 22, 2008, which claimed priority of European Patent Application 07124141.8, filed Dec, 28, 2007; this application further claims priority under 35 U.S.C. §119 of U.S. Provisional Application 61/018,559, filed Jan. 2, 2008.

FIELD OF THE INVENTION

The present invention is related to a semi-recombinant method for the preparation of GLP-1 analogues and derivatives containing non-proteogenic amino acids in the N-terminal part combining the use of recombinant expression techniques and chemical peptide synthesis.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 8, 2010. The Sequence Listing is made up of 13 kilobytes, and the information contained in the attached "SEQUENCE LISTING" is identical to the information in the specification as originally filed. No new matter is added.

BACKGROUND OF THE INVENTION

Human glucagon-like peptide-1 (GLP-1) is a 37 amino acid residue gastrointestinal hormone involved in the regulation of blood glucose metabolism, gastrointestinal secretion and metabolism and food intake. GLP-1 is originating from preproglucagon which is synthesized inter alia in the L-cells in the distal ileum, in the pancreas and in the brain. GLP-1 stimulates insulin secretion in a glucose-dependant manner, stimulates insulin biosynthesis, promotes beta cell rescue, decreases glucagon secretion, gastric emptying and food intake. Human GLP-1 is hydrolysed to GLP-1 (7-37) and GLP-1 (7-36)-amide which are both insulinotropic agents. Pharmacological doses of GLP-1 administered to type 2 diabetic patients have been shown to significantly raise circulating insulin levels and to lower plasma glucagon levels. The actions of GLP-1 are mediated by GLP-1 receptors in the pancreas, heart, kidney, central nervous system and gastrointestinal tract. Hence, GLP-1 is expected to become very important in the treatment of diabetes.

However, native human GLP-1 is rapidly inactivated by degradation by the plasma enzyme dipeptidyl peptidase IV (DPP-IV) to a truncated GLP-1(9-36)amide metabolite, which serves as a GLP-1 receptor antagonist. This confers the peptide with a short circulating half-life.

This short circulating half-life is a problem for many diabetes patients particularly in the type 2 diabetes segment who are subject to so-called "needle-phobia", i.e. a substantial fear of injecting themselves. In the type 2 diabetes segment most patients are treated with oral hypoglycaemic agents. Since GLP-1 compounds are expected to be an injectable pharmaceutical product, the fear of injections may become a serious obstacle for the widespread use of these clinically very promising compounds.

Hence, a range of different approaches and methods have been used for modifying the structure of GLP-1 compounds in order to provide a longer duration of action in vivo. Thus, a considerable effort is e.g. being made to develop analogues and derivatives of GLP-1 compounds less susceptible to DPP-IV mediated hydrolysis in order to reduce the rate of degradation by DPP-IV. WO 2006/097538, WO 2006/097536, WO 2006/037810, WO2006/005667, WO2005/058958, WO 2005/027978, WO 98/08871 and US 2001/0011071 describe various GLP-1 analogues and derivatives, including GLP analogues comprising non-proteogenic amino acids (i.e. non-natural amino acids) which may confer a certain protection against hydrolysis by DPP-IV.

Polypeptides containing only proteogenic amino acids (i.e. natural amino acids) such as native GLP-1, can be produced using recombinant techniques or via chemical synthesis. However, polypeptides also containing non-proteogenic amino acids such as N-terminally extended GLP-1 analogues, cannot currently be prepared via recombinant expression techniques in a practical way and are in general prepared via chemical synthesis. The most widely used method for peptide synthesis is solid phase peptide synthesis where the adequate protected amino acids are incorporated in a stepwise manner using a polymer as a solid support.

Solid phase peptide synthesis (SPPS) can be very efficient in the preparation of some peptides, but the use of protected amino acids in combination with the consistent use of excess of reactants makes this approach relatively expensive. In addition, each amino acid prolongation in a solid phase polypeptide synthesis requires a thorough washing procedure. Typically, incorporation of one amino acid involves up to 10 washings steps with solvents like NMP, DMF or DCM.

When polypeptides, such as insulinotropic agents, GLP-1 analogues, truncated analogues of GLP-1 and derivatives of GLP-1 are synthesized using SPPS, the formation of secondary structures during the synthesis often leads to lower efficiency of the individual synthetic steps. As a consequence, larger peptides or peptides containing certain amino acid sequences are often produced in low purity and yields. The impurities are often deletion peptides where one or more amino acids are missing in the final sequence. These impurities can be very difficult to separate from the desired peptide, and result in a product contaminated with deletion peptides.

It is the aim of the present invention to provide an efficient and economic method for the preparation of GLP-1 analogues and derivatives which are DPP-IV protected by having non-proteogenic amino acids in the N-terminal part. The method combines the advantage of cost-efficient production of truncated GLP-1 precursor molecules, using recombinant techniques together with chemical synthesis of N-terminal extensions comprising non-proteogenic amino acids. A significant reduction of the cost of producing GLP-1 analogues or derivatives is achieved. Less expensive GLP-1 analogues and derivatives are highly desirable for maximizing the number of patients for whom treatment is available, as well as for exploiting the advantages of alternative delivery routes which have lower bioavailability than subcutaneous injection, e.g. transdermal and pulmonal delivery.

SUMMARY OF THE INVENTION

In its broadest aspect the present invention is related to a method for producing GLP-1 analogues and derivatives being DPP-IV protected by comprising one or more non-proteogenic amino acids in the N-terminal part.

Thus, in one aspect the present invention is related to a method for making GLP-1 analogues and derivatives comprising one or more non-proteogenic amino acids, said method comprising the following steps:

(i) culturing a host cell comprising a nucleotide sequence encoding a precursor molecule of said GLP-1 analogue or derivative under suitable conditions for expression of said precursor molecule,
(ii) separating the expressed precursor molecule from the culture broth,
(iii) coupling an N-terminal amino acid extension comprising one or more non-proteogenic amino acids to the expressed precursor molecule,
(iv) isolating the resulting GLP-1 analogue or derivative by suitable means, as known in the art.

BRIEF DESCRIPTION OF THE DRAWINGS

FIG. 2a-d shows the NcoI-XbaI DNA fragments encoding the GLP-1 precursors. The GLP-1precursor amino acid sequence encoded by the DNA fragments are indicated in bold. a) (R34)GLP-1(11-37); b) Ext1-(E22,R26,R34)GLP-1(8-37)K38-Ext2 and c) Ext1-(E22,R26,R34,K37)GLP-1(8-37)-Ext2; d)(R34)GLP-1(9-37).

FIG. 3 shows the NcoI-XbaI DNA fragments encoding the GLP-1 precursors and the optimized leader sequences. (34R)GLP-1(11-37) is shown as an unlimiting example. Capital letters indicate the different sequences. Optimized amino acid sequences encoded by the DNA fragments are indicated in bold. 'KR' indicates a construct with the minimal Kex2p cleavage site LysArg.

FIG. 4A-Z shows (34R)GLP-1(11-37) leader optimization as an example. Optimization of P1 to P6: (A-F). Incorporation of proline: (H, I). Charged amino acid incorporation into P7 to P11: (M-Z, K5-7, L2-4). Constructs for downstream processing with DAPase: (G, J, K, L). Yields are given in percent relative to a (34R)GLP-1(11-37) with the MFalpha*—leader and a simple LysArg Kex2p cleavage site.

DETAILED DESCRIPTION OF THE INVENTION

Figure 1:
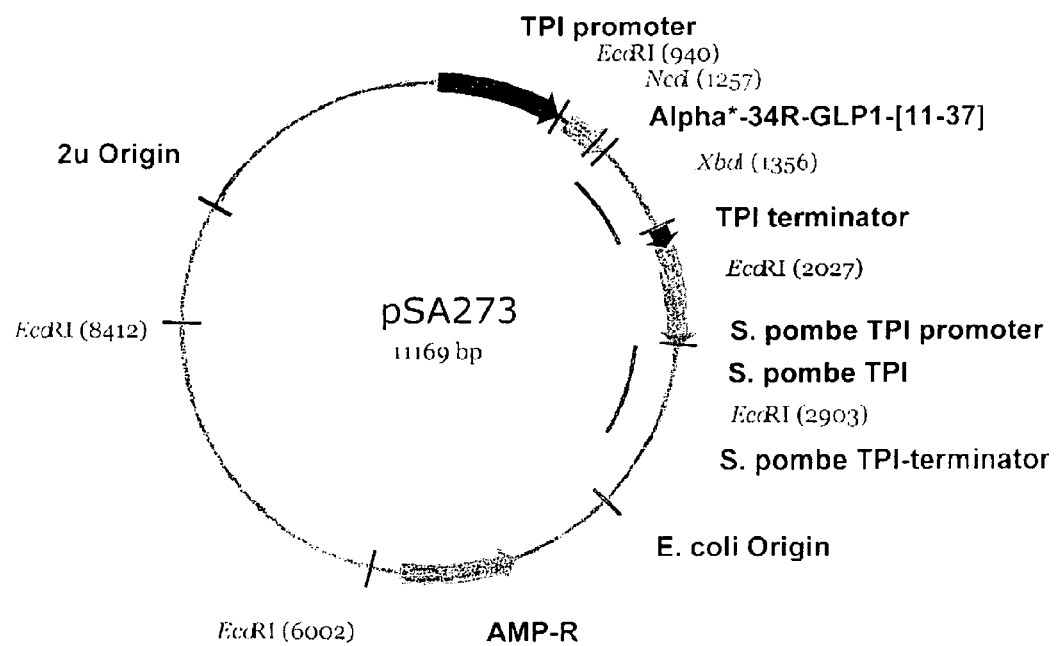
FIG. 1 shows the yeast plasmid pSA273. The plasmid contains an expression cassette comprising an EcoRI-XbaI fragment inserted into the plasmid between the transcription-promoter and the transcription-terminator of the *S. cerevisiae* TPI gene. The expression cassette encodes a fusion product composed of the MFα1* pre-pro leader, a Lys-Arg cleavage site for the dibasic processing endopeptidase Kex2, and the GLP-1 precursor (R34)GLP-1(11-37).

The present inventors have developed an economic and efficient method for preparing GLP-1 analogues and derivatives comprising one or more non-proteogenic amino acids in the N-terminal part. Thus, it has been found that recombinantly produced GLP-1 precursor molecules which contain only proteogenic amino acids can be efficiently extended in the N-terminus using a non-proteogenic amino acid or a peptide containing one or more non-proteogenic amino acids, e.g. by reacting the precursor of the GLP-1 analogue with a carboxylic acid derivative, which is optionally activated, of the extension fragment.

More specifically, the present invention provides a semi-recombinant method for preparation of GLP-1 analogues and derivatives containing one or more non-proteogenic amino acids in the N-terminus, including the positions 7, 8, 9 and/or 10. In addition, a useful method for derivatization of the ε-N of a lysine residue in the GLP-1 analogue precursor molecule via acylation is provided. Hence, the present invention combines the cost efficient production of GLP-1 analogues and derivatives using recombinant techniques with the flexibility of chemical synthesis.

In the present specification, the following terms have the indicated meaning:

The term "polypeptide" and "peptide" as used herein means a compound composed of at least two constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteogenic amino acids are: Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus, a non-proteogenic amino acid is a moiety which can be incorporated into a peptide via peptide bonds but is not a proteogenic amino acid. Examples of non-proteogenic aminoacids are, but not limited to, γ-carboxyglutamate, ornithine, phosphoserine, the D-amino acids such as D-alanine and D-glutamine. Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-Histidine, the beta analogs of amino acids such as β-alanine etc., D-histidine, desamino-histidine, 2-amino-histidine, β-hydroxy-histidine, homohistidine, $N^{\alpha}$-acetyl-histidine, α-fluoromethyl-histidine, α-methyl-histidine, 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid, α-methyl prolin, 1-methyl histidine, 3-methyl histidine, and 4,5,6,7-tetrahydro-1H-imidazo[4,5-C]pyridine-6-carboxylic acid 3-(1,2,4-triazol-1-yl)-alanin.

The term "DPP-IV protected" as used herein referring to a polypeptide means a polypeptide which has been chemically modified in order to render said compound resistant to the plasma peptidase dipeptidyl peptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to hydrolysis by DPP-IV in order to reduce the rate of degradation by DPP-IV. In one embodiment a DPP-IV protected peptide is more resistant to DPP-IV than GLP-1(7-37).

Resistance of a peptide to degradation by DPP-IV is determined by the following degradation assay:

Aliquots of the peptide (5 nmol) are incubated at 37° C. with 1 μL of purified DPP-IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl peptidase DPP-IV is estimated at incubation times which result in less than 10% of the peptide being hydrolysed.

In its broadest sense, the term "GLP-1 analogue" as used herein means an analogue of a molecule of the glucagon family of peptides or an analogue of the family of exendins. The glucagon family of peptides are encoded by the preproglucagon gene and encompasses three small peptides with a high degree of homology, i.e. glucagon (1-29), GLP-1 (1-37) and GLP-2 (1-33). Exendins are peptides expressed in lizards and like GLP-1, are insulinotropic. Examples of exendins are exendin-3 and exendin-4.

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been added to the peptide. Such addition or deletion of amino acid residues can take place at the N-terminal of the peptide and/or at the C-terminal of the peptide. Thus a GLP-1 analogue according to the invention is an analogue of GLP-1 (1-37) according to the invention wherein one or more amino acid residues of the peptide have been substituted by other amino acid residues and/or wherein one or more amino acid residues have been deleted from the peptide and/or wherein one or more amino acid residues have been added to the peptide.

For the present purposes any amino acid substitution, deletion, and/or addition refers to the sequence of human GLP-1(7-37) which is included herein as SEQ ID NO: 1. However, the numbering of the amino acid residues in the sequence listing always starts with no. 1, whereas for the present purpose we want, following the established practice in the art, to start with amino acid residue no. 7 and assign number 7 to it. Therefore, generally, any reference herein to a position number of the GLP-1(7-37) sequence is to the sequence starting with His at position 7 and ending with Gly at position 37.

A simple system is often used to describe GLP-1 analogues: for example [Arg$^{34}$]GLP-1(7-37)Lys designates a GLP-1(7-37) analogue wherein the naturally occurring lysine at position 34 has been substituted with arginine and wherein a lysine has been added to the C-terminal. Another example [Arg$^{34}$]GLP-1(11-37) designates a GLP-1 analogue wherein the naturally occurring lysine at position 34 has been substituted with arginine and the amino acids in positions 7, 8, 9 and 10 are absent.

The expression "a position equivalent to" when used herein to characterize a modified GLP-1(7-37) sequence refers to the corresponding position in the natural GLP-1(7-37) sequence (having the sequence of SEQ ID NO: 1). Corresponding positions are easily deduced, e.g. by simple handwriting and eyeballing. In the alternative, a standard protein or peptide alignment program may be used, such as "align" which is a Needleman-Wunsch alignment. The algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM50 and the default identity matrix may be used, and the penalty for the first residue in a gap may be set at −12 and the penalties for additional residues in a gap at −2.

The term "derivative" as used herein in relation to a peptide means a chemically modified peptide or an analogue thereof, wherein at least one substituent has been attached to the unmodified peptide or an analogue thereof, i.e. a peptide which has been covalently modified. Typical modifications are amides, carbohydrates, alkyl groups, acyl groups, esters and the like. An example of a derivative of GLP-1(7-37) is $N^{\epsilon 26}$-(γ-Glu($N^{\alpha}$-hexadecanoyl)))-[Arg$^{34}$, Lys$^{26}$])GLP-1(7-37).

All amino acids for which the optical isomer is not stated is to be understood to mean the L-isomer.

In embodiments of the invention a maximum of 17 amino acids in the GLP-1 analogue have been modified (substituted, deleted, added or any combination thereof) relative to human GLP-1(7-37). In embodiments of the invention a maximum of 15 amino acids in the GLP-1 analogue have been modified. In embodiments of the invention a maximum of 10 amino acids in the GLP-1 analogue have been modified. In embodiments of the invention a maximum of 8 amino acids in the GLP-1 analogue have been modified. In embodiments of the invention a maximum of 7 amino acids in the GLP-1 analogue have been modified. In embodiments of the invention a maximum of 6 amino acids in the GLP-1 analogue have been modified. In embodiments of the invention a maximum of 5 amino acids in the GLP-1 analogue have been modified. In embodiments of the invention a maximum of 4 amino acids in the GLP-1 analogue have been modified. In embodiments of the invention a maximum of 3 amino acids in the GLP-1 analogue have been modified. In embodiments of the invention a maximum of 2 amino acids in the GLP-1 analogue have been modified. In embodiments of the invention 1 amino acid in the GLP-1 analogue has been modified.

In one embodiment the GLP-1 analogue is an insulinotropic agent.

In one embodiment the GLP-1 analogue is a GLP-1 agonist.

The term "GLP-1 agonist" as used herein refers to any glucagon-like peptide which fully or partially activates the human GLP-1 receptor. In a preferred embodiment, the "GLP-1 agonist" is any glucagon-like peptide that binds to a GLP-1 receptor, preferably with an affinity constant (KD) or a potency ($EC_{50}$) of below 1 μM, e.g., below 100 nM as measured by methods known in the art (see e.g., WO 98/08871) and exhibits insulinotropic activity, where insulinotropic activity may be measured in vivo or in vitro assays known to those of ordinary skill in the art. For example, the GLP-1 agonist may be administered to an animal and the insulin concentration measured over time.

In one aspect of the invention, the GLP-1 analogue to be included in the pharmaceutical compositions of the present invention is an analogue of GLP-1, wherein the analogue comprises at least one non-proteogenic peptide.

In one aspect of the invention, the GLP-1 analogue is selected from the group consisting of Aib$^{8,22,35}$ GLP-1(7-37), Aib$^{8,35}$ GLP-1(7-37), Aib$^{8,22}$ GLP-1(7-37), Aib$^{8,22,35}$ Arg$^{26,34}$Lys$^{38}$GLP-1(7-38), Aib$^{8,35}$ Arg$^{26,34}$Lys$^{38}$GLP-1(7-38), Aib$^{8,22}$ Arg$^{26,34}$Lys$^{38}$GLP-1(7-38), Aib$^{8,22,35}$ Arg$^{26,34}$Lys$^{38}$GLP-1(7-38), Aib$^{8,35}$ Arg$^{26,34}$Lys$^{38}$GLP-1(7-38), Aib$^{8,22,35}$ Arg$^{26}$Lys$^{38}$GLP-1(7-38), Aib$^{8,35}$ Arg$^{26}$Lys$^{38}$GLP-1(7-38), Aib$^{8,22}$ Arg$^{26}$Lys$^{38}$GLP-1(7-38), Aib$^{8,22,35}$ Arg$^{34}$Lys$^{38}$GLP-1(7-38), Aib$^{8,35}$Arg$^{34}$Lys$^{38}$GLP-1(7-38), Aib$^{8,22}$Arg$^{34}$Lys$^{38}$GLP-1(7-38), Aib$^{8,22,35}$Ala$^{37}$Lys$^{38}$GLP-1(7-38), Aib$^{8,35}$Ala$^{37}$Lys$^{38}$GLP-1(7-38), Aib$^{8,22}$Ala$^{37}$Lys$^{38}$ GLP-1(7-38), Aib$^{8,22,35}$ Lys$^{37}$GLP-1(7-37), Aib$^{8,35}$Lys$^{37}$ GLP-1(7-37) and Aib$^{8,22}$Lys$^{37}$GLP-1(7-38).

In one aspect of the invention, the GLP-1 analogue is selected from the group consisting of
[desaminoHis$^7$,Glu$^{22}$,Arg$^{26}$,Arg$^{34}$,Lys$^{37}$]GLP-1(7-37) amide,
[desaminoHis$^7$,Arg$^{34}$]GLP-1-(7-37), [Aib$^8$,Glu$^{22}$,Arg$^{26}$, Arg$^{34}$,Lys$^{37}$]GLP-1-(7-37)amide,
[DesaminoHis$^7$, Glu$^{22}$ Arg$^{26}$, Arg$^{34}$, Phe(m-CF3)$^{28}$]GLP-1-(7-37)amide,
[DesaminoHis$^7$,Glu$^{22}$,Arg$^{26}$,Arg$^{34}$]GLP-1-(7-37)-Lys,
[DesaminoHis$^7$,Glu$^{22}$,Arg$^{26}$,Arg$^{34}$]GLP-1-(7-37)-Lys,
[desaminoHis$^7$,Arg$^{26}$,Arg$^{34}$,]GLP-1-(7-37)-Lys,
[DesaminoHis$^7$,Glu$^{22}$,Arg$^{26}$,Arg$^{34}$,Lys$^{37}$]GLP-1-(7-37) amide,
[DesaminoHis$^7$,Arg$^{26}$,Arg$^{34}$,Lys$^{37}$]GLP-1-(7-37)amide,
[DesaminoHis$^7$,Glu$^{22}$,Arg$^{26}$,Arg$^{34}$,Lys$^{37}$]GLP-1-(7-37),
[DesaminoHis$^7$,Arg$^{26}$,Arg$^{34}$,Lys$^{37}$]GLP-1-(7-37),
[DesaminoHis$^7$,Glu$^{22}$,Arg$^{26}$,Glu$^{30}$,Arg$^{34}$,Lys$^{37}$]GLP-1-(7-37),
[Aib$^8$,Lys$^{20}$,Arg$^{26}$,Glu$^{30}$,Thr(O-benzyl)$^{33}$,]GLP-1-(7-37) amide,
[Aib$^8$,Glu$^{22}$,Arg$^{26}$,Lys$^{30}$]GLP-1-(7-37), [Aib$^8$, Glu$^{22}$, Arg$^{26}$,Lys$^{31}$]GLP-1-(7-37),
[Aib$^8$,Lys$^{20}$,Arg$^{26}$,2-Naphtylalanine$^{28}$, Glu$^{30}$,]GLP-1 (7-37) amide,
[Aib$^8$, Glu$^{22}$, Arg$^{26}$, Arg$^{34}$,]GLP-1-(7-37)-Lys,
[Aib$^8$,Lys$^{20}$,Arg$^{26}$, 2-Naphtylalanine12, Glu$^{30}$,]GLP-1-(7-37)amide,
[Aib$^8$,Glu$^{22}$,Arg$^{26}$,Lys$^{31}$,Arg$^{34}$]GLP-1-(7-37),
[Aib$^8$,Arg$^{34}$]GLP-1-(7-37),
[Aib$^8$,Arg$^{34}$]GLP-1-(7-37)-amide,
[Aib$^8$,Lys$^{18}$,Arg$^{26}$,Arg$^{34}$]GLP-1(7-37),
[Aib$^8$,Glu$^{22}$,Arg$^{26}$,Arg$^{34}$,Lys$^{37}$]GLP-1-(7-37)amide,
[Aib$^8$, Lys$^{26}$]GLP-1 (7-37)amide,
[Aib$^8$,Arg$^{34}$]GLP-1-(7-34),
[Aib$^8$,Arg$^{34}$]GLP-1-(7-35),
[Aib$^8$,Lys$^{33}$,Arg$^{34}$]GLP-1-(7-34),
[Aib$^8$,Arg$^{34}$]GLP-1-(7-36)amide,
[Aib$^8$,Lys$^{26}$,Arg$^{34}$]GLP-1-(7-36)amide,
[Aib$^8$,Glu$^{22}$,Arg$^{26}$,Arg$^{34}$]GLP-1-(7-37)Lys,
[Aib$^8$,Lys$^{20}$,Glu$^{22}$,Arg$^{26}$,Glu$^{30}$,Pro$^{37}$]GLP-1-(7-37)amide,
[Aib$^8$,Glu$^{22}$,Arg$^{26}$,Arg$^{34}$,Lys$^{37}$]GLP-1-(7-37)amide,
[DesaminoHis$^7$,Glu$^{22}$,Arg$^{26}$,Arg$^{34}$,Lys$^{37}$]GLP-1-(7-37) amide,
[DesaminoHis$^7$,Arg26,Arg34,Lys$^{37}$]GLP-1-(7-37)amide,
Aib$^8$,Glu$^{22}$,Arg$^{26}$,Glu$^{30}$,Pro$^{37}$NLP-1-(7-37)Lys,
[Aib$^8$,Glu$^{22}$,Arg$^{26}$,Glu$^{30}$,Pro$^{37}$]GLP-1-((7-37)Lys,
[Aib$^8$,Arg$^{26}$,Arg$^{34}$]GLP-1-(7-37).

In yet another embodiment, the GLP-1 analogue to be included in the pharmaceutical compositions of the present invention is an analogue of GLP-2, wherein the analogue comprises at least one non-proteogenic peptide.

In yet another embodiment the GLP-1 analogue is an analogue of exendin-4 or exendin-3, wherein the analogue comprises at least one non-proteogenic peptide. Examples of exendins as well as analogues thereof are disclosed in WO 97/46584, U.S. Pat. No. 5,424,286 and WO 01/04156. U.S. Pat. No. 5,424,286 describe a method for stimulating insulin release with an exendin peptide. The exendin peptides disclosed include HGEGTFTSDLSKQMEEEAVR-LFIEWLKNGGX (SEQ ID NO. 12), wherein X-P or Y, and wherein exendin-3 is HSDGTFITSDLSKQMEEEAVR-LFIEWLKNGGPSSGAPPPS (SEQ ID NO. 13) and exendin-4 (1-39) is HGEGTFITSDLSKQMEEEAVR-LFIEWLKNGGPSSGAPPPS (SEQ ID NO. 2). WO 97/46584 describes truncated versions of exendin peptide(s). The disclosed peptides increase secretion and biosynthesis of insulin, but reduce those of glucagon. WO 01/04156 describes exendin-4 analogues and derivatives as well as the preparation of these molecules.

The term "exendin-4 peptide" as used herein means exendin-4(1-39) (SEQ ID NO. 2), an exendin-4(1-39) analogue, an exendin-4(1-39) derivative or a derivative of an exendin-4(1-39) analogue, insulinotropic fragments thereof, insulinotropic analogs thereof and insulinotropic derivatives thereof. Insulinotropic fragments of exendin-4 are insulinotropic agents for which the entire sequence can be found in the sequence of exendin-4 (SEQ ID NO. 2) and where at least one terminal amino acid has been deleted. Examples of insulinotropic fragments of exendin-4(1-39) are exendin-4 (1-38) and exendin-4(1-31).

The insulinotropic property of a compound may be determined by in vivo or in vitro assays well known in the art. For instance, the compound may be administered to an animal and monitoring the insulin concentration over time. Insulinotropic analogs of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analog of exendin-4(1-39) is Ser$^2$Asp$^3$-exendin-4(1-39) wherein the amino acid residues in position 2 and 3 have been replaced with serine and aspartic acid, respectively (this particular analog also being known in the art as exendin-3). Insulinotropic derivatives of exendin-4(1-39) and analogs thereof are what the person skilled in the art considers to be derivatives of these peptides, i.e., having at least one substituent which is not present in the parent peptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivatives of exendin-4(1-39) and analogs thereof is Tyr$^{31}$-exendin-4(1-31)-amide.

The term "stable exendin-4 compound" as used herein means a chemically modified exendin-4(1-39), i.e., an acylated exendin-3 or acylated exendin-4 analogue which exhibits an in vivo plasma elimination half-life of at least 10 hours in man, as determined by conventional methods.

All amino acids for which the optical isomer is not stated is to be understood to mean the L-isomer.

The term "insulinotropic agent" as used herein means a compound which is an agonist of the human GLP-1 receptor, i.e. a compound which stimulates the formation of cAMP in a suitable medium containing the human GLP-1 receptor (one such medium disclosed below). The potency of an insulinotropic agent is determined by calculating the EC$_{50}$ value from the dose-response curve as described below.

Baby hamster kidney (BHK) cells expressing the cloned human GLP-1 receptor (BHK-467-12A) were grown in DMEM media with the addition of 100 IU/mL penicillin, 100 µg/mL streptomycin, 5% fetal calf serum and 0.5 mg/mL Geneticin G-418 (Life Technologies). The cells were washed twice in phosphate buffered saline and harvested with Versene. Plasma membranes were prepared from the cells by homogenisation with an Ultraturrax in buffer 1 (20 mM HEPES-Na, 10 mM EDTA, pH 7.4). The homogenate was centrifuged at 48,000×g for 15 min at 4° C. The pellet was suspended by homogenization in buffer 2 (20 mM HEPES-Na, 0.1 mM EDTA, pH 7.4), then centrifuged at 48,000×g for 15 min at 4° C. The washing procedure was repeated one more time. The final pellet was suspended in buffer 2 and used immediately for assays or stored at −80° C.

The functional receptor assay was carried out by measuring cyclic AMP (cAMP) as a response to stimulation by the insulinotropic agent. cAMP formed was quantified by the AlphaScreen™ cAMP Kit (Perkin Elmer Life Sciences). Incubations were carried out in half-area 96-well microtiter plates in a total volume of 50 µL buffer 3 (50 mM Tris-HCl, 5 mM HEPES, 10 mM $MgCl_2$, pH 7.4) and with the following additions: 1 mM ATP, 1 µM GTP, 0.5 mM 3-isobutyl-1-methylxanthine (IBMX), 0.01% Tween-20, 0.1% BSA, 6 µg membrane preparation, 15 µg/mL acceptor beads, 20 µg/mL donor beads preincubated with 6 nM biotinyl-cAMP. Compounds to be tested for agonist activity were dissolved and diluted in buffer 3. GTP was freshly prepared for each experiment. The plate was incubated in the dark with slow agitation for three hours at room temperature followed by counting in the Fusion™ instrument (Perkin Elmer Life Sciences). Concentration-response curves were plotted for the individual compounds and $EC_{50}$ values estimated using a four-parameter logistic model with Prism v. 4.0 (GraphPad, Carlsbad, Calif.).

The term "semi-recombinant" as used herein refers to a method comprising the steps of preparing a first peptide fragment such as a first fragment of a GLP-1 analogue by a recombinant process, i.e. from a culture of host cells, and subsequently coupling a second fragment of a peptide to the first fragment of the peptide, wherein the second fragment is prepared chemically, i.e. in solution or on a resin using solid phase peptide chemistry. The coupling of the fragments may be performed either chemically or enzymatically.

The term "separating the expressed precursor molecule" as used herein means any kind of separation, including isolation of the recombinantly produced compound and also includes disintegrating or permeabilising a host cell.

Accordingly, the present invention relates to a method for making a GLP-1 analogue or derivative comprising one or more non-proteogenic amino acids in the N-terminal part, said method comprising the steps of:
(i) culturing a host cell comprising a nucleotide sequence encoding a precursor molecule of said GLP-1 analogue or derivative under suitable conditions for expression of said precursor molecule,
(ii) separating the expressed precursor molecule from the culture broth,
(iii) coupling an N-terminal amino acid extension comprising one or more non-proteogenic amino acids to the expressed precursor molecule,
(iv) isolating the resulting GLP-1 analogue or derivative by suitable means, as known in the art.

In the present context, the term "precursor molecule of the GLP-1 analogue", is to be understood as a peptide derived from GLP-1, GLP-2, Exendin-3 or Exendin-4 peptides, i.e., a GLP-1 analogue sequence, before addition of an N-terminal amino acid extension. Examples include, but are not limited to human GLP-1 (11-37) or an analogue thereof, human GLP-1 (9-37) or an analogue thereof and human GLP-1 (8-37) or an analogue thereof.

Accordingly, in one aspect the precursor molecule of the GLP-1 analogue according to the invention, comprises a GLP-1 peptide derived from the GLP-1 (7-37) sequence as shown in SEQ ID NO:1.

Exendin-4 is a 39 amino acid residue peptide isolated from the venom of Gila monster lizards (*Heloderma suspectum* and *Heloderma horridum*). This peptide shares 52% homology with GLP-1 (7-37) in the overlapping region. Exendin-4 is a potent GLP-1 receptor agonist and has also been shown to stimulate insulin release and ensuing lowering of the blood glucose level when injected into dogs.

Thus, due to the 52% homology with GLP-1 (7-37) in the overlapping region, the precursor molecule of the GLP-1 analogue according to the invention, may in certain embodiments be derived from an exendin-4 peptide as shown in SEQ ID NO:2.

Accordingly, the precursor molecules of the GLP-1 analogue may in a further aspect comprise an amino acid sequence of the general formula:

(SEQ ID NO: 3)
Thr-Phe-Thr-Ser-Asp-$Xaa_{16}$-Ser-$Xaa_{18}$-$Xaa_{19}$-$Xaa_{20}$-

Glu-$Xaa_{22}$-$Xaa_{23}$-Ala-$Xaa_{25}$-$Xaa_{26}$-$Xaa_{27}$-Phe-Ile- $Xaa_{30}$-Trp-Leu-$Xaa_{33}$-$Xaa_{34}$-$Xaa_{35}$-$Xaa_{36}$-$Xaa_{37}$-$Xaa_{38}$-

$Xaa_{39}$-$Xaa_{40}$-$Xaa_{41}$-$Xaa_{42}$-$Xaa_{43}$-$Xaa_{44}$-$Xaa_{45}$ wherein
$Xaa_{16}$ is Val or Leu;
$Xaa_{18}$ is Ser, Lys or Arg;
$Xaa_{19}$ is Tyr or Gln;
$Xaa_{20}$ is Leu or Met;
$Xaa_{22}$ is Gly or Glu;
$Xaa_{23}$ is Gln, Glu, Lys or Arg;
$Xaa_{25}$ is Ala or Val;
$Xaa_{26}$ is Lys, Glu or Arg;
$Xaa_{27}$ is Glu or Leu;
$Xaa_{30}$ is Ala, Glu or Arg;
$Xaa_{33}$ is Val, Lys or Arg;
$Xaa_{34}$ is Lys, Glu, Asn, His or Arg;
$Xaa_{35}$ is Gly;
$Xaa_{36}$ is Arg, Gly or Lys;
$Xaa_{37}$ is Gly, Ala, Glu, Pro, Lys, or is absent;
$Xaa_{38}$ is Lys, Ser, or is absent.
$Xaa_{39}$ is Ser, Lys, or is absent;
$Xaa_{40}$ is Gly, or is absent;
$Xaa_{41}$ is Ala, or is absent;
$Xaa_{42}$ is Pro, or is absent;
$Xaa_{43}$ is Pro, or is absent;
$Xaa_{44}$ is Pro, or is absent;
$Xaa_{45}$ is Ser, or is absent;
provided that if $Xaa_{38}$, $Xaa_{39}$, $Xaa_{40}$, $Xaa_{41}$, $Xaa_{42}$, $Xaa_{43}$, $Xaa_{44}$ or $Xaa_{45}$ is absent then each amino acid residue downstream is also absent.

In a further aspect of the invention, the precursor molecule of the GLP-1 analogue is selected from the list of precursor molecules comprising the amino acid sequence of the general formula:

(SEQ ID NO: 4)
Xaa$_9$-Xaa$_{10}$-Thr-Phe-Thr-Ser-Asp-Xaa$_{16}$-Ser-Xaa$_{18}$-

Xaa$_{19}$-Xaa$_{20}$-Glu-Xaa$_{22}$-Xaa$_{23}$-Ala-Xaa$_{25}$-Xaa$_{26}$-Xaa$_{27}$-

Phe-Ile-Xaa$_{30}$-Trp-Leu-Xaa$_{33}$-Xaa$_{34}$-Xaa$_{35}$-Xaa$_{36}$-

Xaa$_{37}$-Xaa$_{38}$-Xaa$_{39}$-Xaa$_{40}$-Xaa$_{41}$-Xaa$_{42}$-Xaa$_{43}$-Xaa$_{44}$-

Xaa$_{45}$ wherein
Xaa$_9$ is Glu or Asp
Xaa$_{10}$ is Gly or Ala
Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly or Glu;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val, Lys or Arg;
Xaa$_{34}$ is Lys, Glu, Asn, His or Arg;
Xaa$_{35}$ is Gly;
Xaa$_{36}$ is Arg, Gly or Lys;
Xaa$_{37}$ is Gly, Ala, Glu, Pro, Lys, or is absent;
Xaa$_{38}$ is Lys, Ser, or is absent.
Xaa$_{39}$ is Ser, Lys, or is absent;
Xaa$_{40}$ is Gly, or is absent;
Xaa$_{41}$ is Ala, or is absent;
Xaa$_{42}$ is Pro, or is absent;
Xaa$_{43}$ is Pro, or is absent;
Xaa$_{44}$ is Pro, or is absent;
Xaa$_{45}$ is Ser, or is absent;
provided that if Xaa$_{38}$, Xaa$_{39}$, Xaa$_{40}$, Xaa$_{41}$, Xaa$_{42}$, Xaa$_{43}$, Xaa$_{44}$ or Xaa$_{45}$ is absent then each amino acid residue downstream is also absent.

In a further aspect of the invention, the precursor molecule of the GLP-1 analogue is selected from the precursor molecules comprising an amino acid sequence of the general formula:

(SEQ ID NO: 5)
Xaa$_8$-Xaa$_9$-Xaa$_{10}$-Thr-Phe-Thr-Ser-Asp-Xaa$_{16}$-Ser-

Xaa$_{18}$-Xaa$_{19}$-Xaa$_{20}$-Glu-Xaa$_{22}$-Xaa$_{23}$-Ala-Xaa$_{25}$-Xaa$_{26}$-

Xaa$_{27}$-Phe-Ile-Xaa$_{30}$-Trp-Leu-Xaa$_{33}$-Xaa$_{34}$-Xaa$_{35}$-

Xaa$_{36}$-Xaa$_{37}$-Xaa$_{38}$-Xaa$_{39}$-Xaa$_{40}$-Xaa$_{41}$-Xaa$_{42}$-Xaa$_{43}$-

Xaa$_{44}$-Xaa$_{45}$ wherein
Xaa$_8$ is Ala, Gly, Val, Leu, Ile or Lys;
Xaa$_9$ is Glu or Asp;
Xaa$_{10}$ is Gly or Ala;
Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly or Glu;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val, Lys or Arg;
Xaa$_{34}$ is Lys, Glu, Asn, His or Arg;
Xaa$_{35}$ is Gly;
Xaa$_{36}$ is Arg, Gly or Lys;
Xaa$_{37}$ is Gly, Ala, Glu, Pro, Lys, or is absent;
Xaa$_{38}$ is Lys, Ser, or is absent;
Xaa$_{39}$ is Ser, Lys, or is absent;
Xaa$_{40}$ is Gly, or is absent;
Xaa$_{41}$ is Ala, or is absent;
Xaa$_{42}$ is Pro, or is absent;
Xaa$_{43}$ is Pro, or is absent;
Xaa$_{44}$ is Pro, or is absent;
Xaa$_{45}$ is Ser, or is absent;
provided that if Xaa$_{38}$, Xaa$_{39}$, Xaa$_{40}$, Xaa$_{41}$, Xaa$_{42}$, Xaa$_{43}$, Xaa$_{44}$ or Xaa$_{45}$ is absent then each amino acid residue downstream is also absent.

The GLP-1 analogue precursor molecules of the present invention may be prepared by means of recombinant DNA technology using general methods and principles known to the person skilled in the art, by culturing a suitable host cell comprising a nucleotide sequence encoding a precursor molecule of the GLP-1 analogue under suitable conditions for expression of the precursor molecule.

The nucleic acid sequence encoding the precursor molecule of the GLP-1 analogue may be prepared synthetically by established standard methods well known in the art, e.g. by synthesizing oligonucleotides in an automatic DNA synthesizer, and subsequently purify, anneal, ligate and clone the nucleic acid sequences into suitable vectors.

The cloning of the nucleic acid sequences encoding the precursor molecule of the GLP-1 analogue can be effected, e.g., by using the well known polymerase chain reaction (PCR).

The nucleic acid sequence encoding the precursor molecule of the GLP-1 analogue is inserted into a recombinant expression vector which may be any vector which may conveniently be subjected to recombinant DNA procedures. The choice of vector will often depend on the host cell into which it is to be introduced. Thus, the vector may be an autonomously replicating vector, i.e., a vector which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

For extracellular products the proteinaceous components of the supernatant are isolated by filtration, column chromatography or precipitation, e.g. microfiltration, ultrafiltration, isoelectric precipitation, purification by a variety of chromatographic procedures, e.g. ion exchange chromatography, hydrophobic interaction chromatography, gel filtration chromatography, affinity chromatography, or the like, dependent on the type of polypeptide in question. For intracellular or periplasmic products the cells isolated from the culture medium are disintegrated or permeabilised and extracted to recover the product polypeptide or precursor thereof.

The DNA sequence encoding the precursor molecule of the GLP-1 analogue may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence encoding the precursor molecule of the GLP-1 analogue may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome (s) into which it has been integrated.

The vector is preferably an expression vector in which the DNA sequence encoding the precursor molecule of the GLP-1 analogue is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the precursor molecule of the GLP-1 analogue may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate. For large scale manufacture the selectable marker preferably is not antibiotic resistance, e.g. antibiotic resistance genes in the vector are preferably excised when the vector is used for large scale manufacture. Methods for eliminating antibiotic resistance genes from vectors are known in the art, see e.g. U.S. Pat. No. 6,358,705 which is incorporated herein by reference.

To direct precursor molecule of the GLP-1 analogue of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the precursor molecule of the GLP-1 analogue, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the precursor molecule of the GLP-1 analogue and includes, but is not limited to, mammalian host cells, avian host cells, insect host cells, plant host cells, bacterial host cells, fungal host cells and yeast host cells. Examples of suitable host cells well known and used in the art include, but are not limited to *Saccharomyces cerevisiae, Pichia pastoris* and other yeasts, *E. coli, Bacillus subtilis*, and *Pseudomonas fluorescens* or mammalian BHK or CHO cell lines.

The methods of introducing exogenous nucleic acid into the hosts are well known in the art, and will vary with the host cell used. The host cell, when cultured under appropriate conditions, synthesizes a GLP-1 precursor molecule which can subsequently be collected from the culture medium (if the host cell secretes it into the medium) or directly from the host cell producing it (if it is not secreted).

In one embodiment, GLP-1 precursor molecules are produced in yeast cells. Yeast expression hosts are well known in the art, and include but are not limited to *Saccharomyces cerevisiae, Candida albicans* and *C. maltosa, Hansenula polymorpha, Kluyveromyces fragilis* and *K. lactis, Pichia guillerimondii, Pichia methanolica* and *Pichia pastoris, Schizosaccharomyces pombe*, and *Yarrowia lipolytica*.

In a one embodiment, GLP-1 precursor molecules are produced in bacterial systems. Bacterial expression hosts are well known in the art, and include but are not limited to *E. coli, Bacillus subtilis, Pseudomonas fluorescens, Lactococcus lactis, Streptococcus cremoris*, and *Streptococcus lividans*.

In one embodiment, GLP-1 precursor molecules are expressed in filamentous fungi. Filametous fungi hosts are well known in the art, and include but are not limited to *Neurospora, Penicillium, Tolypocladium*, and *Aspergillus* hosts such as *Aspergillus nidulans, Aspergillus oryzea* and *Aspergillus niger*.

In one embodiment, GLP-1 precursor molecules are produced in insect cells. Expression systems have been developed for *Aedes aegypti, Autographa californica, Bombyx mori, Drosophila melangaster, Spodoptera frugiperda*, and *Trichoplusia ni*. Each of these cell lines is known by and available to those skilled in the art of protein expression.

In one embodiment, GLP-1 precursor molecules are produced in other higher eukaryotic cells. These include but are not limited to avian cells and plant cells such as *Chlamydomonas reinhardtii*.

In one embodiment, GLP-1 precursor molecules are produced in mammalian host cell lines. Examples of these include, but are not limited to Baby hamster kidney (BHK), Chinese hamster ovary (CHO) and COS cells. More specific examples include, but are not limited to monkey kidney CV1 line transformed by SV40 (COS-7, ATCC CRL 1651); human embryonic kidney line (293); human liver cells (Hep G2, HB 8065).

The appropriate host cell is selected by the person the skill in the art. The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection).

The precursor molecule of the GLP-1 analogue produced by the cells may then be separated from the culture broth or culture medium by conventional procedures including separating the host cells from the medium by centrifugation or filtration.

As mentioned above, it is an aspect of the present invention to couple an N-terminal amino acid extension comprising one or more non-proteogenic amino acids to the expressed GLP-1 analogue precursor molecule, in order to render the compound more resistant to the plasma peptidase dipeptidyl peptidase-4 (DPP-IV).

Such non-proteogenic amino acids may be selected from γ-carboxyglutamate, ornithine, phosphoserine, D-amino acids such as D-alanine and D-glutamine, D-alanine and D-leucine, Aib (α-aminoisobutyric acid), Abu (α-aminobutyric acid), Tle (tert-butylglycine), 3-aminomethyl benzoic acid, anthranilic acid, des-amino-Histidine, β-alanine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine, 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, (1-aminocyclooctyl) carboxylic acid, α-methyl prolin, 1-methyl histidine, 3-methyl histidine, and 4,5,6,7-tetrahydro-1H-imidazo[4,5-C]pyridine-6-carboxylic acid β-(1,2,4-triazol-1-yl)-alanine. The desamino-histidine, although not containing an amino group, is thus herein referred to as a non-proteogenic amino acid, for ease in classification and nomenclature.

In one aspect of the invention, the length of the N-terminal amino acid extension comprising one or more non-proteogenic amino acids is 1 amino acid, 2 amino acids, 3 amino acids or 4 amino acids.

In one aspect of the invention, the length of the N-terminal amino acid extension comprising one or more non-proteogenic amino acids is 1 amino acid, 2 amino acids or 4 amino acids.

In one aspect of the invention, the length of the N-terminal amino acid extension comprising one or more non-proteogenic amino acids is 1 amino acid or 2 amino acids.

In one aspect of the invention, the length of the N-terminal amino acid extension comprising one or more non-proteogenic amino acids is 2 amino acids.

In one aspect of the invention, the length of the N-terminal amino acid extension comprising one or more non-proteogenic amino acids is 1 amino acid.

It is contemplated that not all of the amino acids of the N-terminal amino acid extension necessarily are non-proteogenic amino acids. Hence, in certain aspects the N-terminal amino acid extension comprises 1, 2, 3 or 4 non-proteogenic amino acids.

In one aspect of the invention the N-terminal amino acid extension comprising one or more non-proteogenic amino acids has the general formula

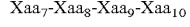

wherein $Xaa_7$ is selected from L-histidine, D-histidine, desamino-histidine, 2-amino-histidine, (β-hydroxy-histidine, homo-histidine, $N^\alpha$-acetyl-histidine, α-fluoromethyl-histidine, α-methyl-histidine, 3-pyridylalanine, 2-pyridylalanine and 4-pyridylalanine, 1-methyl histidine, 3-methyl histidine, and 4,5,6,7-tetrahydro-1H-imidazo[4,5-C]pyridine-6-carboxylic acid β-(1,2,4-triazol-1-yl)-alanine;

$Xaa_8$ is selected from Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid and alpha-methyl proline $Xaa_9$ is selected from Glu, Asp, γ,γ-dimethyl Glu, β,β-dimethyl Glu and β,β-dimethyl Asp, and $Xaa_{10}$ is selected from Gly, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, and (1-aminocyclooctyl) carboxylic acid.

The free carboxylic acid of the sequence $Xaa_7$-$Xaa_8$-$Xaa_9$-$Xaa_{10}$ may efficiently be prepared in a solution or on a resin such as 2-chlorotritylchloride resin e.g. via an Fmoc based strategy using adequately protected building blocks using appropriate reaction conditions described in references (Organic Synthesis on solid Phase, Florencio Zaragoza Dorwald, Wiley-VCH Verlag GmbH, D-69469 Weinheim, 2000), (Novabiochem Catalog, Merck Biosciences 2006/2007) and (Fmoc Solid Phase Peptide Synthesis, Edited by W. C. Chan and P. D. White, Oxford University Press, 2000, ISBN 0-19-963724-5). The amino acids in the sequence can be protected or unprotected. The N-terminal extension peptide of sequence $Xaa_7$-$Xaa_8$-$Xaa_9$-$Xaa_{10}$ may be activated to an activated acylating agent. The term "activated" acylating agent means an acylating agent which has been activated using general techniques as e.g. described in "Amide bond formation and peptide coupling" [Tetrahedron 61(46), 10827-10852 (2005)]. Examples of activated esters include, but are not limited to acid chloride, acid bromides, acid fluorides, symmetrical anhydride, mixed anhydride, carboxylic acids activated using common carbodiimides such as but not limited to diisopropylcarbodiimide (DIPCDI), N,N'-dicyclohexylcarbodiimide (DCC), 1-ethyl-3-(3'-dimethylaminopropyl)carbodiimide hydrochloride (EDC). Furthermore, included, but not limited to, are carboxylic acids using the aforementioned carbodiimides and an additive such as but not limited to N-hydroxybenzotriazol (HOBt), 1-Hydroxy-7-azabenzotriazole, 6-chloro-N-hydroxybenzotriazol (HOAt), 3-Hydroxy-3,4-dihydro-4-oxo-1,2,3-benzotriazine (DhbtOH). Also included, but not limited to, are carboxylic acids activated with an uronium salt or a phosphonium salt, such as but not limited to O-Benzotriazole-N,N,N',N'-tetramethyluronium hexafluorophosphate (HBTU), O-(Benzotriazol-1-yl)-N,N,N',N'-tetramethyluronium tetrafluoroborate (TBTU), 2-(6-Chloro-1H-benzotriazole-1-yl)-1,1,3,3-tetramethylaminium hexafluorophosphate (HCTU), (2-(6-Chloro-1H-benzotriazole-1-yl)-1,1,3,3-tetramethylaminium tetrafluoroborate) (TCTU), 2-(1H-7-Azabenzotriazol-1-yl)-1,1,3,3-tetramethyl uronium hexafluorophosphate (HATU), 1-benzotriazolyoxytris-(dimethylamino)phosphonium hexafluorophosphate (BOP) benzotriazol-1-yl-oxytripyrrolidinophosphonium hexafluorophosphate (PYBOP). Other activated esters include, but are not limited to esters of N-hydroxysuccinimid (NHS ester), pentafluorophenol ester (PfP-ester), 2,4-dinitrophenyl ester, 4-nitrophenyl ester, 3-Hydroxy-3,4-dihydro-4-oxo-1,2,3-benzotriazine (HODhbt) and Carbonyldiimidazole (CDI), N-ethyl-5-phenylisoxazolium-3'-sulfonate (NEPIS), preferably a N-hydroxysuccinimide ester or a HOBt ester or a derivative hereof using reaction conditions described in references (Organic Synthesis on solid Phase, Florencio Zaragoza Dorwald, Wiley-VCH Verlag GmbH, D-69469 Weinheim, 2000), (Novabiochem Catalog, Merck Biosciences 2006/2007) and (Fmoc Solid Phase Peptide Synthesis, Edited by W. C. Chan and P. D. White, Oxford University Press, 2000, ISBN 0-19-963724-5).

One example of an N-terminal extension peptide having the general formula

Xaa$_7$-Xaa$_8$-Xaa$_9$-Xaa$_{10}$ is;

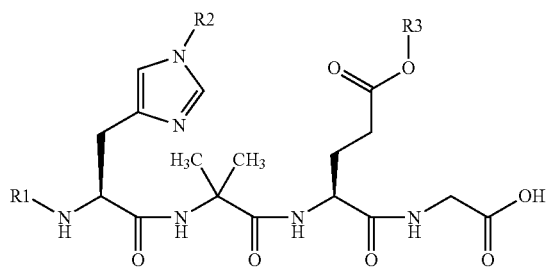

wherein R1 and R2 are individually chosen protecting groups such as but not limited to: Carbamates including but not limited to 9H-fluoren-9-ylmethoxycarbonyl (Fmoc), tert-butoxycarbonyl (Boc) and Benzylcarbarmate (Cbz); Amides including but not limited to benzamide; imides including but not limited to N-Phthalimide; and alkyls including but not limited to 1-Adamantyl (1-Adoc) and triphenylmethyl (Trt). In a preferred embodiment R1 is selected from the group consisting of 9H-fluoren-9-yl-methoxycarbonyl (Fmoc), tert-butoxycarbonyl (Boc) and benzylcarbarmate (Cbz), and R2 is selected from the group consisting of tert-butoxycarbonyl (Boc) and triphenylmethyl (Trt). R3 is an individually chosen protecting group such as but not limited to: Esters including but not limited to methyl, ethyl, tert-butyl, benzyl and 9H-fluoren-9-ylmethyl (Fm). In a preferred embodiment R3 is tert-butyl or benzyl.

An example of an N-terminal extension peptide of the sequence Xaa$_7$-Xaa$_8$-Xaa$_9$-Xaa$_{10}$ which is activated as the corresponding N-hydroxysuccinimide ester is;

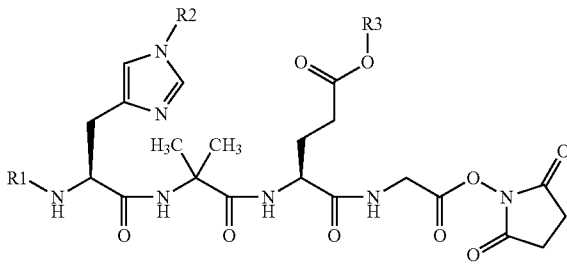

wherein R1, R2, and R3 are individually chosen protecting groups such as described above.

In a further aspect of the invention the N-terminal amino acid extension comprising one or more non-proteogenic amino acids has the general formula Xaa$_7$-Xaa$_8$ wherein Xaa$_7$ is selected from L-histidine, D-histidine, desamino-histidine, 2-amino-histidine, β-hydroxy-histidine, homo-histidine, N$^\alpha$-acetyl-histidine, α-fluoromethyl-histidine, α-methyl-histidine, 3-pyridylalanine, 2-pyridylalanine and 4-pyridylalanine; 1-methyl histidine, 3-methyl histidine, 4,5,6,7-tetrahydro-1H-imidazo[4,5-C]pyridine-6-carboxylic acid β-(1,2,4-triazol-1-yl)-alanine; and Xaa$_8$ is selected from Gly, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid and alpha-methyl proline The free carboxylic acid of the sequence Xaa$_7$-Xaa$_8$ may efficiently be prepared on a resin such as 2-chlorotritylchloride resin e.g. via an Fmoc based strategy using adequately protected building blocks using appropriate reaction conditions as described above or alternatively it may be prepared in solution. The amino acids in the sequence can be protected or unprotected.

The N-terminal extension peptide of sequence Xaa$_7$-Xaa$_8$ may be activated to activated acylating agents as described above.

An example of a N-terminal extension peptide with the formula Xaa$_7$-Xaa$_8$ is:

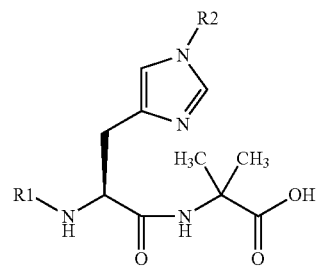

wherein R1 and R2 are individually chosen protecting groups as described above.

An example of an N-terminal extension peptide with the sequence Xaa$_7$-Xaa$_8$ which is activated as the corresponding N-hydroxysuccinimide ester is;

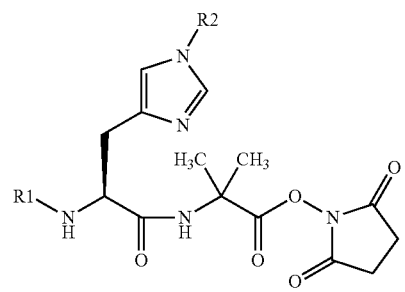

wherein R1 and R2 are individually chosen protecting groups as described above.

In a yet further aspect of the invention, the N-terminal amino acid extension comprising one non-proteogenic amino acid has the general formula Xaa$_7$ wherein Xaa$_7$ is selected from D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine and 4-pyridylalanine; 1-methyl histidine, 3-methyl histidine, and 4,5,6,7-tetrahydro-1H-imidazo[4,5-C]pyridine-6-carboxylic acid β-(1,2,4-triazol-1-yl)-alanine.

The free carboxylic acid of Xaa$_7$ may efficiently be prepared on a resin such as 2-chlortritylchloride resin using adequately protected building blocks using appropriate reaction conditions described as described above or alternatively may be prepared in a solution. The amino acid can be protected or unprotected.

The amino acid in the N-terminal extension Xaa$_7$ may be activated to an activated acylating agent as described above.

An example of an amino acid of the formula Xaa$_7$ is:

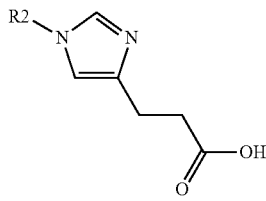

wherein R2 is a protecting group as described above or hydrogen.

An example of an amino acid of the formula Xaa$_7$ which is activated as the corresponding N-hydroxysuccinimide ester is:

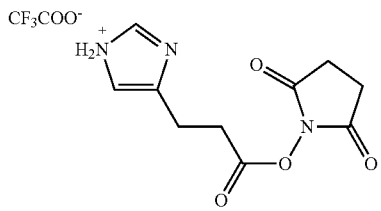 [SMILES: "CF3COO-" ; O=C(CCc1c[nH]cn1)ON1C(=O)CCC1=O]

In a further aspect of the invention, the GLP-1 analogue produced according to the invention, is a GLP-1 analogue wherein the N-terminal amino acid extension comprising one or more non-proteogenic amino acids has the general formula Xaa$_7$-Xaa$_8$-Xaa$_9$-Xaa$_{10}$ as defined above;

and the precursor molecule of said GLP-1 analogue has the general formula
Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Trp-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$-Xaa$_{44}$-Xaa$_{45}$ (SEQ ID NO: 3) as defined above.

In a further aspect of the invention, the GLP-1 analogue produced according to the invention, is a GLP-1 analogue wherein the N-terminal amino acid extension comprising one or more non-proteogenic amino acids has the general formula Xaa$_7$-Xaa$_8$ as defined above;

and the precursor molecule of said GLP-1 analogue has the general formula
Xaa$_9$-Xaa$_{10}$-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Trp-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$-Xaa$_{44}$-Xaa$_{45}$ (SEQ ID NO: 4) as defined above.

In a yet further aspect of the invention, the GLP-1 analogue produced according to the invention, is a GLP-1 analogue wherein the N-terminal amino acid extension comprising one or more non-proteogenic amino acids has the general formula Xaa$_7$ as defined above;

and the precursor molecule of said GLP-1 analogue has the general formula Xaa$_8$-Xaa$_9$-Xaa$_{10}$-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Trp-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$-Xaa$_{44}$-Xaa$_{45}$ (SEQ ID NO: 5) as defined above.

Coupling of additional amino acid analogues on an unprotected polypeptide fragment such as the GLP-1 analogue precursor molecule may not be a trivial task, due to the large number of possible side reactions that can take place under the reaction conditions used. An electrophilic reagent like for example an active ester such as an N-hydroxysuccinimide ester will in general react with nucleophiles present in a polypeptide. Such nucleophiles can be thiols, amines, imidazoles, phenolic hydroxy groups, alcohols, and guanidines. The rate of acylation on the functional groups will depend on the inherent reactivity of individual groups but also on the primary, secondary, tertiary and even quaternary structure of the polypeptide. Therefore it will often be difficult to forecast the relative reactivity of different amino acid moieties in a polypeptide. In practice reactions on an unprotected polypeptide give rise to mixtures of products. The relative reactivity of the individual groups in a polypeptide can however in some cases partly be controlled by the conditions under which the reaction is performed. Hence, a change in pH in a reaction mixture can lead to altered reactivity of some groups. Likewise, a change in the solvent from a non-protic to a protic one can result in altered reactivity of some groups.

In the method according to the invention, the coupling of the N-terminal amino acid extension comprising one or more non-proteogenic amino acids to the GLP-1 precursor molecule, may in certain useful embodiments take place in a solvent, including an organic polar solvent selected from 1-methyl-pyrrolidin-2-one, acetonitril, tetrahydrofuran, dimethylsulfoxide, N,N-dimethylformamide and N-methyl-formamide.

In other useful embodiments, the coupling of the N-terminal amino acid extension may take place in an aqueous solvent mixture, such as an aqueous solvent mixture that may comprise an organic polar solvent, such as a solvent selected from 1-methyl-pyrrolidin-2-one, acetonitril, tetrahydrofuran, dimethylsulfoxide, N,N-dimethylformamide and N-methyl-formamide.

Furthermore, it has been found that the coupling of the N-terminal amino acid extension according to the invention, may in useful embodiments take place in an aqueous solvent mixture, wherein the pH in the reaction mixture is between 6 and 12, such as between 7 and 10. In further embodiments the pH in the reaction mixture is in the range of 7-8, 8-9, 9-10 or 10-12.

As previously mentioned, the amino acids in the N-terminal amino acid extension comprising one or more non-proteogenic amino acids may comprise one or more protection groups. Hence, it is contemplated that the method according to the invention may further comprise one or more steps of removing one or more of these protection groups from the N-terminal amino acid extension comprising one or more non-proteogenic amino acids. Such deprotection steps are well described in the literature.

The method according to the invention may include a further step of acylating the epsilon-amino-group of at least one lysine residue in the expressed precursor molecule or the GLP-1 analogue obtained from coupling the N-terminal extension molecule to the expressed precursor molecule, with an acylating agent.

In certain embodiments it may be advantageous to conduct this step before the coupling of the N-terminal amino acid extension comprising one or more non-proteogenic amino acids to the GLP-1 analogue precursor molecule. Hence, the GLP-1 analogue precursor molecule used in the method according to the invention may in certain embodiments be acylated with an acylating agent, optionally activated, on e.g. an epsilon-amino-group of a lysine residue.

Thus, in one aspect the present invention is related to a method for making a GLP-1 analogue or derivative comprising one or more non-proteogenic amino acids in the N-terminal part, said method comprising the steps of:

(i) culturing a host cell comprising a nucleotide sequence encoding a precursor molecule of said GLP-1 analogue under suitable conditions for expression of said precursor molecule, (ii) separating the expressed precursor molecule from the culture broth, (iii) optionally acylating the epsilon-amino-group of at least one lysine residue in the expressed precursor molecule with an acylating agent, which is optionally activated, to obtain a precursor molecule derivative, and optionally isolating said precursor molecule derivative, (iv) coupling an N-terminal amino acid extension comprising one or more non-proteogenic amino acids to the expressed precursor molecule or precursor molecule derivative, (v) isolating the resulting GLP-1 analogue or derivative by suitable means.

The method according to the invention may optionally further include a step of selectively protecting the epsilon-amino-group of at least one lysine residue with an amine protecting agent as described above.

In certain embodiments it may be advantageous to conduct this protection step prior to the coupling of the N-terminal amino acid extension comprising one or more non-proteogenic amino acids to the GLP-1 analogue precursor molecule. Hence, the resulting lysine-protected GLP-1 analogue precursor molecule derivative used in the method according to said embodiment of the invention may be coupled to the N-terminal amino acid extension comprising one or more non-proteogenic amino acids. After said coupling of the N-terminal amino acid extension to the lysine-protected GLP-1 analogue precursor molecule, the protection group(s) on the epsilon amine groups of any lysine(s) may be removed using conventional techniques and the resulting epsilon-amino-group of a lysine may optionally be acylated with an acylating agent, optionally activated.

Thus, in one aspect the present invention is related to a method for making a GLP-1 analogue comprising one or more non-proteogenic amino acids in the N-terminal part, said method comprising the steps of:

(i) culturing a host cell comprising a nucleotide sequence encoding a precursor molecule of said insulinotropic peptide under suitable conditions for expression of said precursor molecule, (ii) separating the expressed precursor molecule from the culture broth, (iii) protecting the epsilon-amino-group of at least one lysine residue in the expressed precursor molecule with a protecting agent to obtain a protected precursor molecule, and optionally isolating said protected precursor molecule, (iv) coupling an N-terminal amino acid extension comprising one or more non-proteogenic amino acids to the protected precursor molecule to obtain a protected GLP-1 analogue and optionally isolating said protected GLP-1 analogue, (v) deprotection of epsilon amino protection groups, and optionally isolating the resulting GLP-1 analogue, (vi) optionally acylating the epsilon-amino-group of at least one lysine residue in the GLP-1 analogue with an acylating agent, which is optionally activated, to obtain a precursor molecule derivative, (vii) isolating the resulting GLP-1 analogue or derivative by suitable means, as known in the art.

In one aspect of the invention, the acylating agent used in the acylation of the epsilon-amino-group of a lysine residue is a carboxylic acid analogue of the general formula:

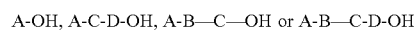

wherein one terminal free carboxylic acid, such as the —OH group of A-OH, A-C-D-OH, A-B—C—OH or A-B—C-D-OH, optionally is activated and wherein any other contained free carboxylic acid(s) optionally are protected with appropriate protecting group(s) e.g. selected from but not limited to tert-butyl, benzyl or allyl and
wherein
A is selected from the group consisting of;

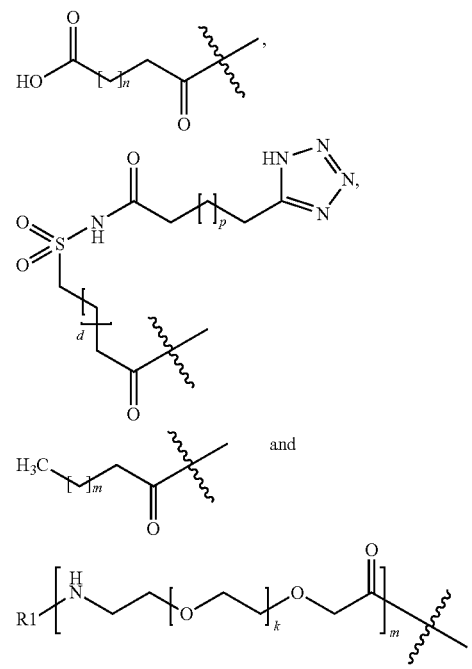

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, and m is selected from the group consisting of 11, 12, 13, 14, 15, 16, 17, k is selected from the group consisting of 0, 1, 2, 3, 4, 5, 11 and 27, and m is selected from the group consisting of 0, 1, 2, 3, 4, 5 and 6, and R1 is selected from the group of 9H-fluoren-9-ylmethoxycarbonyl (Fmoc), tert-butoxycarbonyl (Boc), Benzylcarbamate (Cbz)—

B is selected from the group consisting of

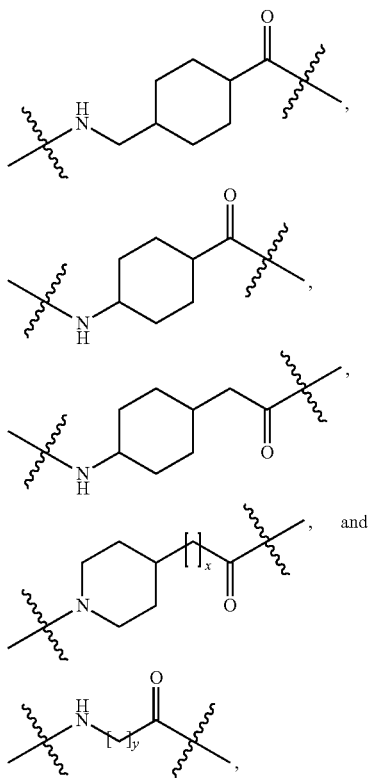

wherein x is selected from the group consisting of 0, 1, 2, 3 and 4, and y is selected from the group consisting of 1, 2, 3, 4, 5, 6, 7, 8, 9, 10, 11 and 12, C is selected from the group consisting of

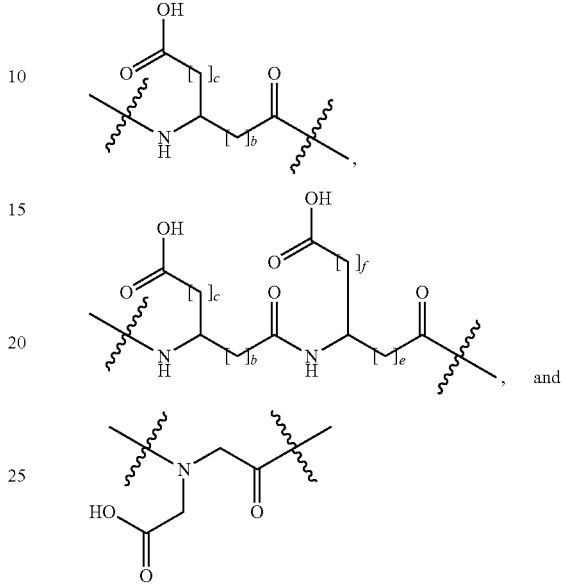

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and D is selected from the group consisting of

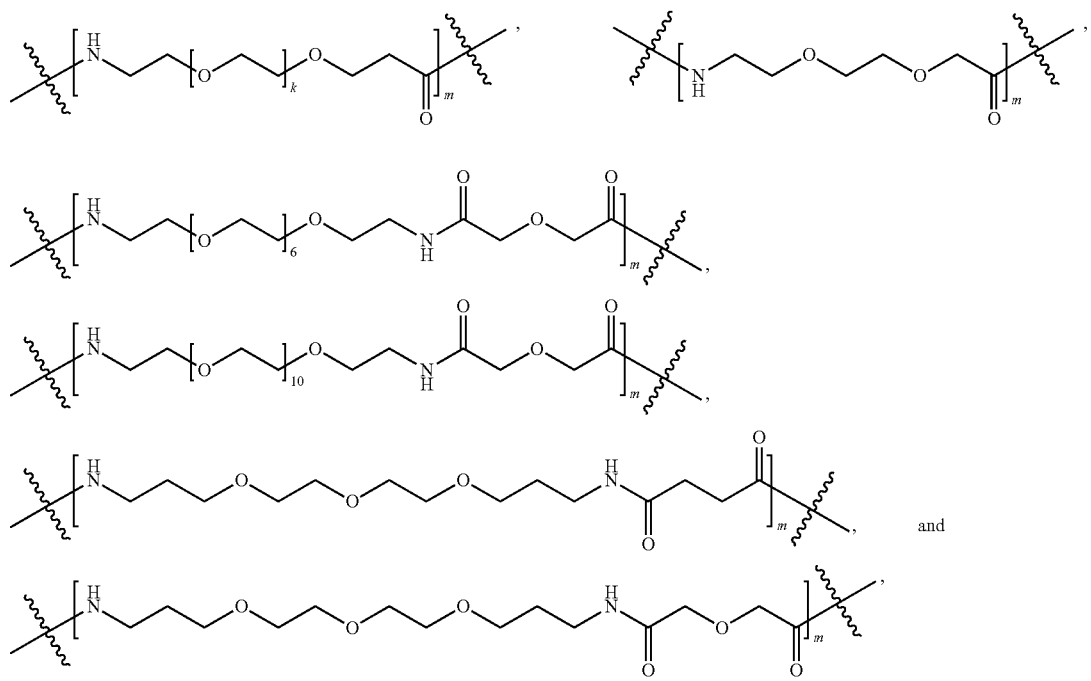

and wherein k is selected from the group consisting of 0, 1, 2, 3, 4, 5, 11 and 27, and m is selected from the group consisting of 0, 1, 2, 3, 4, 5 and 6.

In one aspect of the invention the fragments A-OH, A-C-D-OH, A-B—C—OH or A-B—C-D-OH used in the acylation of the ε-N of a lysine moiety are carboxylic acid derivatives that are activated to activated acylating agents as described above.

In one aspect of the invention a free functional chemical group, such as a contained carboxylic acid in fragment A or C of the fragments A-OH, A-C-D-OH, A-B—C—OH or A-B—C-D-OH is protected with an appropriate protecting group selected from but not limited to tert-butyl, benzyl or allyl.

When used herein the term "contained" in connection with a peptide and/or an acylating agent about a functional chemical group, such as a carboxylic acid, shall mean a functional chemical group present in the peptide or acylating agent.

The carboxylic acid derivatives may efficiently be prepared on a resin such as 2-chlorotritylchloride resin via an Fmoc based strategy using adequately protected building blocks using the reaction conditions described in (Fmoc Solid Phase Peptide Synthesis, Edited by W. C. Chan and P. D. White, Oxford University Press, 2000, ISBN 0-19-963724-5).

An example of a fragment A-B—C-D-OH is:

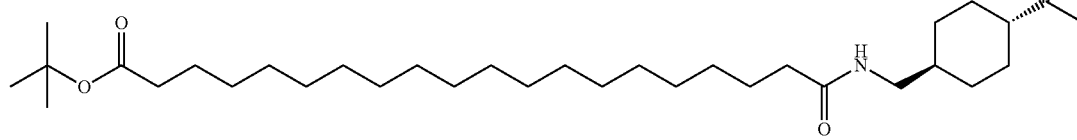

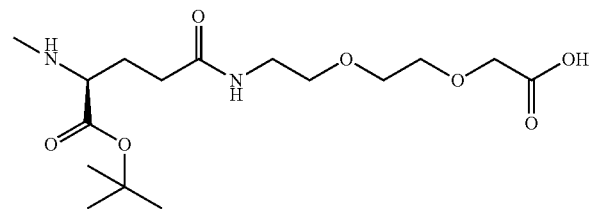

The corresponding activated analogue could be the N-hydroxysuccinimide ester;

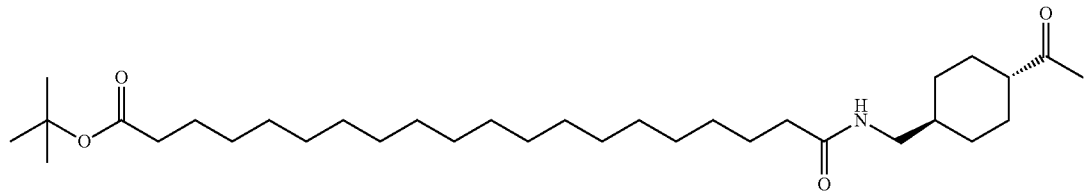

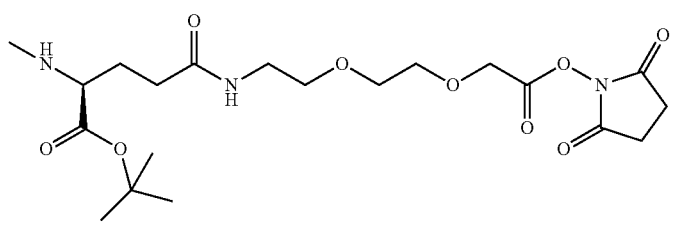

Examples of fragments A-B—C-D-:

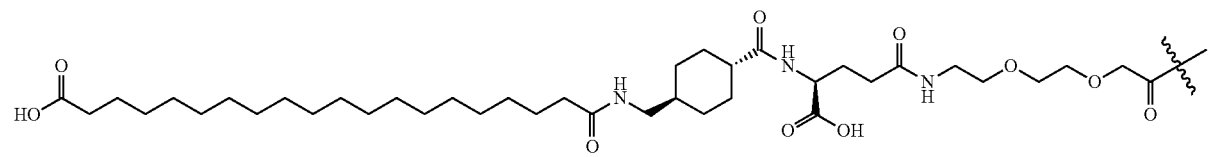

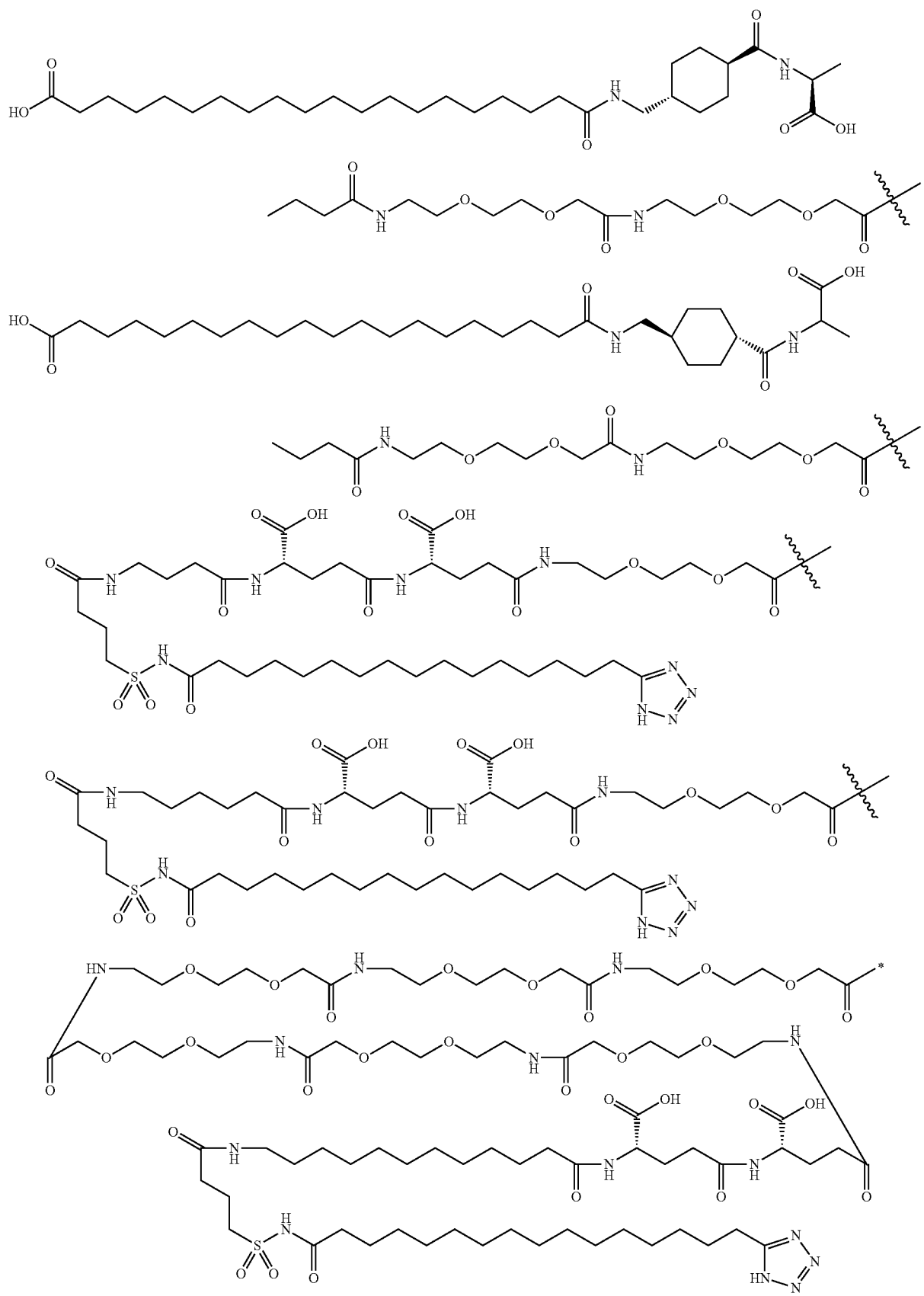

-continued
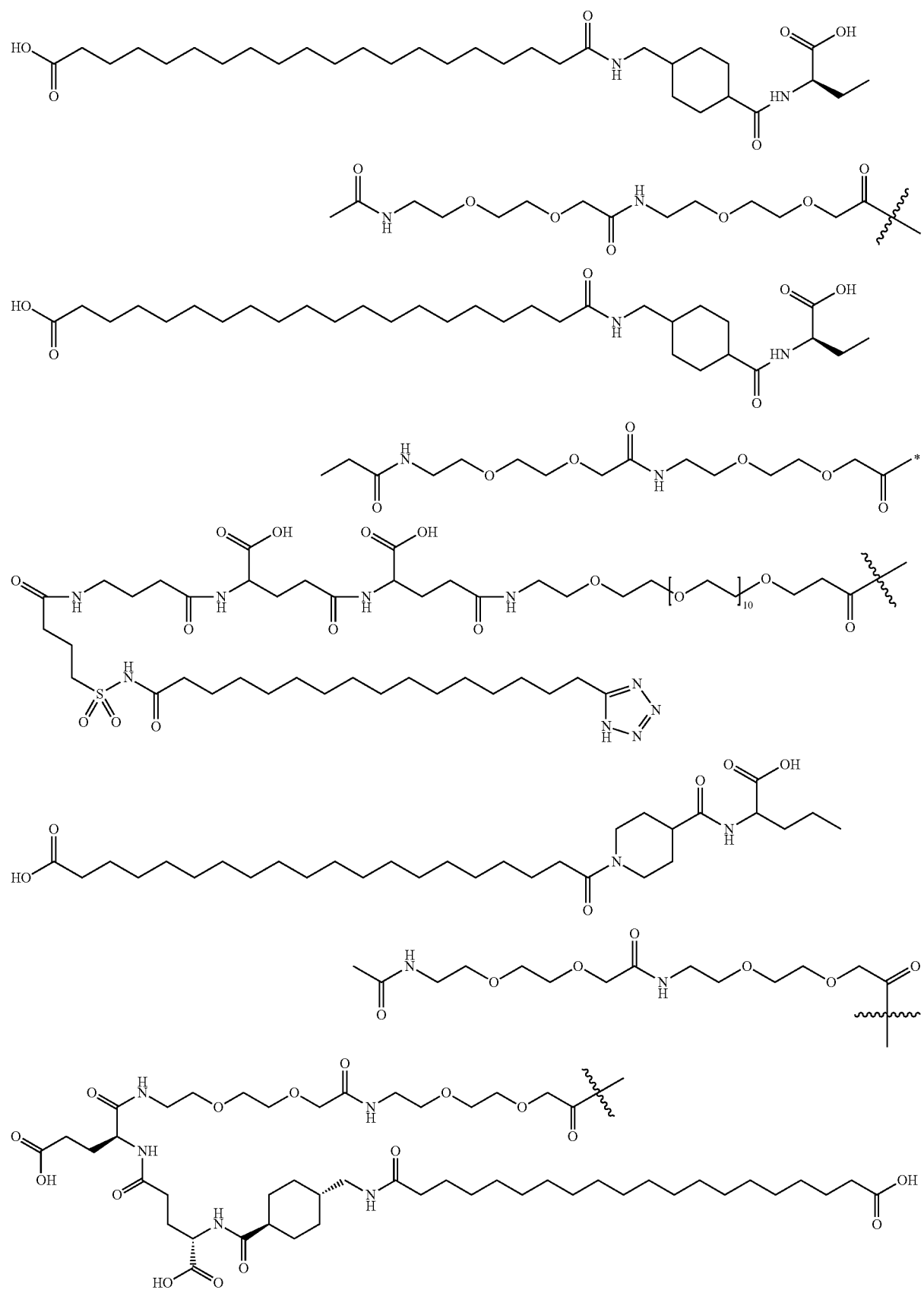

Examples of fragments A-C-D-:
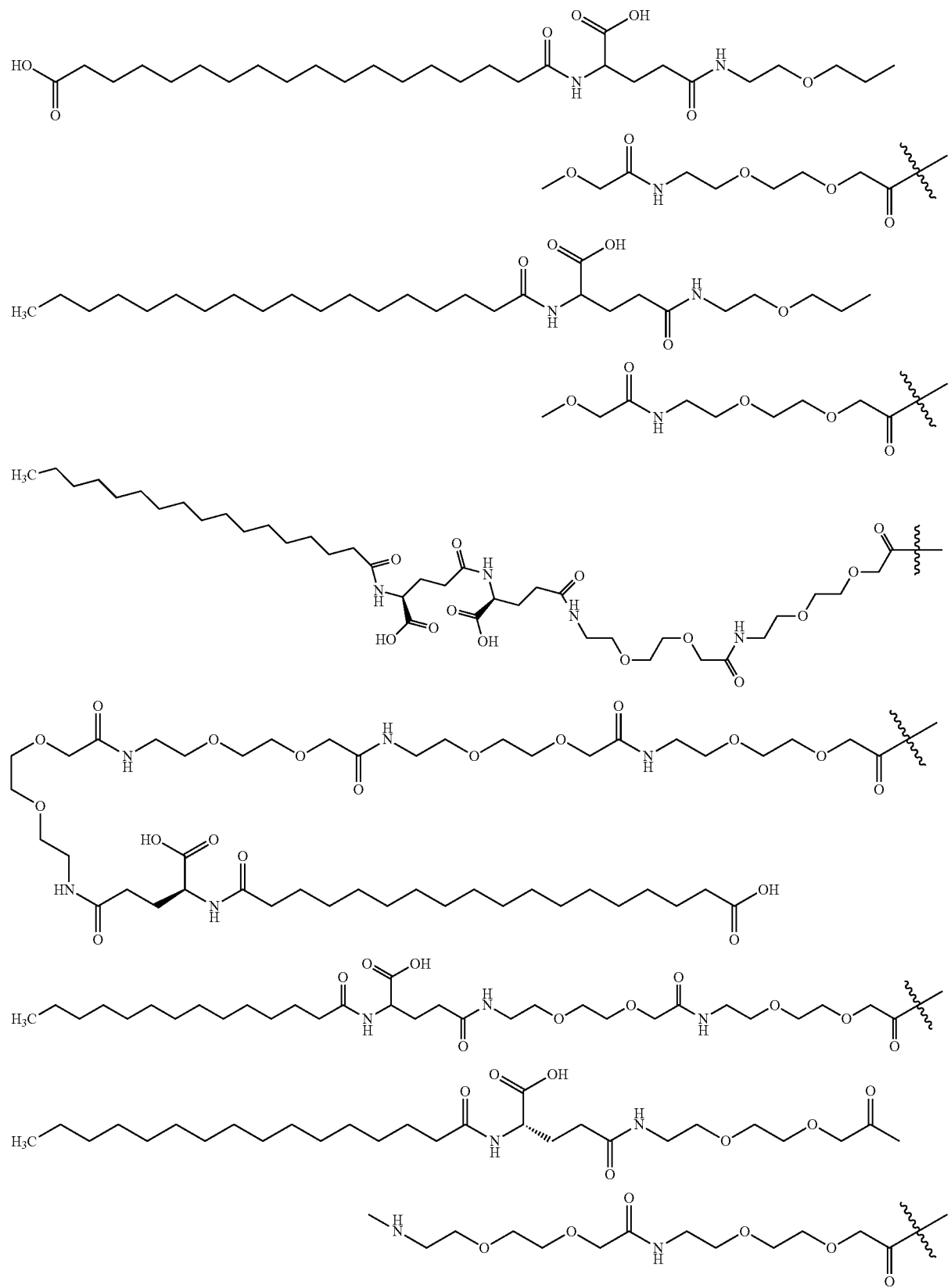

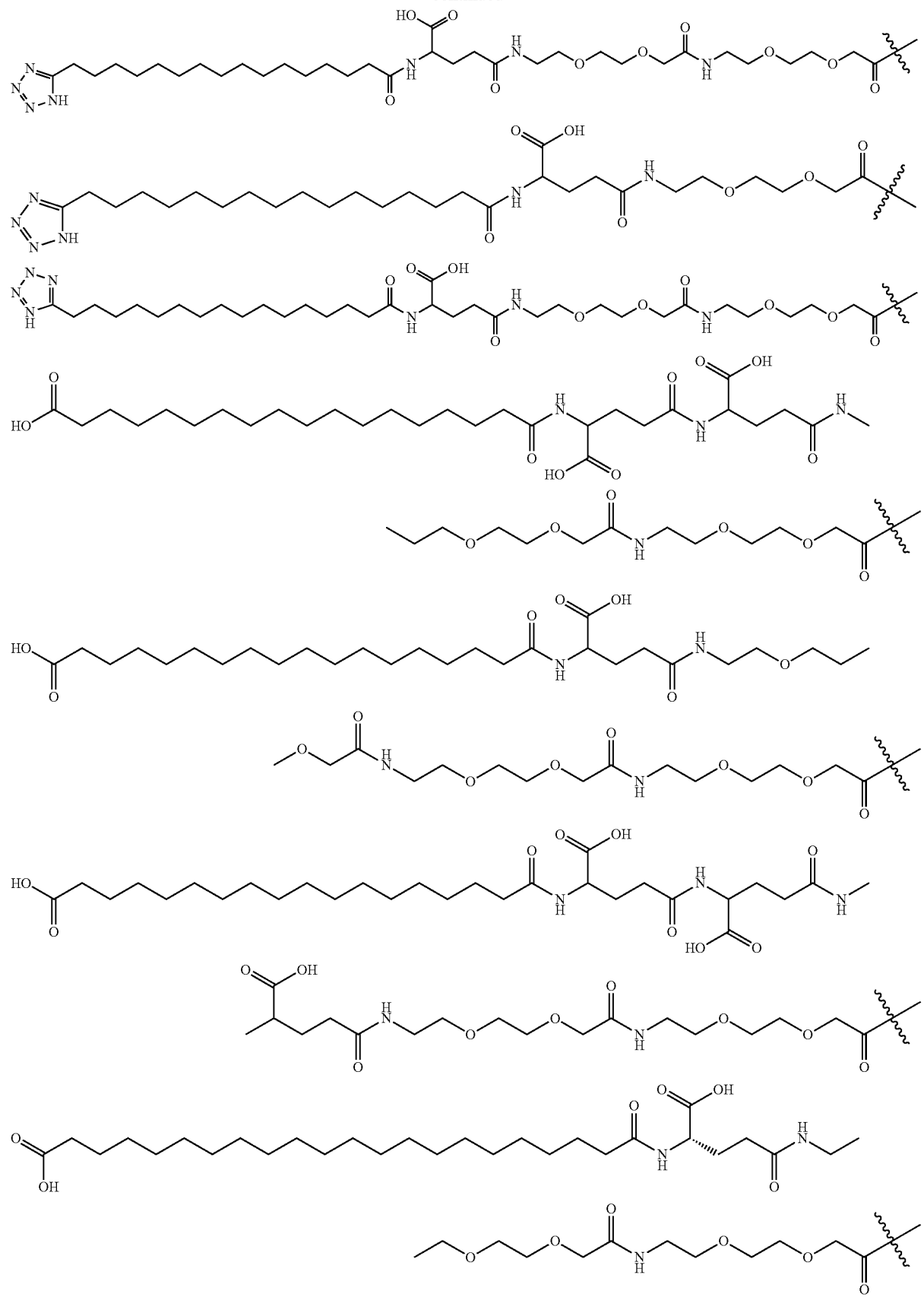

Examples of fragments A-B—C—:

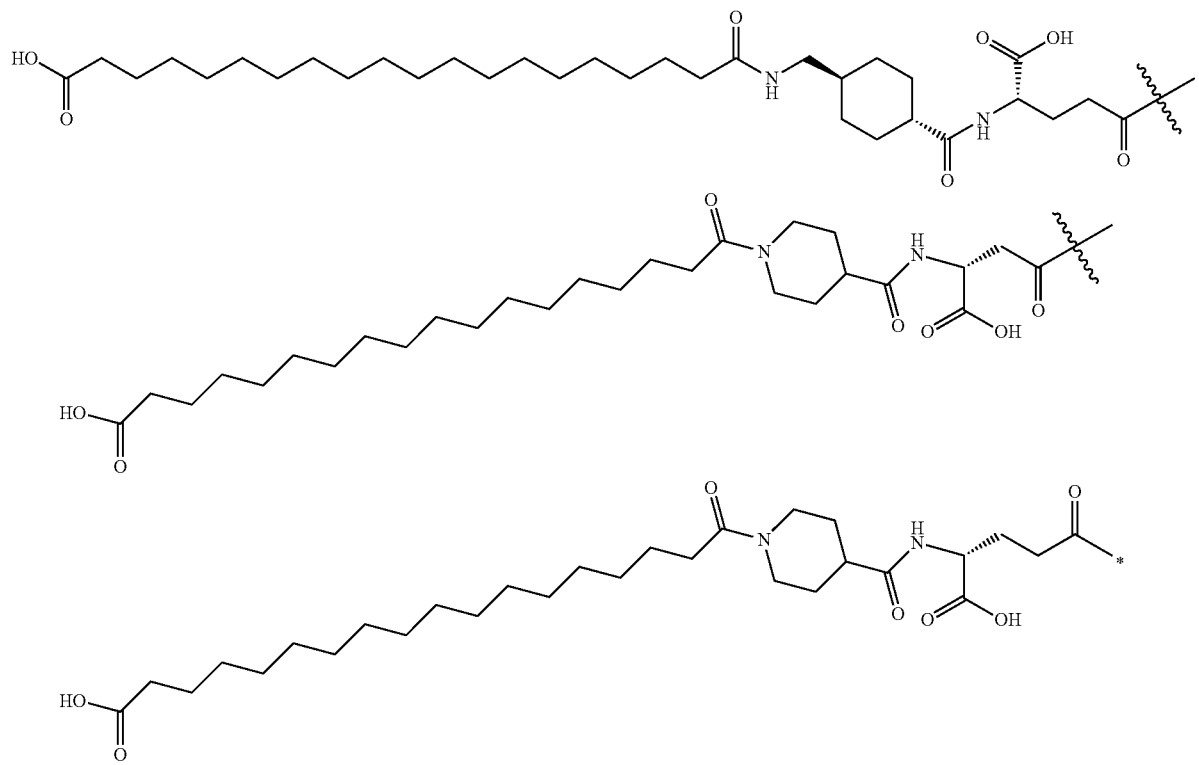

In all the specific mentioned fragments A-OH, A-C-D-OH, A-B—C—OH or A-B—C-D-OH any contained free carboxylic acid(s), may optionally be protected with an appropriate protecting group selected from but not limited to tert-butyl, benzyl or allyl.

In all the specific mentioned fragments A-OH, A-C-D-OH, A-B—C—OH or A-B—C-D-OH the chiral centers whether specified or not may be either the R or S enantiomer independent of other chiral centers in the same fragment.

In one embodiment, when one or more chiral centers are present, the fragments may be in the form of a mixture of enantiomers.

In another embodiment, when one or more chiral centers are present, the fragments may be in the form of a pure enantiomer, wherein each of the chiral centers are either R or S.

In another embodiment, the chirality is as depicted in the specifically mentioned fragments of the present invention.

In one aspect of the invention the epsilon amine protection group of a lysine amino acid residue may be selected from, but is not limited to, the following examples:

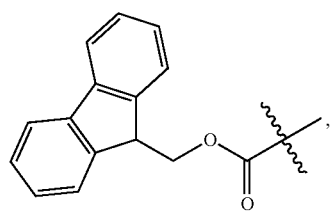

-continued

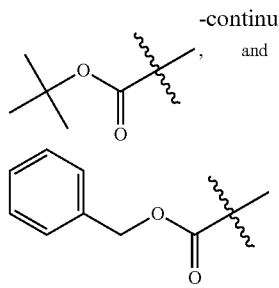

and

In the method according to the invention, the acylation step may in certain useful embodiments take place in a solvent, including an organic polar solvent selected from 1-methyl-pyrrolidin-2-one, acetonitril, tetrahydrofuran, dimethylsulfoxide, N,N-dimethylformamide and N-methylformamide.

In a further embodiment, the acylation step may take place in an aqueous solvent mixture, such as an aqueous solvent mixture comprising an organic polar solvent. Such organic polar solvent may advantageously be selected from 1-methyl-pyrrolidin-2-one, acetonitril, tetrahydrofuran, dimethylsulfoxide, N,N-dimethylformamide and N-methylformamide.

In a further embodiment, the acylation step may take place in aqueous solution.

The amount of 1-methyl-pyrrolidin-2-one, acetonitril, tetrahydrofuran, dimethylsulfoxide and N,N-dimethylformamide or N-methyl-formamide may in certain embodiments be such that the amount of said solvent is less than 80% (v/v), such as less than 50% (v/v). In other aspects the amount of 1-methyl-pyrrolidin-2-one, acetonitril, tetrahydrofuran, dimethylsulfoxide, N,N-dimethylformamide or N-methyl-formamide is in the range of about 40-80% (v/v), including the range of 40-45, 45-50, 50-60, 60-70 and 70-80% (v/v). It is furthermore contemplated that the acylating agent may be added to the reaction mixture as a solid.

The pH value of the aqueous solvent reaction mixture wherein the acylation step takes place, is in useful embodiments between 9 and 13, such as between 10 and 12, including between 10.5 and 11.5. In further embodiments the pH in the reaction mixture is in the range of 9-10, 10-11, 11-12 or 12-13.

The acylating agent used in accordance with the invention, may comprise one or more protection groups. Hence, it is contemplated that the method according to the invention may further comprise one or more steps of removing one or more of these protection groups from the acylating agent once it has been coupled to the GLP-1 analogue precursor molecule. Such deprotection steps are well described in the literature.

Efficient heterologous protein expression in host cells, often require that the protein is expressed in the form of a pro-peptide, i.e. a polypeptide having a secretory signal sequence (also known as a leader sequence, prepro sequence or pre sequence). However, this leader sequence is normally not wanted in the desired polypeptide, and therefore the method according to the invention may in certain aspects include a further step of removing N-terminal and/or C-terminal pro-peptide extensions from the GLP-1 analogue precursor molecule.

The method according to the invention comprises a step of isolating the resulting GLP-1 analogue or derivative by suitable means, e.g. standard purification methods known in the art.

It is also within the scope of the invention that the GLP-1 analogues or derivatives resulting from the method according to the invention in certain embodiments may be derivatized with an albumin binding moiety or be pegylated.

The leader sequences of the present invention may be in the optimized form as listed in FIG. 4.

The term "albumin binding moiety" as used herein means a residue which binds non-covalently to human serum albumin. The albumin binding residue attached to the therapeutic polypeptide typically has an affinity below 10 µM to human serum albumin and preferably below 1 µM. A range of albumin binding residues are known among linear and branched lipohophillic moieties containing 4-40 carbon atoms having a distal acidic group.

Embodiments According To The Invention

1. A method for making a GLP-1 analogue or derivative comprising one or more non-proteogenic amino acids in the N-terminal part, said method comprising the steps of
(i) culturing a host cell comprising a nucleotide sequence encoding a precursor molecule of said GLP-1 analogue under suitable conditions for expression of said precursor molecule,
(ii) separating the expressed precursor molecule from the culture broth,
(iii) coupling an N-terminal amino acid extension comprising one or more non-proteogenic amino acids to the expressed precursor molecule,
(iv) isolating the resulting GLP-1 analogue or derivative by suitable means.

2. A method for making a GLP-1 analogue or derivative comprising one or more non-proteogenic amino acids in the N-terminal part, said method comprising the steps of:
i) culturing a host cell comprising a nucleotide sequence encoding a precursor molecule of said GLP-1 analogue under suitable conditions for expression of said precursor molecule,
ii) separating the expressed precursor molecule from the culture broth,
iii) protecting the lysine group(s) of the precursor molecule,
iv) coupling an N-terminal amino acid extension comprising one or more non-proteogenic amino acids to the protected precursor molecule, to obtain a protected GLP-1 analogue,
v) deprotecting the lysine group(s) of the said protected GLP-1 analogue,
vi) isolating the resulting GLP-1 analogue or derivative by suitable means.

3. A method according to embodiments 1 or 2, wherein the N-terminal amino acid extension is protected before its use in the coupling step, where an N-terminal amino acid extension comprising one or more non-proteogenic amino acids is coupled to the protected precursor molecule, and wherein the protected GLP-1 analogue is deprotected again after coupling of the N-terminal extension.

4. A method for making a GLP-1 analogue or derivative comprising one or more non-proteogenic amino acids in the N-terminal part, said method comprising the steps of:
i) culturing a host cell comprising a nucleotide sequence encoding a precursor molecule of said GLP-1 analogue under suitable conditions for expression of said precursor molecule,
ii) separating the expressed precursor molecule from the culture broth,
iii) coupling a protected N-terminal amino acid extension comprising one or more non-proteogenic amino acids to the expressed precursor molecule,
iv) deprotecting any protecting group of the protected GLP-1 analogue or derivative,
v) isolating the resulting GLP-1 analogue or derivative by suitable means.

5. A method for making a GLP-1 analogue or derivative comprising one or more non-proteogenic amino acids in the N-terminal part, said method comprising the steps of:
i) culturing a host cell comprising a nucleotide sequence encoding a precursor molecule of said GLP-1 analogue under suitable conditions for expression of said precursor molecule,
ii) separating the expressed precursor molecule from the culture broth,
iii) protecting the lysine group(s) of the precursor molecule,
iv) coupling a protected N-terminal amino acid extension comprising one or more non-proteogenic amino acids to the protected precursor molecule, to obtain a protected GLP-1 analogue or derivative,
v) deprotecting any protecting group of the protected GLP-1 analogue or derivative,
vi) isolating the resulting GLP-1 analogue or derivative by suitable means.

6. A method according to any of the previous embodiments, wherein the precursor molecule of said GLP-1 analogue is selected from the list of precursor molecules comprising the amino acid sequence of the general formula:

(SEQ ID NO: 3)
Thr-Phe-Thr-Ser-Asp-Xaa$_{16}$-Ser-Xaa$_{18}$-Xaa$_{19}$-Xaa$_{20}$-

Glu-Xaa$_{22}$-Xaa$_{23}$-Ala-Xaa$_{25}$-Xaa$_{26}$-Xaa$_{27}$-Phe-Ile-

-continued
```
Xaa30-Trp-Leu-Xaa33-Xaa34-Xaa35-Xaa36-Xaa37-Xaa38-

Xaa39-Xaa40-Xaa41-Xaa42-Xaa43-Xaa44-Xaa45
```
wherein
Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly or Glu;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val, Lys or Arg;
Xaa$_{34}$ is Lys, Glu, Asn, His or Arg;
Xaa$_{35}$ is Gly;
Xaa$_{36}$ is Arg, Gly or Lys;
Xaa$_{37}$ is Gly, Ala, Glu, Pro, Lys, or is absent;
Xaa$_{38}$ is Lys, Ser, or is absent.
Xaa$_{39}$ is Ser, Lys, or is absent;
Xaa$_{40}$ is Gly, or is absent;
Xaa$_{41}$ is Ala, or is absent;
Xaa$_{42}$ is Pro, or is absent;
Xaa$_{43}$ is Pro, or is absent;
Xaa$_{44}$ is Pro, or is absent;
Xaa$_{45}$ is Ser, or is absent;
provided that if Xaa$_{38}$, Xaa$_{39}$, Xaa$_{40}$, Xaa$_{41}$, Xaa$_{42}$, Xaa$_{43}$, Xaa$_{44}$ or Xaa$_{45}$ is absent then each amino acid residue downstream is also absent.

7. A method according to any of embodiments 1-5, wherein the precursor molecule of said GLP-1 analogue is selected from the list of precursor molecules comprising the amino acid sequence of the general formula:

```
                                           (SEQ ID NO: 4)
Xaa9-Xaa10-Thr-Phe-Thr-Ser-Asp-Xaa16-Ser-Xaa18-

Xaa19-Xaa20-Glu-Xaa22-Xaa23-Ala-Xaa25-Xaa26-

Xaa27-Phe-Ile-Xaa30-Trp-Leu-Xaa33-Xaa34-Xaa35-

Xaa36-Xaa37-Xaa38-Xaa39-Xaa40-Xaa41-Xaa42-Xaa43-

Xaa44-Xaa45
```
wherein
Xaa$_9$ is Glu or Asp
Xaa$_{10}$ is Gly or Ala
Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly or Glu;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val, Lys or Arg;
Xaa$_{34}$ is Lys, Glu, Asn, His or Arg;
Xaa$_{35}$ is Gly;
Xaa$_{36}$ is Arg, Gly or Lys;
Xaa$_{37}$ is Gly, Ala, Glu, Pro, Lys, or is absent;
Xaa$_{38}$ is Lys, Ser, or is absent.
Xaa$_{39}$ is Ser, Lys, or is absent;
Xaa$_{40}$ is Gly, or is absent;
Xaa$_{41}$ is Ala, or is absent;
Xaa$_{42}$ is Pro, or is absent;
Xaa$_{43}$ is Pro, or is absent;
Xaa$_{44}$ is Pro, or is absent;
Xaa$_{45}$ is Ser, or is absent;
provided that if Xaa$_{38}$, Xaa$_{39}$, Xaa$_{40}$, Xaa$_{41}$, Xaa$_{42}$, Xaa$_{43}$, Xaa$_{44}$ or Xaa$_{45}$ is absent then each amino acid residue downstream is also absent.

8. A method according to any of embodiments 1-5, wherein the precursor molecule of said GLP-1 analogue is selected from the list of precursor molecules comprising the amino acid sequence of the general formula:

```
                                           (SEQ ID NO: 5)
Xaa8-Xaa9-Xaa10-Thr-Phe-Thr-Ser-Asp-Xaa16-Ser-

Xaa18-Xaa19-Xaa20-Glu-Xaa22-Xaa23-Ala-Xaa25-Xaa26-

Xaa27-Phe-Ile-Xaa30-Trp-Leu-Xaa33-Xaa34-Xaa35-

Xaa36-Xaa37-Xaa38-Xaa39-Xaa40-Xaa41-Xaa42-Xaa43-

Xaa44-Xaa45
```
wherein
Xaa$_8$ is Ala, Gly, Val, Leu, Ile, Lys
Xaa$_9$ is Glu, Asp
Xaa$_{10}$ is Gly, Ala
Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly or Glu;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val, Lys or Arg;
Xaa$_{34}$ is Lys, Glu, Asn, His or Arg;
Xaa$_{35}$ is Gly;
Xaa$_{36}$ is Arg, Gly or Lys;
Xaa$_{37}$ is Gly, Ala, Glu, Pro, Lys, or is absent;
Xaa$_{38}$ is Lys, Ser, or is absent.
Xaa$_{39}$ is Ser, Lys, or is absent;
Xaa$_{40}$ is Gly, or is absent;
Xaa$_{41}$ is Ala, or is absent;
Xaa$_{42}$ is Pro, or is absent;
Xaa$_{43}$ is Pro, or is absent;
Xaa$_{44}$ is Pro, or is absent;
Xaa$_{45}$ is Ser, or is absent;
provided that if Xaa$_{38}$, Xaa$_{39}$, Xaa$_{40}$, Xaa$_{41}$, Xaa$_{42}$, Xaa$_{43}$, Xaa$_{44}$ or Xaa$_{45}$ is absent then each amino acid residue downstream is also absent.

9. A method according to any of the previous embodiments, wherein the non-proteogenic amino acids in the N-terminal amino acid extension comprising one or more non-proteogenic amino acids, are selected from the group consisting of γ-carboxyglutamate, ornithine, phosphoserine, D-amino acids such as D-alanine and D-glutamine, D-alanine and D-leucine, Aib (α-aminoisobutyric acid), Abu α-aminobutyric acid), Tle (tert-butylglycine), 3-aminomethyl benzoic acid, anthranilic acid, des-amino-Histidine, β-alanine, D-histidine, desamino-histidine, 2-amino-histidine, β-hydroxy-histidine, homohistidine, Nα-acetyl-histidine, α-fluoromethyl-histidine, α-methyl-histidine, 3-pyridylalanine, 2-pyridylalanine, 4-pyridylalanine, (1-aminocyclopropyl) carboxylic acid, (1-aminocyclobutyl)

carboxylic acid, (1-aminocyclopentyl) carboxylic acid, (1-aminocyclohexyl) carboxylic acid, (1-aminocycloheptyl) carboxylic acid, (1-aminocyclooctyl) carboxylic acid, α-methyl prolin, 1-methyl histidine, 3-methyl histidine, and 4,5,6,7-tetrahydro-1H-imidazo[4,5-C]pyridine-6-carboxylic acid β-(1,2,4-triazol-1-yl)-alanine.

10. A method according to any of the previous embodiments, wherein the length of the N-terminal amino acid extension comprising one or more non-proteogenic amino acids is 1 amino acid.

11. A method according to any of embodiments 1-9, wherein the length of the N-terminal amino acid extension comprising one or more non-proteogenic amino acids is 2 amino acids.

12. A method according to any of embodiments 1-9, wherein the length of the N-terminal amino acid extension comprising one or more non-proteogenic amino acids is 3 amino acids.

13. A method according to any of embodiments 1-9, wherein the length of the N-terminal amino acid extension comprising one or more non-proteogenic amino acids is 4 amino acids.

14. A method according to any of the previous embodiments, wherein the N-terminal amino acid extension comprises two non-proteogenic amino acids.

15. A method according to any of embodiments 1-13, wherein the N-terminal amino acid extension comprises three non-proteogenic amino acids.

16. A method according to any of embodiments 1-13, wherein the N-terminal amino acid extension comprises four non-proteogenic amino acids.

17. A method according to any of the previous embodiments, wherein the N-terminal amino acid extension comprising one or more non-proteogenic amino acids has the general formula $Xaa_7$-$Xaa_8$-$Xaa_9$-$Xaa_{10}$ wherein $Xaa_7$ is selected from L-histidine, D-histidine, desamino-histidine, 2-amino-histidine, β-hydroxy-histidine, homo-histidine, $N^\alpha$-acetyl-histidine, α-fluoromethyl-histidine, α-methyl-histidine, 3-pyridylalanine, 2-pyridylalanine and 4-pyridylalanine, 1-methyl histidine, 3-methyl histidine, and 4,5,6,7-tetrahydro-1H-imidazo[4,5-C]pyridine-6-carboxylic acid β-(1,2,4-triazol-1-yl)-alanine $Xaa_8$ is selected from Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid and alpha-methyl proline $Xaa_9$ is selected from Glu, Asp, γ,γ-dimethyl Glu, β,β-dimethyl Glu and β,β-dimethyl Asp, and $Xaa_{10}$ is selected from Gly, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, and (1-aminocyclooctyl) carboxylic acid.

18. A method according to any of embodiments 1-16, wherein the N-terminal amino acid extension comprising one or more non-proteogenic amino acids has the general formula $Xaa_7$-$Xaa_8$ wherein $Xaa_7$ is selected from L-histidine, D-histidine, desamino-histidine, 2-amino-histidine, β-hydroxy-histidine, homo-histidine, $N^\alpha$-acetyl-histidine, α-fluoromethyl-histidine, α-methyl-histidine, 3-pyridylalanine, 2-pyridylalanine and 4-pyridylalanine; 1-methyl histidine, 3-methyl histidine, 4,5,6,7-tetrahydro-1H-imidazo[4,5-C]pyridine-6-carboxylic acid β-(1,2,4-triazol-1-yl)-alanine; and $Xaa_8$ is selected from Gly, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid and alpha-methyl proline 19. A method according to any of embodiments 1-16, wherein the N-terminal amino acid extension comprising one non-proteogenic amino acid having the general formula $Xaa_7$ wherein $Xaa_7$ is selected from D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine and 4-pyridylalanine; 1-methyl histidine, 3-methyl histidine, and 4,5,6,7-tetrahydro-1H-imidazo[4,5-C]pyridine-6-carboxylic acid β-(1,2,4-triazol-1-yl)-alanine.

20. A method according to embodiment 19, wherein the N-terminal amino acid extension is desamino-histidine and the coupling reaction is carried out by a 4-[2-(2,5-dioxo-pyrrolidin-1-yloxycarbonyl)-ethyl]-1H-imidazol-1-ium salt, such as trifluoroacetate, with the expressed precursor molecule.

21. A method according to any of embodiments 1-5, wherein the N-terminal amino acid extension comprising one or more non-proteogenic amino acids has the general formula $Xaa_7$-$Xaa_8$-$Xaa_9$-$Xaa_{10}$ as defined in embodiment 17;

and the GLP-1 analogue has the general formula

Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-Trp-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$-$Xaa_{44}$-$Xaa_{45}$ (SEQ ID NO: 3) as defined in embodiment 3.

22. A method according to any of embodiments 1-5, wherein the N-terminal amino acid extension comprising one or more non-proteogenic amino acids has the general formula $Xaa_7$-$Xaa_8$ as defined in embodiment 18;

and the GLP-1 analogue has the general formula $Xaa_9$- $Xaa_{10}$-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-Trp-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$-$Xaa_{44}$-$Xaa_{45}$ (SEQ ID NO: 4) as defined in embodiment 4.

23. A method according to any of embodiments 1-5, wherein the N-terminal amino acid extension comprising one or more non-proteogenic amino acids has the general formula $Xaa_7$ as defined in embodiment 19;

and the GLP-1 analogue has the general formula $Xaa_8$- $Xaa_9$- $Xaa_{10}$-Thr-Phe-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-Trp-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$-$Xaa_{43}$-$Xaa_{44}$-$Xaa_{45}$ (SEQ ID NO: 5) as defined in embodiment 4.

24. A method according to any of embodiments 17-23, wherein the C-terminal non-proteogenic or proteogenic amino acid in the N-terminal extensions Xaa$_7$-Xaa$_8$-Xaa$_9$-Xaa$_{10}$ or Xaa$_7$-Xaa$_8$, or the non-proteogenic amino acid Xaa$_7$ is activated.

25. A method according to embodiment 24, wherein the activated amino acid(s) are selected from the group consisting of: acid chloride, acid bromide, acid fluoride, symmetrical anhydride, mixed anhydride, carboxylic acids activated using common carbodiimides, carboxylic acids using carbodiimides and an additive and carboxylic acids activated with an uronium salt or a phosphonium salt.

26. A method according to embodiment 24, wherein the activated amino acid(s) are selected from the group consisting of: carboxylic acids activated using common carbodiimides, diisopropylcarbodiimide (DIPCDI), N,N'-dicyclohexylcarbodiimide (DCC), 1-ethyl-3-(3'-dimethylaminopropyl)-carbodiimide hydrochloride (EDC).

27. A method according to embodiment 24, wherein the activated amino acid(s) are selected from the group consisting of: carboxylic acids using carbodiimides and an additive selected from the group consisting of N-hydroxybenzotriazol (HOBt), 1-Hydroxy-7-azabenzotriazole, 6-chloro-N-hydroxybenzotriazol (HOAt) and 3-Hydroxy-3,4-dihydro-4-oxo-1,2,3-benzotriazine (DhbtOH), 28. A method according to embodiment 24, wherein the activated amino acid(s) are selected from the group consisting of: carboxylic acids activated with an uronium salt or a phosphonium salt, O-Benzotriazole-N,N,N',N'-tetramethyl-uronium-hexafluoro-phosphate (HBTU), O-(Benzotriazol-1-yl)-N,N,N',N'-tetramethyluronium tetrafluoroborate (TBTU), 2-(1H-7-Azabenzotriazol-1-yl)-1,1,3,3-tetramethyl uronium hexafluorophosphate (HATU), 1-benzotriazolyoxytris(dimethylamino)phosphonium hexafluorophosphate (BOP) benzotriazol-1-yl-oxytripyrrolidinophosphonium hexafluorophosphate (PYBOP), esters of N-hydroxysuccinimid (NHS ester), pentafluorophenol ester (PfP-ester), 2,4-dinitrophenyl ester, 4-nitrophenyl ester, 3-Hydroxy-3,4-dihydro-4-oxo-1,2,3-benzotriazine (HODhbt) Carbonyldiimidazole (CDI), N-ethyl-5-phenylisoxazolium-3'-sulfonate (NEPIS).

29. A method according to any of the previous embodiments, wherein the coupling of the N-terminal amino acid extension comprising one or more non-proteogenic amino acids takes place in an organic polar solvent selected from the group consisting of 1-methyl-pyrrolidin-2-one, acetonitril, tetrahydrofuran, dimethylsulfoxide N,N-dimethylformamide and N-methyl-formamide.

30. A method according to any of the previous embodiments, wherein the coupling of the N-terminal amino acid extension comprising one or more non-proteogenic amino acids takes place in an aqueous solvent mixture.

31. A method according to embodiment 30, wherein the aqueous solvent mixture comprises an organic polar solvent selected from the group consisting of 1-methyl-pyrrolidin-2-one, acetonitril, tetrahydrofuran, dimethylsulfoxide N,N-dimethylformamide and N-methyl-formamide.

32. A method according to embodiments 30 or 31, wherein the coupling of the N-terminal amino acid extension comprising one or more non-proteogenic amino acids takes place in an aqueous solvent mixture, wherein the pH in the reaction mixture is between 4 and 12, preferably between 6 and 10.

33. A method according to any of the previous embodiments, wherein the amino acids in the N-terminal amino acid extension comprising one or more non-proteogenic amino acids comprises one or more protection groups.

34. A method according to embodiment 33, further comprising the step of removing one or more protection groups from said N-terminal amino acid extension comprising one or more non-proteogenic amino acids.

35. A method according to embodiment 1, further comprising the step of acylating the epsilon-amino-group of at least one lysine residue in the expressed precursor molecule with an acylating agent.

36. A method according to embodiment 35, wherein the acylating agent is a carboxylic acid analogue of the general formula;

A-OH, A-C-D-OH, A-B—C—OH or A-B—C-D-OH which is optionally activated and/or protected with one or more protection group(s), wherein A is selected from the group consisting of;

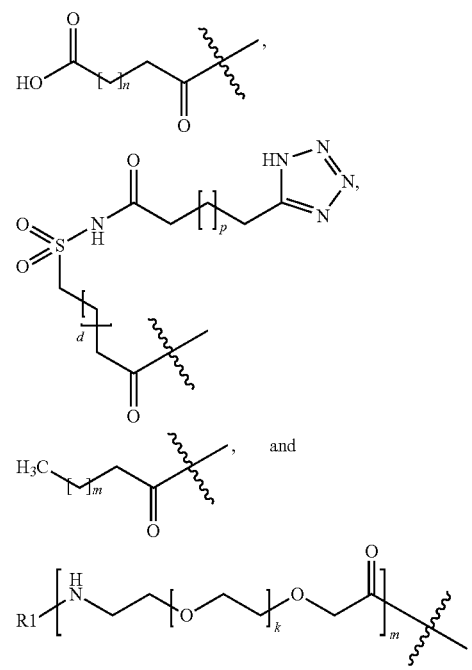

wherein n is selected from the group consisting of 14, 15, 16 17, 18 and 19, p is selected from the group consisting of 10, 11, 12, 13 and 14, and d is selected from the group consisting of 0, 1, 2, 3, 4 and 5, and m is selected from the group consisting of 11, 12, 13, 14, 15, 16, 17, k is selected from the group consisting of 0, 1, 2, 3, 4, 5, 11 and 27, and m is selected from the group consisting of 0, 1, 2, 3, 4, 5 and 6, and R1 is selected from the group of 9H-fluoren-9-yl-methoxycarbonyl (Fmoc), tert-butoxycarbonyl (Boc), Benzylcarbarmate (Cbz).

B is selected from the group consisting of

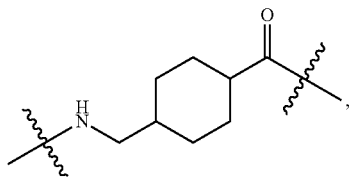

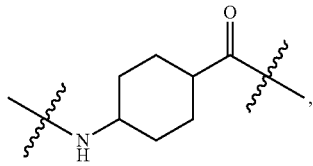

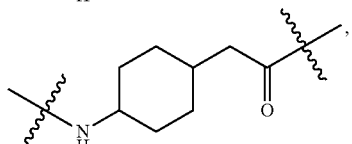

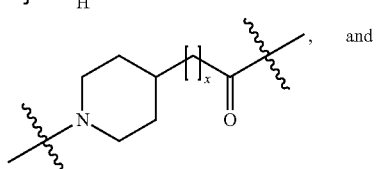, and

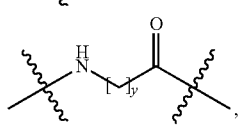, wherein x is selected from the group consisting of 0, 1, 2, 3 and 4, and y is selected from the group consisting of 1, 2, 3, 4, 5, 6, 7, 8, 9, 10, 11 and 12, C is selected from the group consisting of

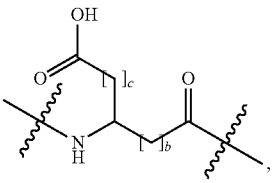,

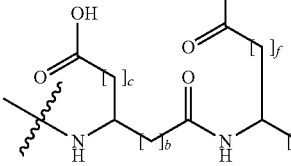 and

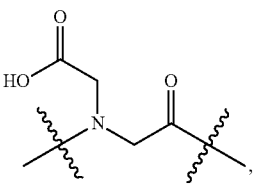, wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2, and D is selected from the group consisting of

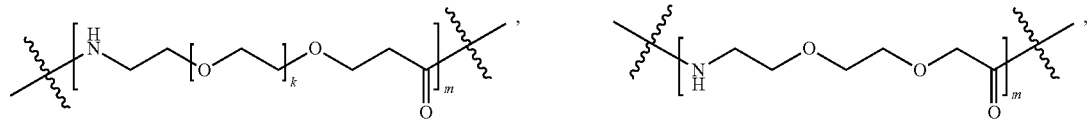

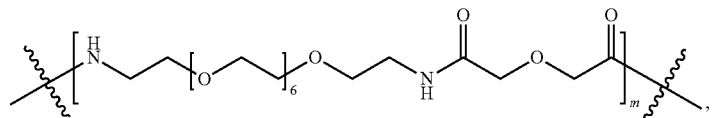

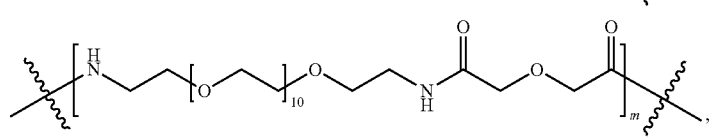

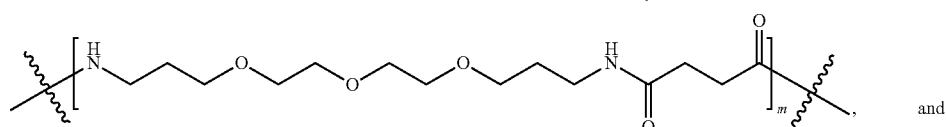, and

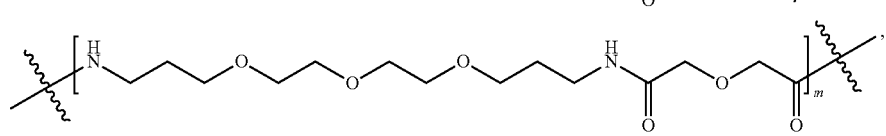

and wherein k is selected from the group consisting of 0, 1, 2, 3, 4, 5, 11 and 27, and m is selected from the group consisting of 0, 1, 2, 3, 4, 5 and 6.

37. A method according to embodiment 36, wherein the carboxylic acid A-OH, A-C-D-OH, A-B—C—OH or A-B—C-D-OH is activated to activated acylating agent.

38. A method according to embodiment 35, wherein said acylation step takes place in an aqueous solvent mixture.

39. A method according to embodiment 38, wherein said aqueous solvent mixture comprises an organic polar solvent.

40. A method according to embodiment 39, wherein said organic polar solvent is selected from the group consisting of 1-methyl-pyrrolidin-2-one, acetonitril, tetrahydrofuran, dimethylsulfoxide, N,N-dimethylformamide and N-methyl-formamide.

41. A method according to embodiment 40, wherein the amount of 1-methyl-pyrrolidin-2-one, acetonitril, tetrahydrofuran, dimethylsulfoxide, N,N-dimethylformamide or N-methyl-formamide is less than 80% (v/v).

42. A method according to embodiment 40, wherein the amount of 1-methyl-pyrrolidin-2-one, acetonitril, tetrahydrofuran, dimethylsulfoxide, N,N-dimethylformamide or N-methyl-formamide is less than 50% (v/v).

43. A method according to embodiment 40, wherein the amount of 1-methyl-pyrrolidin-2-one, acetonitril, tetrahydrofuran, dimethylsulfoxide, N,N-dimethylformamide or N-methyl-formamide is in the range of about 40-80% (v/v).

44. A method according to embodiment 35, wherein the acylating agent is added to the reaction mixture as a solid.

45. A method according to embodiment 35, wherein said acylation step takes place in an aqueous solvent mixture, wherein the pH in the reaction mixture is between 9 and 13, preferably between 10 and 12 or even more preferably between 10.5 and 11.5.

46. A method according to embodiment 35, wherein the acylating agent, which is optionally activated, comprises one or more protection groups.

47. A method according to embodiment 46, further comprising the step of removing one or more protection groups from said activated acylating agent.

48. A method according to any of the previous embodiments, further comprising the step of removing an N-terminal pro-peptide extension from the resulting precursor molecule.

49. A method according to any of embodiments 1-47, further comprising the step of removing a C-terminal pro-peptide extension from the resulting precursor molecule.

50. A method according to any of the previous embodiments, wherein the host cell is a mammalian host cell.

51. A method according to any of embodiments 1-49, wherein the host cell is a bacterial host cell.

52. A method according to any of embodiments 1-49, wherein the host cell is a yeast host cell.

53. A method according to embodiment 52, wherein the yeast host cell is *Saccharomyces cerivisiae*.

54. A method according to any of the previous embodiments, wherein the GLP-1 analogue is an analogue or derivative of human GLP-1(7-37), human GLP-2, exendin-3 or exendin-4.

55. A method according to any of the previous embodiments, wherein the GLP-1 analogue is an analogue or derivative of human GLP-1(7-37).

56. A method according to any of the previous embodiments, wherein said GLP-1 analogue is selected from the group consisting of $Aib^8$-GLP-1(7-36)-amide, $Aib^8$-GLP-1(7-37), $Aib^{8,35}$ GLP-1(7-37), [$Aib^8$,$Arg^{34}$]GLP-1-(7-37), [DesaminoHis$^7$,Glu$^{22}$,Arg$^{26}$,Arg$^{34}$,Lys$^{37}$]GLP-1-(7-37), [DesaminoHis$^7$,Glu$^{22}$,Arg$^{26}$,Arg$^{34}$,Lys$^{37}$]GLP-1-(7-37) amide,
[DesaminoHis$^7$,Arg$^{26}$,Arg$^{34}$,Lys$^{37}$]GLP-1-(7-37)amide,
[DesaminoHis$^7$,Arg$^{26}$,Arg$^{34}$,Lys$^{37}$]GLP-1-(7-37)amide,
[DesaminoHis$^7$,Glu$^{22}$,Arg$^{26}$,Arg$^{34}$,Lys$^{37}$]GLP-1-(7-37),
[DesaminoHis$^7$,Arg$^{26}$,Arg$^{34}$,Lys$^{37}$]GLP-1-(7-37),
[DesaminoHis$^7$,Glu$^{22}$,Arg$^{26}$,Glu$^{30}$,Arg$^{34}$,Lys$^{37}$]GLP-1-(7-37),
[DesaminoHis$^7$,Glu$^{22}$,Arg$^{26}$,Arg$^{34}$,Lys$^{37}$]GLP-1(7-37) amide,
[DesaminoHis$^7$,Arg$^{34}$]GLP-1-(7-37), [$Aib^8$,Glu$^{22}$,Arg$^{26}$,Arg$^{34}$,Lys$^{37}$]GLP-1-(7-37)amide,
[DesaminoHis$^7$, Glu$^{22}$ Arg$^{26}$, Arg$^{34}$, Phe(m-CF3)$^{28}$]GLP-1-(7-37)amide,
[DesaminoHis$^7$,Glu$^{22}$,Arg$^{26}$,Arg$^{34}$]GLP-1-(7-37)-Lys,
[DesaminoHis$^7$,Glu$^{22}$,Arg$^{26}$,Arg$^{34}$]GLP-1-(7-37)-Lys,
[dDesaminoHis$^7$,Arg$^{26}$,Arg$^{34}$,]GLP-1-(7-37)-Lys,
[DesaminoHis$^7$,Glu$^{22}$,Arg$^{26}$,Arg$^{34}$,Lys$^{37}$]GLP-1-(7-37) amide, and analogues thereof.

57. A method according to any of the previous embodiments, wherein the GLP-1 analogue is the only biologically active substance in the pharmaceutical composition.

58. A method according to any of the previous embodiments, wherein the GLP-1 analogue is an exendin-4 analogue.

59. The method according to any of the previous embodiments comprising a step of selectively protecting the epsilon-amino-group of at least one lysine residue.

60. The method according to embodiment 59 wherein the step is added after step (ii) separating the expressed precursor molecule from the culture broth.

61. The method according to embodiment 59 wherein the step is added after step (iv) as defined in embodiment 1 isolating the resulting GLP-1 analogue or derivative by suitable means.

62. The method according to embodiment 19, wherein the N-terminal amino acid is desamino-histidine introduced by the activated acylating agent 4-{3-[(2,5-dioxo-1-pyrrolidinyl)oxy]-3-oxopropyl}-1Himidazol-1-ium

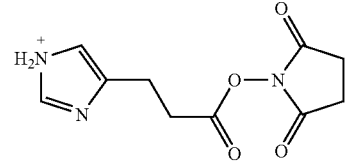 [SMILES: O=C(CCc1c[nH]cn1)ON1C(=O)CCC1=O]

63. The method according to embodiment 19, wherein the N-terminal amino acid is desamino-histidine introduced by the use of the activated acylated agent 4-{3-[(2,5-dioxo-1-pyrrolidinyl)oxy]-3-oxopropyl}-1Himidazol-1-ium trifluoroacetate

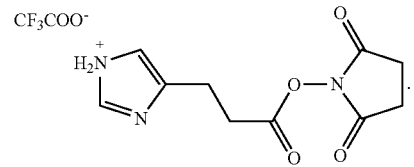 [SMILES: "CF3COO-" ; O=C(CCc1c[nH]cn1)ON1C(=O)CCC1=O]

64. The method according to any of the previous embodiments, wherein the coupling of the N-terminal amino acid extension comprising one or more non-proteogenic amino acids takes place in an organic polar solvent selected from the group consisting of 1-methyl-pyrrolidin-2-one, acetonitril, tetrahydrofuran, dimethylsulfoxide N,N-dimethylformamide and N-methyl-formamide.

65. The method according to any of embodiments 1-63, wherein the coupling of the N-terminal amino acid extension comprising one or more non-proteogenic amino acids takes place in an aqueous solvent mixture.

66. The method according to embodiment 65, wherein the aqueous solvent mixture comprises an organic polar solvent selected from the group consisting of 1-methyl-pyrrolidin-2-one, acetonitril, tetrahydrofuran, dimethylsulfoxide N,N-dimethylformamide and N-methyl-formamide.

67. The method according to any of embodiments 1-63, wherein the coupling of the N-terminal amino acid extension comprising one or more non-proteogenic amino acids takes place in an aqueous solvent mixture, wherein the pH in the reaction mixture is between 7 and 11, preferably between 8 and 10.

68. A method of introducing des-amino histidine in a insulinotropic agent with the use of the activated acylating agent 4-{3-[(2,5-dioxo-1-pyrrolidinyl)oxy]-3-oxopropyl}-1Himidazol-1-ium:

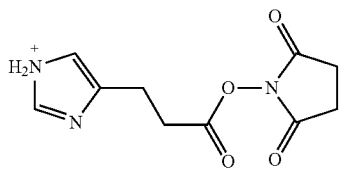 [SMILES: O=C(CCc1c[nH]cn1)ON1C(=O)CCC1=O]

69. A method of introducing des-amino histidine in a insulinotropic agent with the use of the activated acylated agent 4-{3-[(2,5-dioxo-1-pyrrolidinyl)oxy]-3-oxopropyl}-1Himidazol-1-ium trifluoroacetate

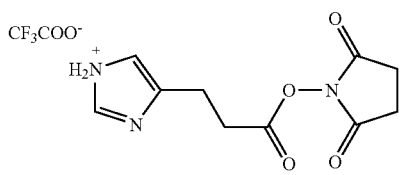 [SMILES: "CF3COO-" ; O=C(CCc1c[nH]cn1)ON1C(=O)CCC1=O]

The present invention will now be described in more details in the following non-limiting Examples and Drawings.

EXAMPLES

Abbreviations Used:
Adoc: adamantyloxycarbonyl
Aib: α-aminoisobutyric acid
Boc: tert butyloxycarbonyl
CH$_3$CN: acetonitrile
DCM: dichloromethane
DIC: Diisopropylcarbodiimide
DIPEA: diisopropylethylamine
DMF: N,N dimethylformamide
EtOAc: Ethylacetate
Et$_2$O: diethylether
Fmoc: 9H-fluoren-9-ylmethoxycarbonyl HATU: 2-(7-azabenzotriazol-1-yl-)-1,1,3,3 tetramethyluronium hexafluorophosphate
HBTU: 2-(1H-Benzotriazol-1-yl-)-1,1,3,3 tetramethyluronium hexafluorophosphate
H$_2$O: water
HOAt: 1-Hydroxy-7-azabenzotriazole
HOBt: 1-Hydroxybenzotriazole
MeCN: acetonitrile
Mtt: 4-Methyltrityl
MW: Molecular weight
NaOH: Sodium hydroxide
NHS: N-Hydroxysuccinimide
NMP: 1-Methyl-pyrrolidin-2-one
OtBu: tert butyl ester
PyBoP (benzotriazol-1-yloxy)tripyrrolidinophosphonium hexafluorophosphate
PyBroP bromo-tris-pyrrolidinophosphonium hexafluorophosphate
r.t: room temperature
OSu: N-Hydroxysuccinimide ester
tBu: tert-butyl
TBME: tert-butylmethylether
TEA: triethylamine
TFA: trifluoroacetic acid
TFFH Tetramethylfluoroformamidinium hexafluorophosphate
TIPS: triisopropylsilane
Trt: Trityl, triphenylmethyl
TSTU: O—(N-succinimidyl)-1,1,3,3-tetramethyluronium tetrafluoroborate
General Methods General Method for the Preparation of Peptides
(Method A)

The peptide can be synthesized according to the Fmoc strategy on an Applied Biosystems 433 peptide synthesizer in 0.25 mmol or 1.0 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methylpyrrolidone), and UV monitoring of the deprotection of the Fmoc protection group. Wang or trityl based resins can be used as solid support and the protected amino acid derivatives used is standard Fmoc-amino acids (supplied from e.g. Anaspec, or Novabiochem) supplied in preweighed cartridges suitable for the ABI433A synthesizer. The N terminal amino acid is Boc protected at the alpha amino group (e.g. Boc-His(Boc) OH is used for peptides with His at the N-terminal). The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2002/2003 or newer version, or W.R. Sampson (1999), J. Pep. Sci. 5, 403.

General Method for the Preparation of Peptides
(Method B)

One alternative method of peptide synthesis is by Fmoc chemistry on a microwave-based Liberty peptide synthesizer (CEM Corp., North Carolina). Wang or trityl based resins can be used as solid support The coupling chemistry is performed with DIC/HOAt in NMP using amino acid solutions of 0.4 M in NMP and a molar excess of 8-10 fold. Coupling conditions is 5 minutes at up to 70° C. Deprotection is achieved with 5% piperidine in NMP at up to 70° C.

The GLP-1 precursor molecules can e.g. be purified by a variety of chromatographic procedures, e.g. ion exchange chromatography, hydrophobic interaction chromatography, gel filtration chromatography, affinity chromatography, reverse phase HPLC or the like, dependent on the type of polypeptide in question.

General Method for the Preparation of Acylating Agents A-OH A-B—C-D-OH, A-C-D-OH, A-B—C—OH and N-Terminal Amino Acid Extensions $Xaa_7$-$Xaa_8$-$Xaa_9$-$Xaa_{10}$, $Xaa_7$-$Xaa_8$ and $Xaa_7$ The necessary carboxylic acids can be prepared on a 2-chlorotritylcloride resin using standard Fmoc chemistry. First Fmoc protected amino carboxylic acid can be attached to the 2-chlorotritylchloride resin by swelling the resin in a suitable solvent like NMP, DCM, DMF or the like, preferably DCM. The adequately protected Fmoc amino carboxylic acid is added together with a suitable base such as DIPEA or TEA, and the resin is agitated for a suitable period of time such as 30 min at r.t. The resin is washed with a suitable solvent such as NMP, DMF or DCM.

Fmoc deprotection is achieved using piperidine in NMP, preferably 20% piperidine in NMP at r.t. for 1 to 30 min, typically 10 min, before the resin is washed thoroughly with NMP, DMF or DCM. The step is repeated until complete deprotection is obtained, typically 3 times or more.

Coupling of the next Fmoc protected amino carboxylic acid is achieved using standard coupling conditions; the resin is swelled in a solvent like NMP, DMF, DCM or a mixture of these. Another solution of Fmoc protected amino carboxylic acid in a solvent like NMP, DMF, DCM or a mixture of these and HOBt or HOAt is added DIC or an equivalent of such. This mixture is added to the resin and the mixture is added DIPEA or TEA and the mixture is agitated at r.t. for 1 to 16 hours typically 3 hours. Alternatively, the mixture is agitated for 1 to 60 min before DIPEA or TEA is added to the mixture. If the coupling is not completed judged by TNBS test, ninhydrine test or choranil test the step is repeated until negative test.

Alternatively activation of the Fmoc protected amino carboxylic acid can be achieved using the following coupling reagents; PyBOP, PyBrOP, HBTU, HATU, or TFFH.

Further incorporation of adequately protected Fmoc-amino carboxylic acids can be introduced using the procedure given above. The last coupling step comprising incorporation of a carboxylic acid derivative is introduced using the coupling conditions described above.

Cleavage from the resin can be achieved by treatment of the resin with 20% trifluoroethanol in DCM, DCM-TIPS-TFA (95.5:2.5:2) or hexafluoroisopropanol from 5 min to 3 hours to give the fully protected derivative.

Cleavage from the resin can also be achieved using TFA-TIPS-Water (95:2.5:2.5) from 5 min to 3 hours to give the fully deprotected derivatives.

Alternatively the derivatives can be prepared in solution using standard procedures described in the literature.

Appropriately protected building blocks are commercially available or can be prepared using procedures described in the literature.

$Xaa_7$ is commercially available or can be prepared via procedures described in the literature.

General Method for Activation of Acylating Agents A-OH A-B—C-D-OH, A-C-D-OH, A-B—C—OH and N-Terminal Amino Acid Extensions $Xaa_7$-$Xaa_8$-$Xaa_9$-$Xaa_{10}$ $Xaa_7$-$Xaa_8$ and $Xaa_7$ Activation of the required amino acids can be achieved using standard procedures described in the literature. If an active ester such as an N-hydroxy succinimid ester is required the carboxylic acid is dissolved in an appropriate solvent such as THF, ethyl acetate, NMP or DMF. A reagent such as O—(N-succinimidyl-)—N,N,N',N'-tetramethyluronium hexafluorophosphate is added to the solution together with a base such as DIPEA or TEA. The mixture is stirred at r.t. until the reaction is complete typically from 3 to 16 hours. Alternatively the carboxylic acid can be dissolved together with N-hydroxy succinimide and treated with DIC. The product mixture can be used directly without further purification or it can be subjected an aqueous work up.

Purification

The crude peptide was purified by preparative HPLC on a column packed with C18 silica. After drying the crude peptide was dissolved in 50% acetic acid in $H_2O$, diluted with $H_2O$ and injected on the column which then was eluted with a gradient of $CH_3CN$ in water and 0.1% TFA 10 ml/min during 50 min at 40° C. The fractions containing the peptide were collected and lyophilized after dilution with water.

Analysis

LCMS

LCMS was performed on a setup consisting of Sciex API 100 Single quadropole mass spectrometer. The instrument control and data acquisition were done by the Sciex Sample control software running on a Windows 2000 computer. The HPLC pump is connected to two eluent reservoirs containing:

A: 0.05% Trifluoro acetic acid in water

B: 0.05% Trifluoro acetic acid in acetonitrile

The analysis was performed at room temperature by injecting an appropriate volume of the sample (preferably 20 μl) onto the column which was eluted with a gradient of acetonitrile.

The HPLC conditions, detector settings and mass spectrometer settings used are giving in the following table:

Column: Waters Xterra MS C-18×3 mm id 5 μm

Gradient: 5%-90% acetonitrile linear during 7.5 min at 1.5 ml/min

Detection: 210 nm (analogue output from DAD)

ELS (analogue output from ELS): 40° C.

MS ionisation mode: API-ES

HPLC

Method 01_B4_2: RP-analysis was performed using a Waters 600S system fitted with a Waters 996 diode array detector. UV detections at 214 nm and 254 nm were collected using a Symmetry 300 C18, 5 μm, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Method 02_B4_4: The RP-analyses was performed using a Alliance Waters 2695 system fitted with a Waters 2487 dualband detector. UV detections at 214 nm and 254 nm were collected using a Symmetry300 C18, 5 um, 3.9 mm×150 mm column, 42° C. Eluted with a linear gradient of 5-95% acetonitrile, 90-0% water, and 5% trifluoroacetic acid (1.0%) in water over 15 minutes at a flow-rate of 1.0 min/min.

Example 1

Construction of Yeast Expression Systems and Production of GLP-1 Analogue Precursor Molecules (R34)GLP-1(8-37)

Expressions plasmids are of the C—POT type, similar to those described in EP 171,142. These are 2μ-based expression vectors characterized by containing the *Schizosaccharomyces pombe* triose phosphate isomerase gene (POT) for the purpose of plasmid selection and stabilization in *S. cerevisiae*. The plasmids also contain the *S. cerevisiae* triose phosphate isomerase promoter and terminator (FIG. 1). These sequences are similar to the corresponding sequences in plasmid pKFN1003 (described in WO 90100075) as are all other sequences except the following: 1) The sequence of the EcoRI-XbaI fragment encoding the fusion protein of the leader and the insulin product. 2) A silent mutation has been introduced resulting in removal of a NcoI-site in the 2μ-region in the expression vector. In order to facilitate cloning of different fusion proteins a the DNA sequence encoding the MFα1 pre-pro leader has been changed to incorporate a NcoI site (see FIG. 2) and is called the MFα1* pre-pro leader. Thus the NcoI-XbaI fragment is simply replaced by an NcoI-XbaI fragment encoding the GLP-1 precursor molecule of interest. Such NcoI-XbaI fragments may be synthesized using synthetic oligonucleotides and PCR according to standard techniques. In addition to the alpha-leader other leaders can be used.

Synthetic DNA fragments containing sequences encoding (R34)GLP-1(11-37), (E22,R26,R34)GLP-1(8-37)K38 and (E22,R26,R34,K37)GLP-1(8-37) were obtained form Geneart AG, BioPark, Josef-Engert-Str. 11, D-93053 Regensburg, Germany. The synthetic DNA encoding (E22, R26,R34)GLP-1(8-37)K38 and (E22,R26,R34,K37)GLP-1 (8-37) was furnished with 3' and 5' DNA sequences encoding N- and C-terminal extension to facilitate expression in yeast (FIG. 2) and termed Ext1-(E22,R26,R34)GLP-1(8-37) K38-Ext2 and Ext1-(E22,R26,R34,K37)GLP-1(8-37)-Ext2. The synthetic DNA was digested with NcoI and XbaI and ligated to the NcoI-XbaI vector fragment of the modified cPOT type expression vector (FIG. 1). This resulted in three expression plasmids pSA273, pSA277 and pSA278 encoding (R34)GLP-1(11-37) (SEQ ID NO:6), Ext1-(E22,R26, R34)GLP-1(8-37)K38-Ext2 (SEQ ID NO:7) and Ext1-(E22, R26,R34,K37)GLP-1(8-37)-Ext2 (SEQ ID NO:8), respectively.

The expression plasmids were propagated in *E. coli*, grown in the presence of ampicillin and isolated using standard techniques (Sambrook et al., 1989). The plasmid DNA was checked for insert by appropriate restriction nucleases (e.g. EcoRI, NcoI, XbaI) and was shown by sequence analysis to contain the proper sequence of the GLP-1 analogue precursors molecules (R34)GLP-1(11-37), Ext1-(E22,R26,R34)GLP-1(8-37)K38-Ext2 and Ext1-(E22, R26,R34,K37)GLP-1(8-37)-Ext2. (FIG. 2).

The plasmids were transformed into *S. cerevisiae* strain ME1719 (MATa/α leu2/leu2 pep-4-3/pep-4-3 Δtpi::LEU2/ Δtpi::LEU2 Δura3/Δura3 Δyps1::URA3/Δyps1::ura3 Cir+). This strain is described in WO 98/01535. Yeast transformants harbouring the plasmid were selected by glucose utilization as carbon source on YPD (1% yeast extract, 2% peptone, 2% glucose) agar (2%) plates. This resulted in three yeast strains: γSA251, γSA259 and γSA260 expressing (R34)GLP-1(11-37) (SEQ ID NO:9), Ext1-(E22,R26,R34) GLP-1(8-37)K38-Ext2 (SEQ ID NO:10) and Ext1-(E22, R26,R34,K37)GLP-1(8-37)-Ext2 (SEQ ID NO:11), respectively.

The ME1719 yeast strains γSA251, γSA259 and γSA260 were inoculated into 5 ml of growth media, for example a medium consisting of 5 g/L (NH$_4$)$_2$SO$_4$, 184 mg/L (NH$_4$)$_2$ HPO$_4$, 2.88 g/L KH$_2$PO$_4$, 1.42 g/L MgSO$_4$.7H$_2$O, 1.28 g/L, K$_2$SO$_4$, 10.00 g/L succinic acid, 10.00 g/L casamino acids, 0.0112 g/L FeSO$_4$. 7H$_2$O, 0.0086 g/L MnSO$_4$.H$_2$O, 0.0014 g/L CuSO$_4$.5H$_2$O, 0.00185 g/L ZnSO$_4$.7H$_2$O, 0.0129 g/L CaCl2.2H$_2$O, 0.071 g/L citric acid, 28.0 mg/L m-inositol, 14.0 mg/L choline chloride, 2.8 mg/L thiamine, 2.8 mg/L niacinamide, 2.1 mg/L Ca-pantothenic acid, 0.14 mg/L biotin, 0.14 mg/L folic acid, 40 g/L glucose. The cultivation was carried out at 30° C. for 3 days. After centrifugation the supernatant was removed for quantitative HPLC analysis by which method the concentration of secreted GLP-1 analogue was measured. The identity of the GLP-1 precursor molecules was confirmed by LC/MS analysis. The N- and C-terminal extensions employed to facilitate expression of (E22,R26,R34)GLP-1(8-37)K38 and (E22,R26,R34,K37) GLP-1(8-37) were removed by the lysine specific *Achromobactor Lyticus* Protease 1 according to well-established procedures.

Example 2

Construction of Yeast Expression System and Production of GLP-1 Analogue Precursor Molecule (R34)GLP-1(9-37)

A synthetic DNA fragment encoding (R34)GLP-1(9-37) was constructed by standard PCR using the primers 5' -AGGGGTATCCATGGCTAAGAGAGAAGGTACCT- TCACCTCTGAC-3' (SEQ ID NO: 14) and 5'-AATCT- TAGTTTCTAGAGCCTGCG-3' (SEQ ID NO: 15) and a plasmid containing DNA sequence encoding (R34)GLP-1 (7-37). The primers were designed an 5' NcoI site and a 3' XbaI site. Thus the PCR fragment could be digested by NcoI and XbaI after purification and ligated to the NcoI-XbaI vector fragment of the modified cPOT type expression vector described in example 1. The resulting plasmid encoding (R34)GLP-1(9-37) was named pSA82.

The expression plasmid was propagated in *E. coli*, grown in the presence of ampicillin and isolated using standard techniques (Sambrook et al., 1989). The plasmid DNA was checked for insert by appropriate restriction nucleases (e.g. EcoRI, NcoI, XbaI) and was shown by sequence analysis to contain the proper sequence of the GLP-1 analogue precursors molecule (R34)GLP-1(9-37).

The plasmid was transformed into *S. cerevisiae* strain ME1719 and a yeast transformant harbouring the plasmid was selected as described in example 1. The resulting yeast strain expressing (R34)GLP-1(9-37) was named γSA96.

The yeast strain was cultivated in growth media and (R34)GLP-1(9-37) was recovered from the media as described in example 1.

Example 3

Construction of Yeast Expression Systems for GLP-1 Precursors

The leader and Kex2p cleavage sites were optimized in order to augment expression yield of processed, secreted peptide. Synthetic DNA fragments encoding various leader and (R34)GLP-1(11-37), or (R34)GLP-1(9-37) constructs were amplified by standard PCR. The forward primers included an NcoI-site and the sequence encoding the optimized leader sequence. The reverse primers included an XbaI-site. Hence, allowing cloning of the NcoI-XbaI restricted PCR-fragments into the NcoI-XbaI restricted cPOT-type expression vector. Refer to FIG. 4 for sequences, plasmid numbering of (R34)GLP-1(11-37) encoding expression construct and strain names.

Expression plasmids were propagated in *E. coli* in the presence of ampicillin and isolated using standard techniques (Sambrook et al., 1989). Plasmid constructs were checked by restriction endonuclease digestion using appropriate restriction enzymes. Encoding sequences were sequence verified.

Plasmids were transformed into the *S. cerevisae* strain ME1719. Yeast cells harboring the plasmid were selected as described in example 1. Cultivation of the yeast strains was essentially as described in example 1

Optimization of the sequence in the vicinity of the Kex2p cleavage-site, P1 to P6, led to a modest increase in yield (FIG. 4: B). Incorporation of a Proline in the sequence (P3 to P6) was explored as a potential means of increasing exposure of the Kex2p cleavage site to Kex2p. Although, this turned out to not to be the case for (R34)GLP-1(11-37) a beneficial effect may be observed for (R34)GLP-1(11-37) (FIG. 4:H, I). Variation of residues P7 to P11 had a pronounced effect on expression yield, 2-2.5 fold increases were observed when motifs containing charged amino acids were introduced (FIG. 4: M-Z, K5-7, L2-4). A series of constructs had been designed for processing with DAP-1 (dipeptidyl aminopeptidase) in the downstream process (FIG. 4: G, J, K, L). Constructs J and L contain a Q in the position before Thr-11, to protect against promiscuous cleavage by DAP-1 of the GLP-1 peptide. This Gln can subsequently be removed using the enzymes Q-cyclase and pGAPase (Qiagen).

TABLE 1

| SEQUENCE | SEQUENCE REF. | YIELD | PLASMID | STRAIN NAME |
| --- | --- | --- | --- | --- |
| RARYKR (SEQ ID NO: 16) | (A) | 25 | pISNN546 | SCI50 |
| RDLGKR (SEQ ID NO: 17) | (B) | 125 | pISNN547 | SCI51 |
| RDLAKR (SEQ ID NO: 18) | (C) | 88 | pISNN548 | SCI52 |
| RARAKR (SEQ ID NO: 19) | (D) | 58 | pISNN549 | SCI53 |

TABLE 1-continued

| SEQUENCE | SEQUENCE REF. | YIELD | PLASMID | STRAIN NAME |
| --- | --- | --- | --- | --- |
| RALDKR (SEQ ID NO: 20) | (E) | 58 | pISNN550 | SCI54 |
| RALAKR (SEQ ID NO: 21) | (F) | 43 | pISNN551 | SCI55 |
| PRDLGKR (SEQ ID NO: 22) | (H) | 68 | pISNN585 | SCI57 |
| RPLGKR (SEQ ID NO: 23) | (I) | 58 | pISNN586 | SCI58 |
| RDLGKREA (SEQ ID NO: 24) | (G) | 200 | pISNN589 | SCI56 |
| RDLGKREAQ (SEQ ID NO: 25) | (J) | 188 | pISNN599 | SCI59 |
| RDLGKREAEA (SEQ ID NO: 26) | (K) | 240 | pISNN590 | SCI60 |
| RDLGKREALEKR (SEQ ID NO: 27) | (K5) | n.d. | pISNN654 | |
| RDLGRREALEKR (SEQ ID NO: 28) | (K6) | n.d. | pISNN655 | |
| RDLGEALEKR (SEQ ID NO: 29) | (K7) | 100 | pISNN652 | |
| RDLGKREAEAQ (SEQ ID NO: 30) | (L) | 253 | pISNN587 | SCI44 |
| RDLGKREAEAQKR (SEQ ID NO: 31) | (L2) | 25 | pISNN650 | |
| RDLGRREAEAQKR (SEQ ID NO: 32) | (L3) | n.d. | pISNN656 | |
| RDLGEAEAQKR (SEQ ID NO: 33) | (L4) | 13 | pISNN651 | |
| ERLERDLGKR (SEQ ID NO: 34) | (M) | 225 | pISNN610 | SCI63 |
| KERLERDLGKR (SEQ ID NO: 35) | (N) | 100 | pISNN611 | SCI64 |
| ERLEKR (SEQ ID NO: 36) | (O) | 138 | pISNN617 | SCI65 |
| KERLEKR (SEQ ID NO: 37) | (P) | 125 | pISNN612 | SCI66 |
| PERLERDLGKR (SEQ ID NO: 38) | (Q) | 73 | pISNN613 | SCI67 |
| PERLEKR (SEQ ID NO: 39) | (R) | 125 | pISNN614 | SCI68 |
| EAEARDLGKR (SEQ ID NO: 40) | (S) | 175 | pISNN615 | SCI69 |
| PEAEARDLGKR (SEQ ID NO: 41) | (T) | 100 | pISNN616 | SCI70 |
| EEAEKR (SEQ ID NO: 42) | (U) | 125 | pISNN623 | SCI71 |
| EEAERDLGKR (SEQ ID NO: 43) | (V) | 218 | pISNN624 | SCI72 |
| RDLGEEAEKR (SEQ ID NO: 44) | (X) | 218 | pISNN625 | SCI73 |

TABLE 1-continued

| SEQUENCE | SEQUENCE REF. | YIELD | PLASMID | STRAIN NAME |
|---|---|---|---|---|
| EEAELAKR (SEQ ID NO: 45) | (Y) | 165 | pISNN626 | SCI74 |
| EEAELGKR (SEQ ID NO: 46) | (Z) | 105 | pISNN627 | SCI75 |
| KR | | 100 | pISNN545 | SCI43 |

Example 4

Preparation of N-Terminal Extension Boc-His(Boc)-Aib-Glu(O-tBu)-Gly-OH

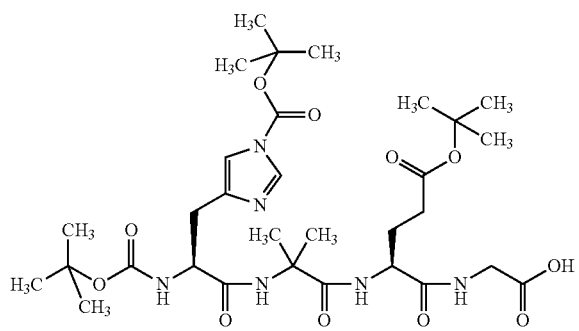 [SMILES: CC(C)(C)OC(=O)CC[C@H](NC(=O)C(C)(C)NC(=O)[C@H](Cc1cn(C(=O)OC(C)(C)C)cn1)NC(=O)OC(C)(C)C)C(=O)NCC(=O)O]

2-chlorotritylchloride resin (1% DVB, 1.4 mmol/g, 10 g, 14.0 mmol) was pre-swelled in DCM before it was added a solution of Fmoc-Gly-OH (8.3 g, 28 mmol) and DIPEA (9.03 g, 70 mmol) in 100 mL DCM, and agitated for 30 min at r.t. The resin was washed with NMP (2×100 mL) and 2×100 mL DCM-MeOH-DIPEA (80:15:5, 10 min) then NMP (3×100 mL), before treatment with 20% piperidine in NMP (3×100 mL) for 10 min each. The resin was washed with NMP (6×100 mL), DCM (2×100 mL) and MeOH (2×100 mL) and dried over night in vacuo. The resin was treated with 100 mL 20% piperidine in NMP for 10 min. The step was repeated twice before it was washed with NMP (5×100 mL).

Fmoc-Glu(O-tBu)-OH (23.8 g, 56 mmol) was dissolved in a mixture of 100 mL NMP and 20 mL DCM. HOAt (7.62 g, 56 mmol) was added followed by drop wise addition of DIC (7.07 g, 56 mmol). The mixture was stirred for 15 min before DIPEA (9.03 g, 70 mmol) was added, and the mixture was transferred to the resin. The resin was agitated for 16 h before it was washed with NMP (4×100 mL). The resin was treated with 20% piperidine in NMP (100 mL) for 10 min. The step was repeated twice before it was washed with NMP (5×100 mL).

Fmoc-Aib-OH (18.22 g, 56 mmol) was dissolved in a mixture of 100 mL NMP and 20 mL DCM. HOAt (7.62 g, 56 mmol) was added followed by drop wise addition of DIC (7.07 g, 56 mmol). The mixture was stirred for 20 min before it was added to the resin. The mixture was agitated for 30 min before DIPEA was added. The mixture was agitated for 16 h before the resin was washed with NMP (4×100 mL). The resin was treated with 20% piperidine in NMP (100 mL) for 10 min. The step was repeated twice before it was washed with NMP (5×100 mL).

Boc-His(Boc)-OH (19.9 g, 56 mmol) was dissolved in a mixture of 100 mL NMP and 20 mL DCM. HOAt (7.62 g, 56 mmol) was added followed by drop wise addition of DIC (7.07 g, 56 mmol). The mixture was stirred for 20 min before it was added to the resin. The mixture was agitated for 30 min before DIPEA was added. The mixture was agitated for 16 h before the resin was washed with NMP (3×100 mL), DCM (4×100 mL).

Trifluoroethanol-DCM (1:4, 125 mL) was added and the resin was agitated for 1 hour. The filtrate was collected and a new portion of trifluoroethanol-DCM (1:4, 125 mL) was added and agitated for 15 min. The filtrate was collected and the solvent was removed in vacuo to give a clear oil. Ice cold diethyl ether (300 mL) was added whereupon a white precipitate was formed. Light petrol ether (100 mL) was added and the precipitate was filtered off, washed with diethyl ether and dried in vacuo.

Yield: 7.3 g

HPLC (Method 01_B4): Rt=7.8 min

LCMS:m/z=944 (M+H)$^+$

Calculated MW=943.2

Example 5

Preparation of N-Terminal Extension Boc-His(Boc)-Aib-Glu(O-Tbu)-Gly-OSuc

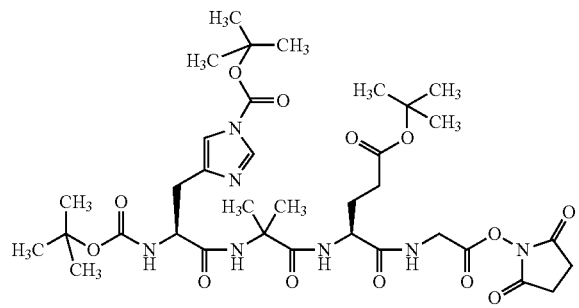 [SMILES: CC(C)(C)OC(=O)CC[C@H](NC(=O)C(C)(C)NC(=O)[C@H](Cc1cn(C(=O)OC(C)(C)C)cn1)NC(=O)OC(C)(C)C)C(=O)NCC(=O)ON1C(=O)CCC1=O]

A solution of Boc-His(Boc)-Aib-Glu(O-tBu)-Gly-OH (1.0 g, 1.47 mmol) in dry THF (60 mL), was added DIPEA (0.47 g, 3.66 mmol) and O—(N-succinimidyl)-N,N,N',N'-tetramethyluronium hexafluorophosphate (1.10 g, 3.66 mmol) and the reaction mixture was stirred for 24 h at room temperature. Dichloromethane (250 mL) was added and the solution was washed with H$_2$O (2×100 mL). The organic phase was dried over MgSO4, filtered and concentrated in vacuo to give 1.1 g of Boc-His(Boc)-Aib-Glu(O-tBu)-Gly-OSu.

HPLC (Method 01_B4):Rt=8.3 min

LCMS:m/z=780.9 (M+H)$^+$

Calculated MW=779.9

Example 6

Preparation of acylating agent 17-((S)-1-tert-Butoxycarbonyl-3-{2-[2-({2-[2-(2,5-dioxopyrrolidin-1-yloxycarbonylmethoxy)ethoxy]ethylcarbamoyl}methoxy)ethoxy]ethylcarbamoyl}propylcarbamoyl)heptadecanoic acid tert-butyl ester

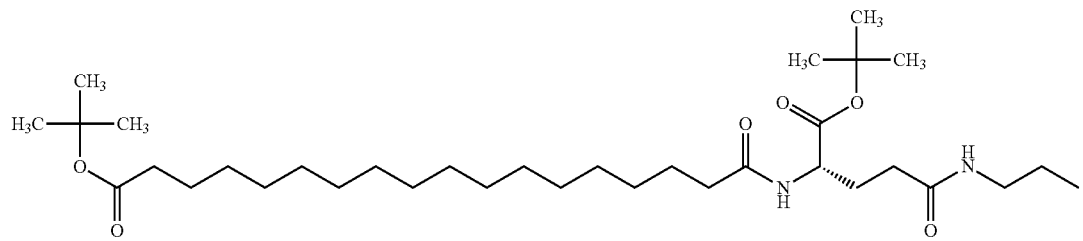

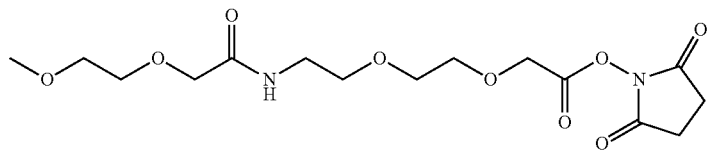

The title compound was prepared by the general method for the preparation and activation of acylating agents A-OH A-B—C-D-OH, A-C-D-OH, A-B—C—OH as described above and similar to example 4.

HPLC (Method 01_B4):Rt=16.2 min
LCMS:m/z=944 (M+H)$^+$
Calculated MW=943.2

Example 7

Preparation of acylating agent 17-((S)-1-Carboxy-3-{2-[2-({2-[2-(2,5-dioxo-pyrrolidin-1-yloxycarbonylmethoxy)ethoxy]-ethylcarbamoyl}-methoxy)-ethoxy]ethylcarbamoyl}propylcarbamoyl)-heptadecanoic acid

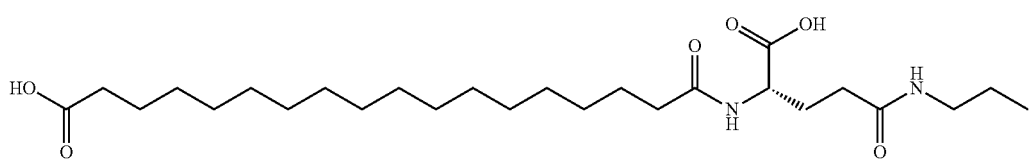

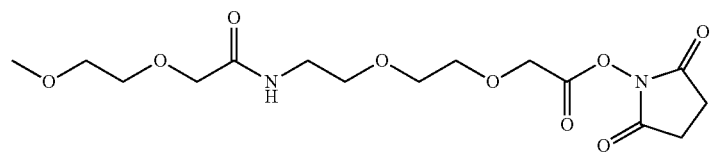

17-((S)-1-tert-Butoxycarbonyl-3-{2-[2-({2-[2-(2,5-dioxopyrrolidin-1-yloxycarbonylmethoxy)ethoxy]ethylcarbamoyl}methoxy)ethoxy]-ethylcarbamoyl}propylcarbamoyl)heptadecanoic acid tert-butyl ester was dissolved in TFA and the resulting solution was stirred for 2 hr. and evaporated in vacuo to dryness. The resulting oil was coevaporated with toluene thrice to dryness resulting in an oily residue LCMS: m/z=831 (M+H)$^+$

Example 8

Preparation of GLP-1 derivative [Arg34]GLP-1-(11-37)-N-epsilon26-[2-(2-{2-[2-(2-{2-[(S)-4-Carboxy-4-(17-carboxyheptadecanoylamino) butyrylamino]ethoxy}ethoxy)acetylamino]ethoxy}ethoxy) acetyl]-[Aib8,Arg34]GLP-1-(7-37)

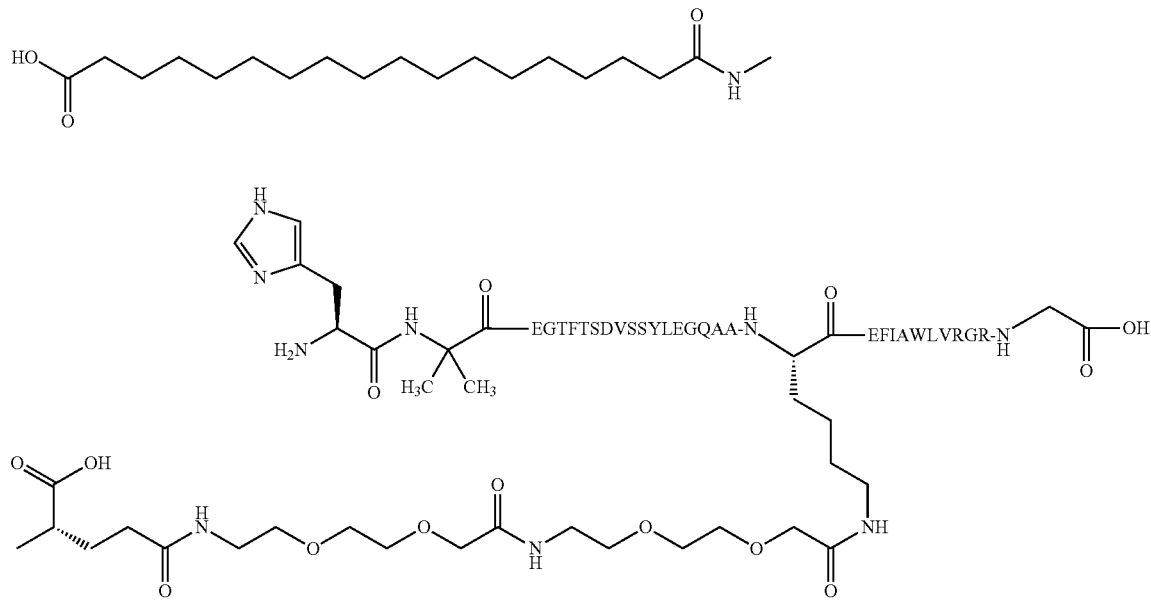

[Arg34]GLP-(11-37) (50 mg, 0.017 mmol) was dissolved in 2 mL water and DIPEA (89 μL, 0.51 mmol) was added. The mixture was stirred for 10 min before pH was measured to 10.6. Then a solution of 17-((S)-1-tert-butoxycarbonyl-3-{2-[2-({2-[2-(2,5-dioxopyrrolidin-1-yloxycarbonyl-methoxy)-ethoxy]-ethylcarbamoyl}methoxy)ethoxy] ethylcarbamoyl}propylcarbamoyl)-heptadecanoic acid tert-butyl ester (20.5 mg, 0.022 mmol) in MeCN (1.5 mL) was added dropwise over 10 min. The reaction mixture was stirred for 1 hour before MeCN was removed in vacuo and the solution was lyophilized.

The resulting residue was dissolved in NMP (2 mL) whereupon DIPEA (22 μL, 0.17 mmol) and Boc-His(Boc)-Aib-Glu(OtBu)-Gly-OSu (26 mg, 0.033 mmol) was added. The reaction mixture was stirred for 4 hours before an additional portion of His(Boc)-Aib-Glu(OtBu)-Gly-OSu (13 mg 0.017 mmol) was added and the reaction mixture was stirred over night. Ice cold diethyl ether (20 mL) was added whereupon a white precipitate was formed. The precipitate was isolated by centrifugation and the supernatant was decanted off. The precipitate was washed with 10 mL diethyl ether and dried in the air.

Deprotection

The crude intermediate was dissolved in TFA-triisopropylsilane-H₂O (95:2.5:2.5, mL) and stirred for 3 h whereupon the solution was concentrated in vacuo to app. 1 mL. Ice cold diethyl ether (20 mL) was added whereupon a precipitate was formed. The precipitate was isolated by centrifugation and the supernatant was decanted off. The precipitate was washed with diethyl ether and dried. The crude compound was dissolved in acetic acid-H₂O (3:7) (10 mL) and purified on HPLC.

HPLC (Method 02_B4): Rt=9.6 min
LCMS:m/z=1372.5 (M+3H)$^{3+}$
Calculated MW=4113.7

Example 9

Preparation of GLP-1 derivative N-epsilon26-[2-(2-[2-(2-[2-(2-[4-(17-tert-butoxycarbonylheptadecanoyl-amino)-4(S)-tert-butoxycarbonylbutyrylamino]ethoxy)ethoxy]acetylamino)ethoxy]ethoxy) acetyl]-[Arg34]GLP-1-(9-37) peptide

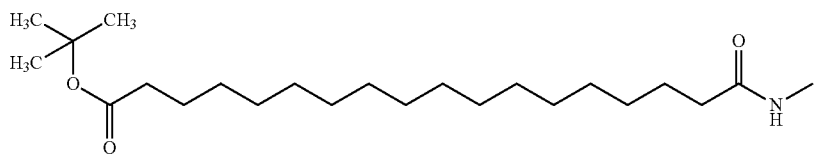

-continued

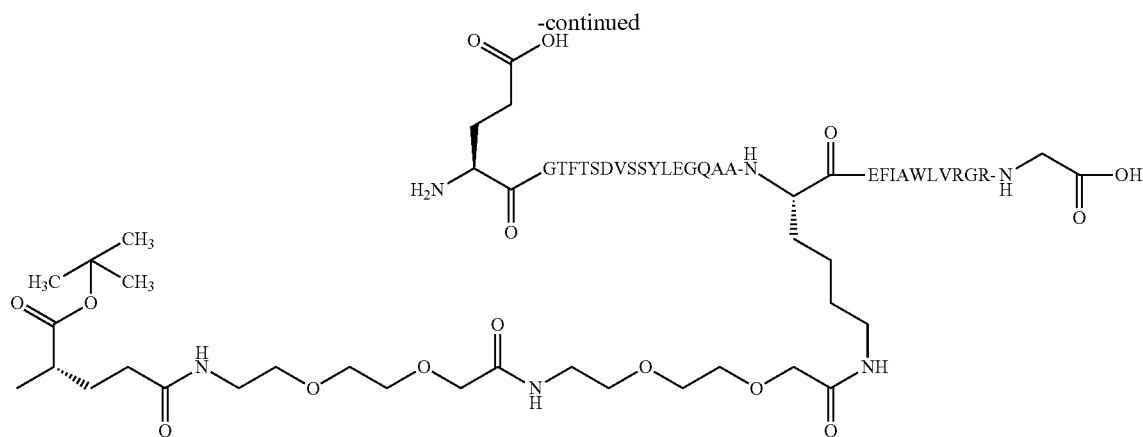

To a solution of 17-{(S)-1-tert-butoxycarbonyl-3-[2-(2-{[2-(2-carboxymethoxyethoxy)ethylcarbamoyl]methoxy}ethoxy)ethylcarbamoyl]propyl carbamoyl}heptadecanoic acid tert-butyl ester (94.0 mg, 0.112 mmol) in NMP (2.0 ml) was added O-(1-succinimidyl)-N,N,N',N'-tetramethyluronium hexafluorophosphate (TSTU, 41.7 mg, 0.139 mmol) and TEA (96.0 µl, 0.69 mmol). After stirring for 30 min. at room temperature the mixture was added drop wise to a solution of [Arg34]GLP-1-(9-37) peptide (220 mg, 0.069 mmol) in water (9 ml) and TEA (96.0 µl, 0.69 mmol). After stirring for additional 30 min at room temperature the mixture was diluted with water (30 ml) and lyophilized for 16 h giving an oil/amorphous mixture which was dissolved in a mixture of acetic acid-acetonitrile-water (30:20:50, 180 ml), filtered and purified by HPLC to give N-epsilon26-[2-(2-[2-(2-[2-(2-[4-(17-tert-butoxycarbonylheptadecanoyl-amino)-4(S)-tert-butoxycarbonylbutyrylamino]ethoxy)ethoxy]acetylamino)ethoxy]ethoxy)acetyl]-[Arg34]GLP-1-(9-37) peptide.

HPLC (Method 02_B4_4): Rt=12.1 min
LCMS:m/z=1335.5 (M+3H)$^{3+}$
Calculated MW=4003.6

Example 10

Preparation of GLP-1 analogue N-epsilon26-[2-(2-{2-[2-(2-{2-[(S)-4-Carboxy-4-(17-carboxy-heptadecanoylamino)-butyrylamino]ethoxy}ethoxy)acetylamino]-ethoxy}ethoxy)-acetyl][Aib8,Arg34]GLP-1-(7-37) peptide

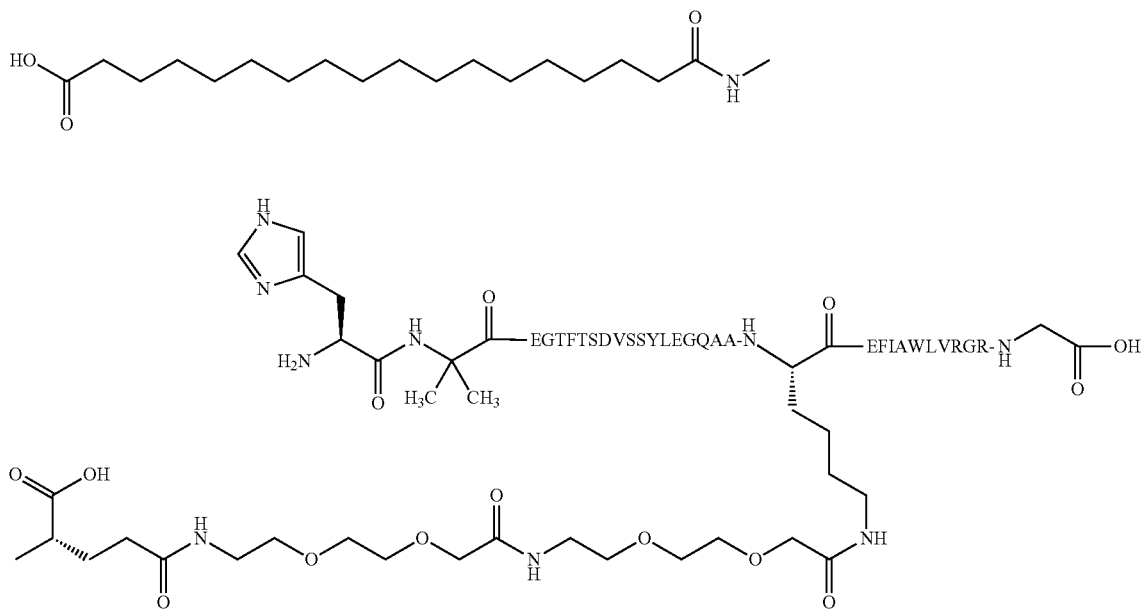

To a solution of Boc-His(Boc)-Aib-OH (23 mg, 0.052 mmol) in NMP (2.0 ml) were added 2-(1H-9-azabenzotriazole-1-yl)-1,1,3,3-tetramethyluronium hexafluorophosphate (HATU, 20 mg, 0.052 mmol) and TEA (29 µl, 0.208 mmol). After stirring for 45 min. the mixture was added to a solution of N-epsilon26-[2-(2-[2-(2-[2-(2-[4-(17-tert-butoxycarbonylheptadecanoylamino)-4(S)-tert-butoxycarbonylbutyrylamino]ethoxy)ethoxy]acetylamino)-ethoxy]ethoxy)acetyl]-[Arg34]GLP-1-(9-37) peptide (83 mg, 0.021 mmol) and TEA 3.6 ul, 0.026 mmol). After stirring for 14 days the reaction mixture was diluted with water (100 ml) and purified by HPLC. The purified fractions were pooled and the organic solvent removed in vacuo before the residue was lyophilized for 16 h.

To the residue was added a mixture of trifluoroacetic-triisopropylsilane-water (94:3:3, 10 ml). After stirring for 2 hours the reaction mixture was evaporated in vacuo, the residue was dissolved in a mixture of water-ammonia (99:1, 100 ml) and purified by preparative HPLC to give the title compound.

HPLC (Method 02_B4_4): Rt=9.4 min
LCMS:m/z=1372 (M+3H)³⁺
Calculated MW=4113.7

Example 11

Preparation of acylating agent 20-[4-((S)-1-tert-Butoxycarbonyl-3-{2-[2-({2-[2-(2,5dioxo-pyrrolidin-1-yloxycarbonylmethoxy)-ethoxy]ethylcarbamoyl}methoxy)ethoxy]ethylcarbamoyl}-propylcarbamoyl)piperidin-1-yl]-20-oxo-icosanoic acid tert butyl ester

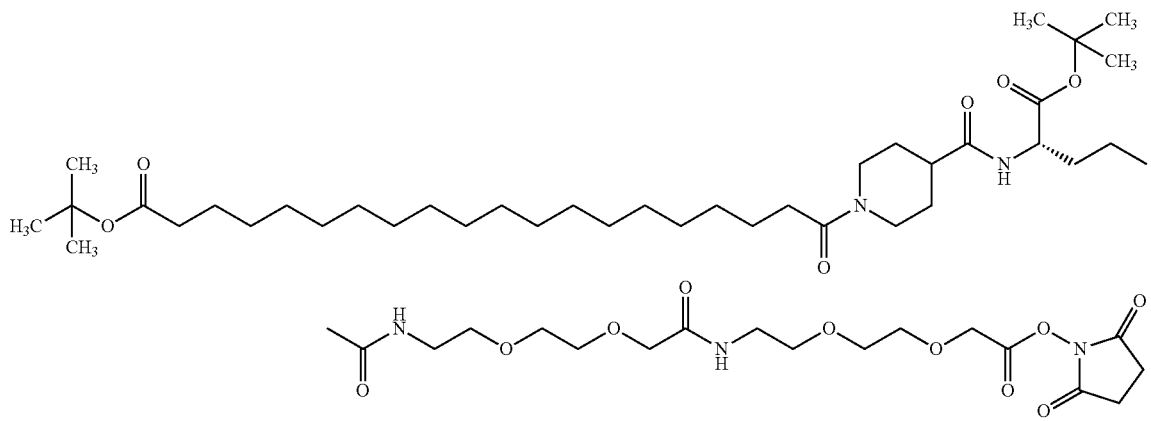

The title compound was prepared by the general method for the preparation and activation of acylating agents A-OH A-B-C-D-OH, A-C-D-OH, A-B-C—OH as described above and similar to example 4.

LCMS: m/z=1111 (M+H)⁺
LCMS:m/z=1082.6 (M+H)⁺
Calculated MW=1082.4

Example 12

Preparation of GLP-1 analogue [Des amino-His7, Glu22,Arg26,34,Lys37(Lys(2-{2-[2-(2-{2-[2-((S)-4-Carboxy-4-{[1-(19-carboxynonadecanoyl)piperidine-4-carbonyl]amino}-butyrylamino)ethoxy]-ethoxy}-acetylamino)ethoxy]ethoxy}acetyl)]-GLP-1 (7-37) peptide

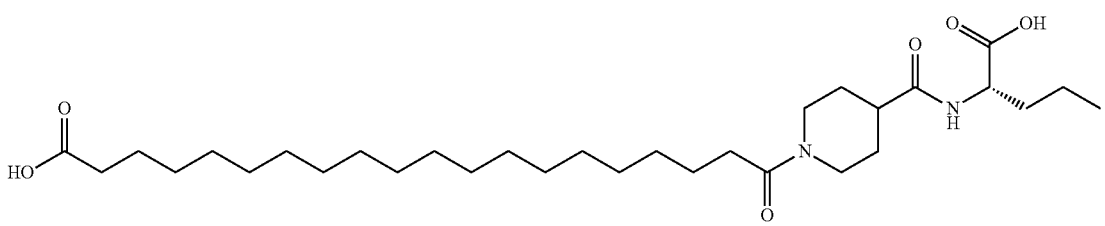

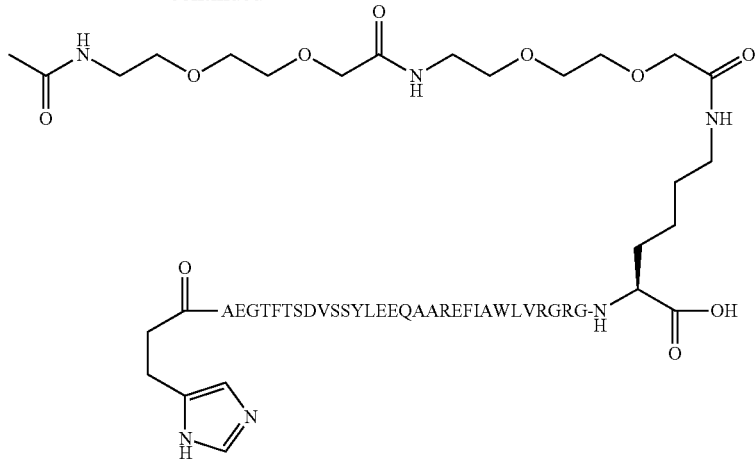

To a solution of [Glu22,Arg26,34,Lys37]GLP-1-(8-37) peptide (46 mg, 0.013 mmol) in 2 mL water was added DIPEA (50.4 mg, 0.39 mmol) and the mixture was stirred for 10 min before a solution of 20-[4-((S)-1-tert-butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-piperidin-1-yl]-20-oxo-icosanoic acid tert butyl ester (32.4 mg, 0.03 mmol) in 1 mL MeCN was added dropwise over the course of 15 min. The reaction mixture was stirred for 20 min before water (20 mL) was added, and the solution was freeze dried The resulting residue was dissolved in NMP (1 mL) and 4-[2-(2,5-dioxo-pyrrolidin-1-yloxycarbonyl)-ethyl]-imidazole-1-carboxylic acid adamantan-1-yl ester (Adoc-des amino His-OSu ester) mixture was stirred for 3 hours before it was added drop wise to ice cold diethyl ether (20 mL). The white precipitate was isolated by centrifugation and washed twice with diethyl ether (20 mL) and dried.

The resulting residue was treated with TFA-TIPS-water (95:2.5:2.5, 1 mL) for 3 hours before it was added drop wise to ice cold diethyl ether (10 mL). The white precipitate was isolated by centrifugation and washed twice with diethyl ether (10 mL). The residue was purified by preparative HPLC to give the title compound HPLC (Method 01_B4_2): Rt=11.1 min LCMS:m/z=1484 (M+3H)$^{3+}$ Calculated MW=4452.1

Example 13

Preparation of 4-[2-(2,5-Dioxo-pyrrolidin-1-yloxycarbonyl)ethyl]imidazole-1-carboxylic acid adamantan-1-yl ester

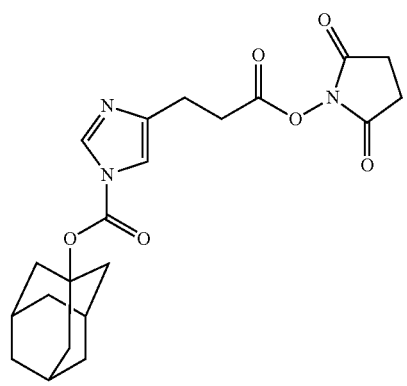 [SMILES: O=C(CCc1cn(C(=O)OC23CC4CC(CC(C4)C2)C3)cn1)ON1C(=O)CCC1=O]

4-(2-Carboxyethyl) imidazole-1-carboxylic acid adamantan-1-yl ester (1 g, 3.1 mmol) was dissolved in THF (5 mL) and DMF (10 mL). The solution was cooled to 0° C. and TSTU and DIEA were added. The solution was stirred at 0° C. for 1 h, and at room temperature for 16 h. The sample was concentrated under vacuum. EtOAc (100 mL) was added, and the solution was washed with 0.2 N HCl (2×50 mL), dried over MgSO$_4$, and concentrated under vacuum to yield a sticky crystalline residue (1.18 g, 90% yield). The crude product was used without further purification.

LCMS:m/z=416.2 (M+H)

$^1$H-NMR (DMSO, 300 MHz) (selected signals) δ 8.22 (s, 1H), 7.37 (s, 1H), 3.02 (t, 2H), 2.82-2.88 (m, 2H), 2.81 (s, 4H), 2.19 (s-br, 9H), 1.66 (s, 6H).

Example 14

Preparation of GLP-1 analogue N-epsilon 37{2-[2-(2-{2-[2-((R)-3-carboxy-3-{[1-(19-carboxynonade-canoyl)piperidine-4-carbonyl]amino}propionylamino)ethoxy]ethoxy}acetylamino)ethoxy]ethoxy}acetyl [Glu22, Arg26,34, Lys 37] GLP-1 (8-37) peptide

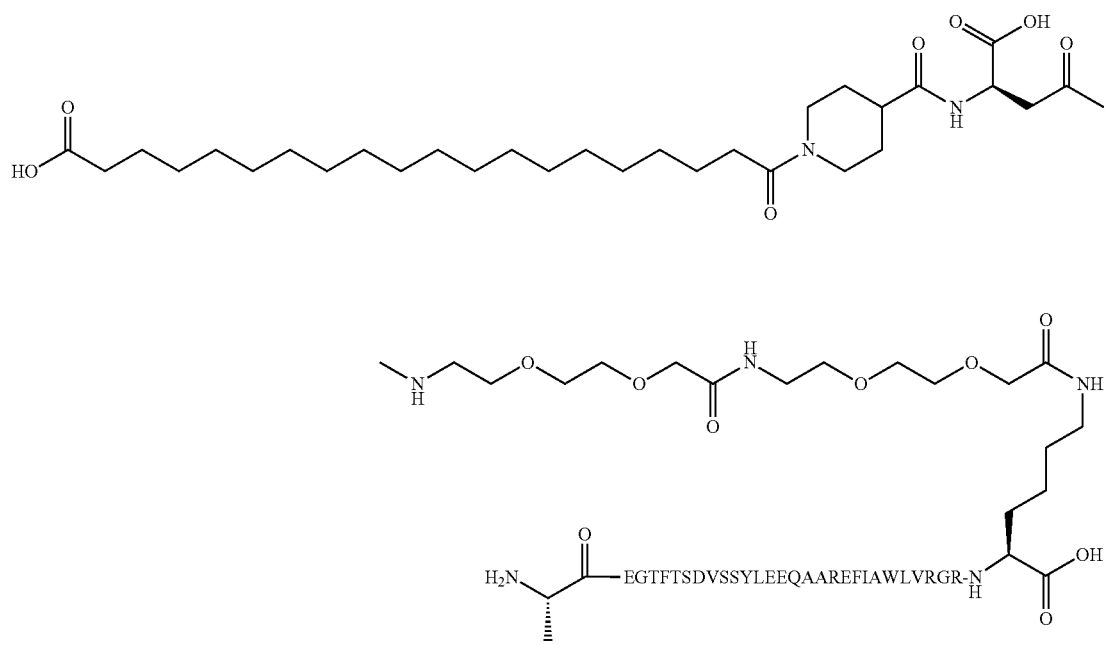

The GLP-1 analogue was prepared using a CEM Liberty peptide synthesizer starting with a Fmoc-Lys(Mtt)-wang resin. After the Fmoc group from Ala8 was removed, the N-terminal was protected by performing a double coupling with di-tert-butyl dicarbonate. The Mtt group was removed by washing the resin with DCM, treating the resin with hexafluoroisopropanol for 15 min at r.t and washing the resin with DCM. The N-epsilon 37 modifications were prepared on the CEM Libert peptide synthesizer using Fmoc-protected reagents and eicosane-dioic acid mono-tert-butyl ester. The crude peptide was cleaved from the resin TFA-TIPS-Water (95:2.5:2.5) and precipitated in ice cold ether, and isolated by centrifugation. The crude peptide was purified by preparative HPLC (4 cm dia.×200 mm, C18, 60 ml/min, 33-53% acetonitrile).

LCMS:m/z=1065.8 (M+4H)$^{4+}$

Example 15

Preparation of GLP-1 analogue N-epsilon 37{2-[2-(2-{2-[2-((R)-3-carboxy-3-{[1-(19-carboxynonade-canoyl)piperidine-4-carbonyl]amino}propionylamino)ethoxy]ethoxy}acetylamino)ethoxy]ethoxy}acetyl[Des amino-His(Adoc)$_7$, Glu22, Arg26,34, Lys 37] GLP-1 (7-37) peptide The GLP-1 analogue N-epsilon 37{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [Glu22, Arg26,34, Lys 37] GLP-1 (8-37) peptide (2.1 mg, 0.001 mmol) was dissolved in NMP (105 μL). A solution of 4-[2-(2,5-dioxo-pyrrolidin-1-yloxy-carbonyl)ethyl]imidazole-1-carboxylic acid adamantan-1-yl ester was prepared by dissolving 25.3 mg in 1296 μL NMP, and 25 μL of this solution was added to the peptide solution followed by DIEA (0.9 μL). The conversion to the product was followed by LCMS analysis. After 2 h at r.t, the ELS signal ratio of the product to the starting peptide was observed to be 976:28 (97% conversion).

LCMS:m/z=1141.1 (M+4H)$^{4+}$

Example 16

Preparation of acylating agent 19-{[trans-4-((S)-1-Carboxy-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-cyclohexylmethyl]-carbamoyl}-nonadecanoic acid

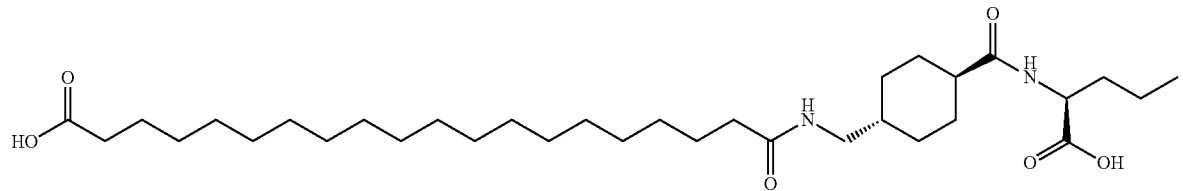

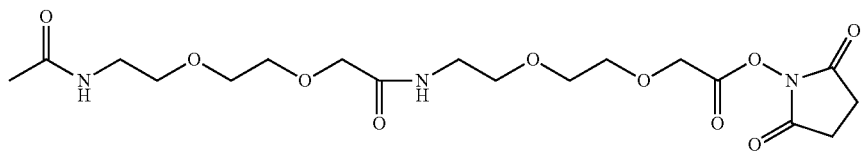

19-{[trans-4-((S)-1-tert-Butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-cyclohexylmethyl]-carbamoyl}-nonadecanoic acid tert-butyl ester (1.0 g, 0.9 mmol) was stirred in TFA (10 mL) for 1 h 45 min before 100 mL ice cold diethyl ether was added. The white precipitate was isolated by centrifugation and washed 3× with diethyl ether to give the title compound.

The precipitate was dried in vacuo for 16 hours.
LCMS: m/z=999 (M+1)⁺

Example 17

Preparation of GLP-1 analogue N-epsilon37-[2-(2-{2-[2-(2-{2-[(S)-4-Carboxy-4-({trans-4-[(19-carboxynonadecanoylamino)methyl]cyclohexanecarbonyl}amino)-butyrylamino]ethoxy}ethoxy)acetylamino]ethoxy}ethoxy)acetyl]-[DesaminoHis7,Glu22,Arg26,Arg34,Lys37]GLP-1-(7-37) Peptide

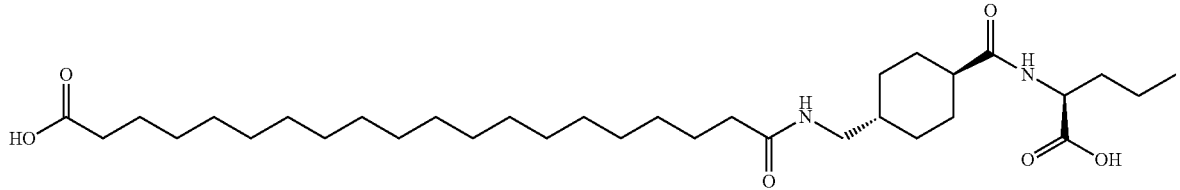

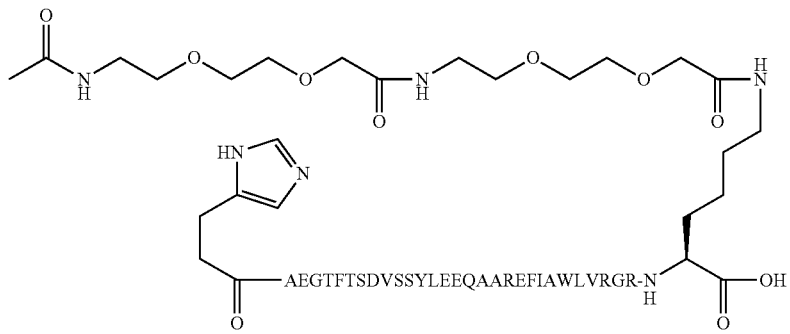

[Glu22, Arg26, Arg34, Lys37]GLP-1-(8-37) prepared via recombinant technique (300 mg, 0.09 mmol) dissolved in 6 mL water was added DIPEA (373 μL, 2.19 mmol) and stirred for 10 min whereupon a solution of 19-{[trans-4-((S)-1-carboxy-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-cyclohexylmethyl]-carbamoyl}-nonadecanoic acid (175.7 mg, 0.18 mmol) in NMP (1.7 mL) was added dropwise. The mixture was stirred for 90 min before $Na_2HPO_4 \times 7H_2O$ (470.6 mg, 1.76 mmol) was added and pH was adjusted to 8.4 using 1 N HCl.

In another flask 3-(1H-Imidazol-4-yl)-propionic acid (93.2 mg, 0.53 mmol), O—(N-succinimidyl)-N,N,',N'-tetramethyluronium tetrafluoroborate (159.0 mg, 0.53 mmol) and DIPEA (180 μL, 1.06 mmol) was mixed in NMP (0.75 mL) and the solution was stirred for 1 hour before it was added drop wise to the reaction mixture containing the peptide. The mixture was stirred for 14 hours whereupon piperidine (350 μL, 3.51 mmol) was added. The mixture was stirred for another two hours, before it was diluted with water to a total volume of 20 mL, and purified by preparative HPLC, using a gradient from 33 to 53% MeCN in water.
LCMS:m/z=1475.8 $(M+3H)^{3+}$ Example 18

Alternative preparation of GLP-1 analogue N-epsilon26-[2-(2-{2-[2-(2-{2-[(S)-4-Carboxy-4-(17-carboxyheptadecanoylamino)butyrylamino]ethoxy}ethoxy)-acetylamino]ethoxy}ethoxy)acetyl][Aib8,Arg34]GLP-1-(7-37)

and pH was adjusted to 8.3 using 1 N HCl. Fmoc-His-Aib-Glu-Gly-OSu (246.2 mg, 0.33 mmol) was added to the reaction mixture containing the peptide and the mixture was stirred for 14 hours whereupon piperidine (400 μL, 4.05 mmol) was added. The mixture was stirred for another 30 min, before it was diluted with water-MeCN (9:1) to a total volume of 40 mL, and purified by preparative HPLC, using a gradient from 30 to 50% MeCN in water.
LCMS:m/z=1372.5 $(M+3H)^{3+}$ Example 19

Alternative preparation of GLP-1 analogue N-epsilon26-[2-(2-{2-[2-(2-{2-[(S)-4-Carboxy-4-(17-carboxyheptadecanoylamino)butyrylamino]ethoxy}ethoxy)-acetylamino]ethoxy}ethoxy)acetyl][Aib8,Arg34]GLP-1-(7-37) peptide Acylation: Recombinant [Arg34]GLP-1-(11-37) (99 mg; 33 μmol) was suspended in $H_2O$ (4 mL) in the 70 mL reaction chamber of a Metrohm 848 Titrino plus titrator. The pH was adjusted to pH=11.3 controlled by the autotitrators SET program (by addition of 3.8 mL, 0.1 M NaOH (aq)). At pH=11.3 the peptide was fully dissolved. The activated sidechain 17-((S)-1-Carboxy-3-{2-[2-({2-[2-(2,5-dioxo-pyrrolidin-1-yloxycarbonylmethoxy)ethoxy]-ethylcarbamoyl}-methoxy)-ethoxy]ethylcarbamoyl}propylcarbamoyl)-heptadecanoic acid (55 mg, 66 μmol, 2 eq) was dissolved in NMP (250 μL) and transferred to a 250 μL Hamilton syringe. By the action of an automated syringe pump 250 μL (2.0 eq) of this solution was added over 10 minutes. After additional 60 minutes a sample (10 μL) was taken out, diluted by 90 μL MeCN—$H_2O$ (1:1) HPLC showed a major peak of N26

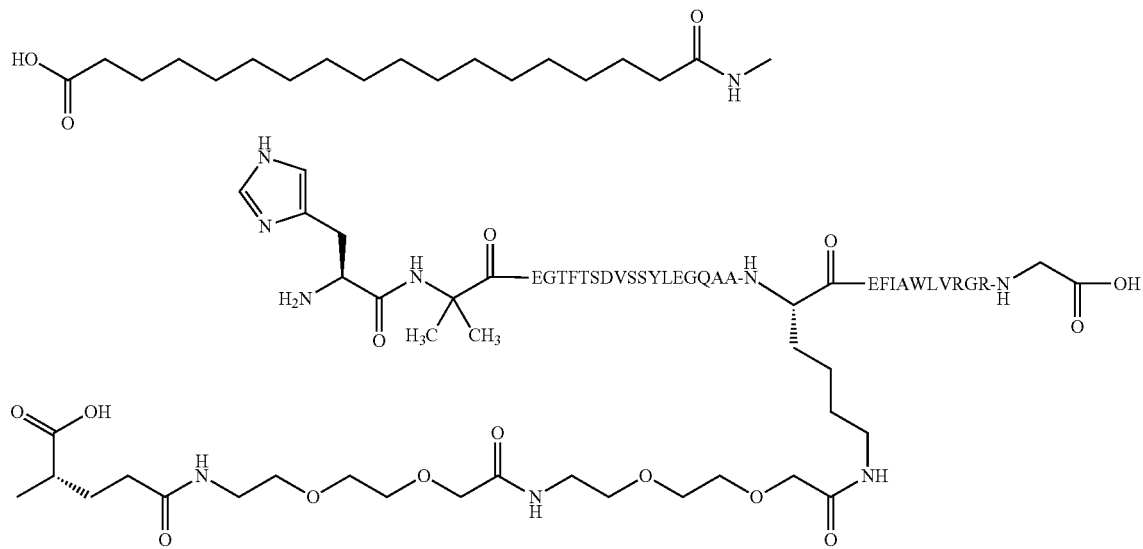

[Arg34]GLP-1-(11-37) prepared via recombinant technique (100 mg, 0.033 mmol) dissolved in 2 mL water was added DIPEA (113 μL, 0.66 mmol) and stirred for 10 min whereupon 17-((S)-1-carboxy-3-{2-[2-({2-[2-(2,5-dioxo-pyrrolidin-1-yloxycarbonyl-methoxy)-ethoxy]-ethylcarbamoyl}-methoxy)-ethoxy]-ethylcarbamoyl}-propyl-carbamoyl)-heptadecanoic acid (55 mg, 0.066 mmol) (Prepared in accordance with example 2, 3 and 13) was added in small portions over 15 min. The mixture was stirred for 60 min before $Na_2HPO_4 \times 7H_2O$ (353.9 mg, 1.32 mmol) was added acylated product (appr. 95%)+trace of unreacted peptide+trace of hydrolysed side chain.

Ligation: Tetrapeptide NHS ester Fmoc-His-Aib-Glu-Gly-OSu (123 mg, 165 μmol, 5 eq) was dissolved in NMP (250 μL). The pH of the reaction mixture was adjusted to 6.9 with dilute acetic acid. Then pH was adjusted to 7.0 by the pH-stat function on the titrator. The 250 μL of NHS ester was added over 20 minutes. The pH was stabilized on pH=7.0±0.1.

Sample taken out after additional 30 min and HPLC showed a 1:1 ratio of the acylated intermediate and the expected product (with Fmoc protection in the N-terminal position).

Another 5 eq of the tetrapeptide NHS ester was added as above. The solution was left stirring for 16 h. The ratio was now 2:8 of the acylated intermediate and the product.

Another 2.5 eq (Total of 12.5 eq) of the tetrapeptide NHS ester was added as above. The solution was left stirring for 16 h. Ratio was now approx. 1:9 of the acylated intermediate and the product.

Piperidine (1.6 mL) was added to the reaction mixture and stirring continued for 1 h.

HPLC showed full deprotection. The crude product was purified on reverse phase HPLC to yield 62 mg (45%) of the wanted product (98% pure).

LCMS:m/z=1372.5 $(M+3H)^{3+}$

Example 20

Preparation of
Fmoc-His(Boc)-Aib-Glu(O-Tbu)-Gly-OH

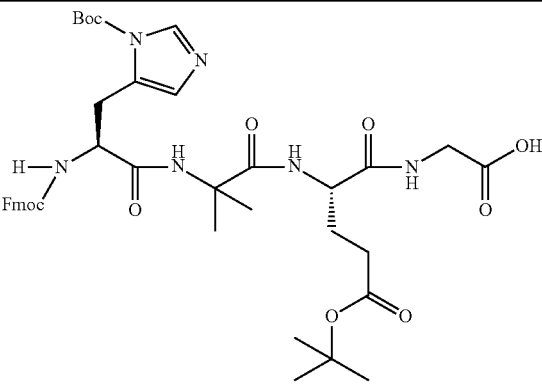

| | Name | Dens [g/ml] | Mw [g/mol] | Mol Ratio | n [mmol] | W [g] | V ml | |
|---|---|---|---|---|---|---|---|---|
| | Product: C41H52N6O11 | | 804.905 | 1 | 98 | 78.9 | | |
| $1^{st}$ AA | 2-chlorotritylchloride resin 1% DVB | | | 1 | 98 | 140 | | |
| | Fmoc-Gly-OH | | 297.3 | 2 | 196 | 58.3 | | |
| | DIPEA | 0.76 | 129.3 | 2 | 196 | | 66.7 | pH 9 |
| | Subst. Fmoc-Gly-resin: 0.7 mmol/g | | | | | | | |
| $2^{nd}$ AA | Fmoc-Glu(OtBu)-OH | | 425.5 | 2 | 196 | 86.9 | | |
| | TCTU | | 355.5 | 2 | 196 | 69.7 | | |
| | DIPEA | 0.76 | 129.3 | 2 | 196 | | 66.7 | |
| | Fmoc-Glu(OtBu)-OH | | 425.5 | 0.5 | 49 | 21.7 | | Re-coupling |
| | TCTU | | 355.5 | 0.5 | 49 | 17.4 | | |
| | DIPEA | 0.76 | 129.3 | 0.5 | 49 | | 17.6 | |
| $3^{th}$ AA | Fmoc-Aib-OH | | 325.4 | 2 | 196 | 63.8 | | |
| | TCTU | | 355.5 | 2 | 196 | 69.7 | | |
| | DIPEA | 0.76 | 129.3 | 2 | 196 | | 66.7 | |
| $4^{th}$ AA | Fmoc-His(boc)-OH | | 477.5 | 2 | 196 | 93.6 | | |
| | TCTU | | 355.5 | 2 | 196 | 69.7 | | |
| | DIPEA | 0.76 | 129.3 | 2 | 196 | | 66.7 | |

Loading of Glycine

The resin was pre-swelled in DCM (1 liter, 20 min) before it was added a solution of Fmoc-Gly-OH and DIPEA in 500 mL DCM, and agitated for 60 min. The resin was washed with DMF (2×500 mL) and 2×500 mL DCM-MeOH-DIPEA (80:15:5, 10 min) then DMF (3×500 mL), DCM (500 mL) and left overnight at RT.

Coupling 1

20% piperidine in DMF (500 mL) for 50 min. was used for Fmoc deprotection, then the resin was washed with DMF (8×500 mL).

Fmoc-Glu(OtBu)-OH and TCTU were dissolved in 700 mL DMF added to reactor and DIPEA was added. The mixture was stirred for 6 h. According HPLC test free amine groups was still present; coupling was repeated using ¼ of reagents. When coupling reaction was finished (no amino groups present), resin was washed with DMF (4×500 mL)

Coupling 2

Fmoc-Aib-OH and TCTU were dissolved in 700 mL DMF solution, put into the reactor and DIPEA was added. The mixture was stirred for 50 min. When coupling reaction was finished (no amino groups present), resin was washed with DMF (4×500 mL).

Coupling 3

20% piperidine in DMF (500 mL) for 30 min was used for Fmoc deprotection, and then the resin was washed with DMF (8×500 mL).

Fmoc-His(Boc)-OH and TCTU were dissolved in 700 mL DMF, solution put into the reactor and DIPEA was added. The mixture was stirred for 50 min. When coupling reaction was finished (no amino groups present), resin was washed with DMF (3×500 mL) and DCM (2×500 mL).

$1^{st}$ Cleavage

The $1^{st}$ cleavage was done using ⅐ of resin. Trifluoroethanol-DCM (1:4, 500 mL) was added and the resin was agitated for 70 min. The filtrate was collected and the solvent was removed in vacuum to give oil. The oil was dissolved in ethyl acetate and left stay in refrigerator to form crystals. Crystals were filtrated, washed using diethyl ether and dried on air, to give 6.1 g of product (yield 45%), purity by HPLC 99.0%.

2$^{nd}$ Cleavage

The 2$^{nd}$ cleavage was done using 3/7 of resin. Trifluoroethanol-DCM (1:4, 1000 mL) was added and the resin was agitated for 90 min. The filtrate was collected and the solvent was removed in vacuum to give oil. The oil was dissolved in ethyl acetate and left stay in refrigerator overnight to form crystals. Crystals were filtrated, washed by diethyl ether and dried on air, to give 33.1 g of product (yield 80%), purity by HPLC 98.7%.

Yield: 6.1 g (45%)

ESI+MS m/z: 805.1 (M+H)$^+$, 1610.7 (2M+H)$^+$.

HPLC R$_t$ (Luna 4.6×250, 5 ul, 100A; acetonitrile/buffer* 30:70 to 60:40, 30 min, 1 ml/min., 220 nm): 23.31 min.; purity 99.0% and 33.1 g (80%)

ESI+MS m/z: 805.1 (M+H)$^+$, 1610.8 (2M+H)$^+$.

HPLC R$_t$ (Luna 4.6×250, 5 ul, 100A, acetonitrile/buffer* 30:70 to 60:40, 30 min, 1 ml/min., 220 nm): 23.16 min.; purity 98.7%

*buffer: 2.71 g KH$_2$PO$_4$, 7.13 g NaH$_2$PO$_4$.2H$_2$O dissolved in H$_2$O (2 L);

Example 21

Preparation of Fmoc-his-Aib-Glu-Gly-Osuc, Tfa Salt

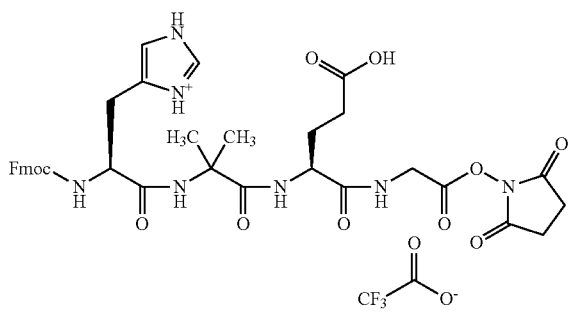

Fmoc-His(Boc)-Aib-Glu(O-tBu)-Gly-OH (1.25 g, 1.56 mmol) was dissolved in THF (10 mL) and were added DIPEA (0.64 g, 3.73 mmol) and TSTU (0.56 g, 1.87 mmol, 1.2 eq). The mixture was stirred over night.

LCMS: app. 95% conversion. The mixture was filtered and the solvent was removed in vacuo. EtOAc (100 mL) was added and the organic phase was washed twice with cold 0.1 N HCl and dried over Na$_2$SO$_4$, filtered and evaporated to give crude Fmoc-His(Boc)-Aib-Glu(OtBu)-Gly-OSu (1.1 g, 79%). The crude product was dissolved in DCM (2 mL) and added TFA (1 mL). Stirred for 1 h. LCMS: 100% deprotected. After evaporation of the organic solvent ice-cold diethylether was added to the residue and the resulting precipitate was collected by filtration and dried in a vacuum oven to give Fmoc-His-Aib-Glu-Gly-OSu (430 mg)

LCMS:m/z=746.3 (M+H)$^+$

Example 22

Preparation of 3-(1-trityl-1H-imidazol-4-yl)-propionic acid 2,5-dioxo-pyrrolidin-1-yl ester

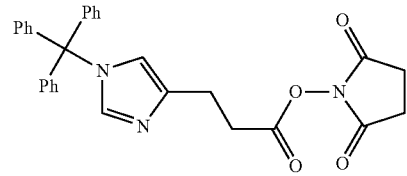 [SMILES: O=C(CCc1cn(C(c2ccccc2)(c2ccccc2)c2ccccc2)cn1)ON1C(=O)CCC1=O]

3-(N-Tritylimidazol-4-yl)propionic acid (Jung et al., Bioorg. Med. Chem. Lett., 6, 2317-2336, 1998) (50 g, 0.13 mol) was dissolved in DCM (500 ml), N-hydroxysuccinimide (24 g, 0.209 mol) and N,N'-dicyclohexylcarbodiimide (35 g 0.170 mol) was added, while maintaining the internal temperature below 30° C. with an icebath. The resulting mixture was stirred at room temperature overnight. The mixture was filtered and the resulting solution was concentrated in vacuo, re-dissolved in THF (350 ml) upon heating and mixed with 2-propanol (350 ml) to a resulting temperature of 32° C., then cooled to 5° C. The crystalline product was filtered and washed with 2-propanol (150 ml) and dried in vacuum to afford the title compound (47.3 g, yield 75%).

$^1$H NMR (D$_6$-DMSO, 400 MHz): δ 7.15-6.99 (m, 9H), 6.82 (s, 1H), 6.81-6.62 (m, 6H), 6.38 (s, 1H), 2.63 (t, 3H), 2.4 (m, 6H).

Example 23

Preparation of 4-[2-(2,5-dioxo-pyrrolidin-1-yloxycarbonyl)-ethyl]-1H-imidazol-1-ium trifluoroacetate

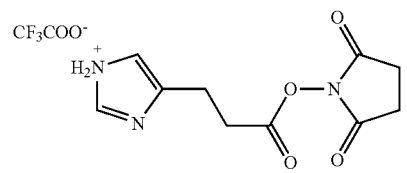 [SMILES: "CF3COO-" ; O=C(CCc1c[nH]cn1)ON1C(=O)CCC1=O]

3-(1-Trityl-1H-imidazol-4-yl)-propionic acid 2,5-dioxo-pyrrolidin-1-yl ester (40 g, 83 mmol) was dissolved in DCM (240 ml). Triisopropylsilane (42 ml) and trifluoroacetic acid (240 ml) was added and the resulting solution was stirred at room temperature for 90 min. The solution was evaporated in vacuo, redissolved in acetonitrile (120 ml), and tert-butylmethyl ether (290 ml) was added dropwise and the solution was cooled to 8° C. The precipitate was collected by filtration and dried in vacuum to afford a white compound (24 g, 82%).

$^1$H NMR (D$_6$-DMSO, 400 MHz): δ 8.90 (s, 1H), 7.47 (s, 1H), 3.09 (t, 2H), 2.79 (t, 2H), 2.79 (s, 4H).

Example 24

Alternative preparation of GLP-1 analogue N-epsilon37-[2-(2-{2-[2-(2-{2-[(S)-4-Carboxy-4-({trans-4-[(19-carboxynonadecanoylamino)methyl]cyclohexanecarbonyl}amino)-butyrylamino]ethoxy}ethoxy)acetylamino]ethoxy}ethoxy)acetyl]-[DesaminoHis7,Glu22,Arg26,Arg34,Lys37]GLP-1-(7-37) peptide

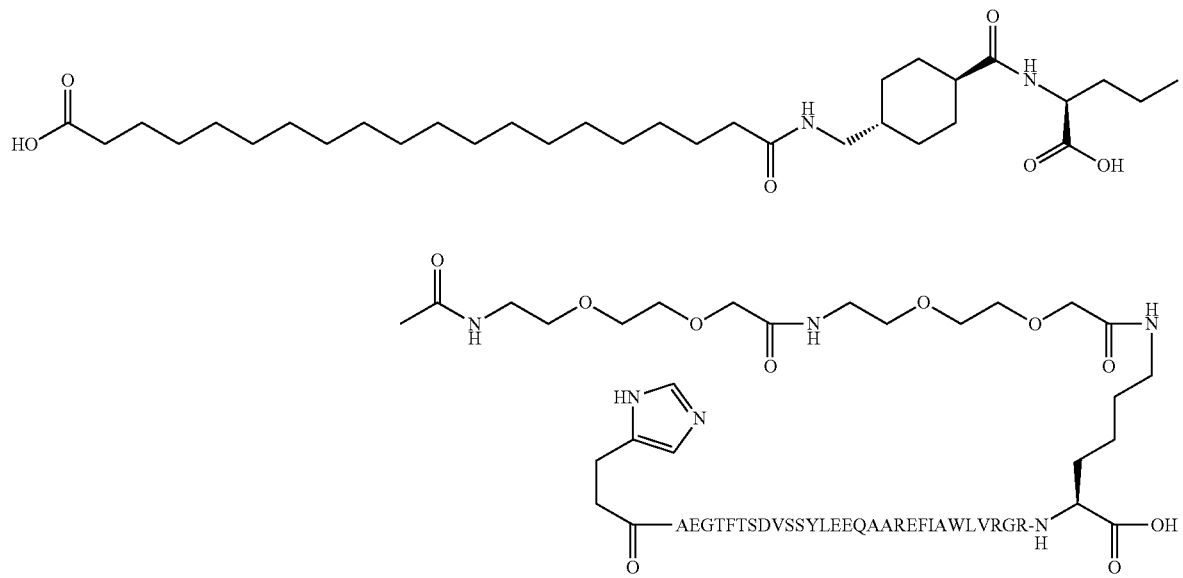

[Glu22,Arg26,Arg34,Lys37]GLP-1-(8-37) peptide (80 g, 0.023 mol) prepared via recombinant technique was dissolved in water (6400 ml) and triethylamine (28 ml) was added to pH 11.0. (22S)-22-{[(trans-4-{[(19-carboxynonadecanoyl)amino]methyl}-cyclohexyl)carbonyl]amino}-1-[(2,5-dioxo-1-pyrrolidinyl)oxy]-1,10,19-trioxo-3,6,12,15-tetraoxa-9,18-diazatricosan-23-oic acid (34.9 g, 0.035 mol) was dissolved in NMP (210 ml) and added to the solution over 2 hr., while maintaining the pH between 11.0-11.1 by continuous addition of triehylamine. The pH was adjusted to 7.0 by addition of 1M sulphuric acid (aq, 140 ml). 4-[2-(2,5-Dioxo-pyrrolidin-1-yloxycarbonyl)-ethyl]-1H-imidazol-1-ium trifluoroacetate (36.99 g, 0.105 mol) was dissolved in NMP and added to the solution over 2 hr. while maintaining the pH at 7.0-7.1 by continuously addition of triethylamine. The pH was adjusted to 11.2 by addition of 1 M NaOH (aq, 500 ml) and the solution was stirred at room temperature for 7 hr. pH was adjusted to 7.4 by addition of 1M sulphuric acid (aq, 140 ml), to a total of 7973.8 g which was purified by preparative HPLC.

LCMS: m/z=1476 (M+3H)$^{3+}$

Example 25

Preparation of [Aib8,Arg34]GLP-1-(7-37) peptide

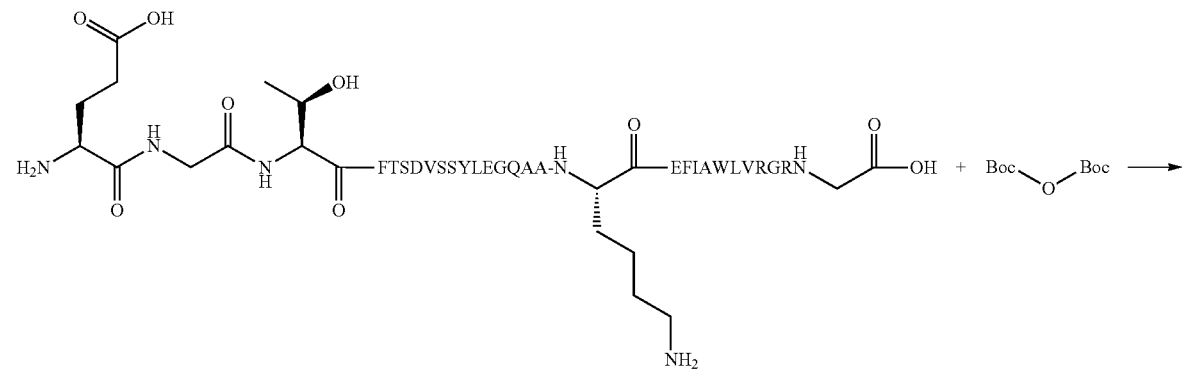

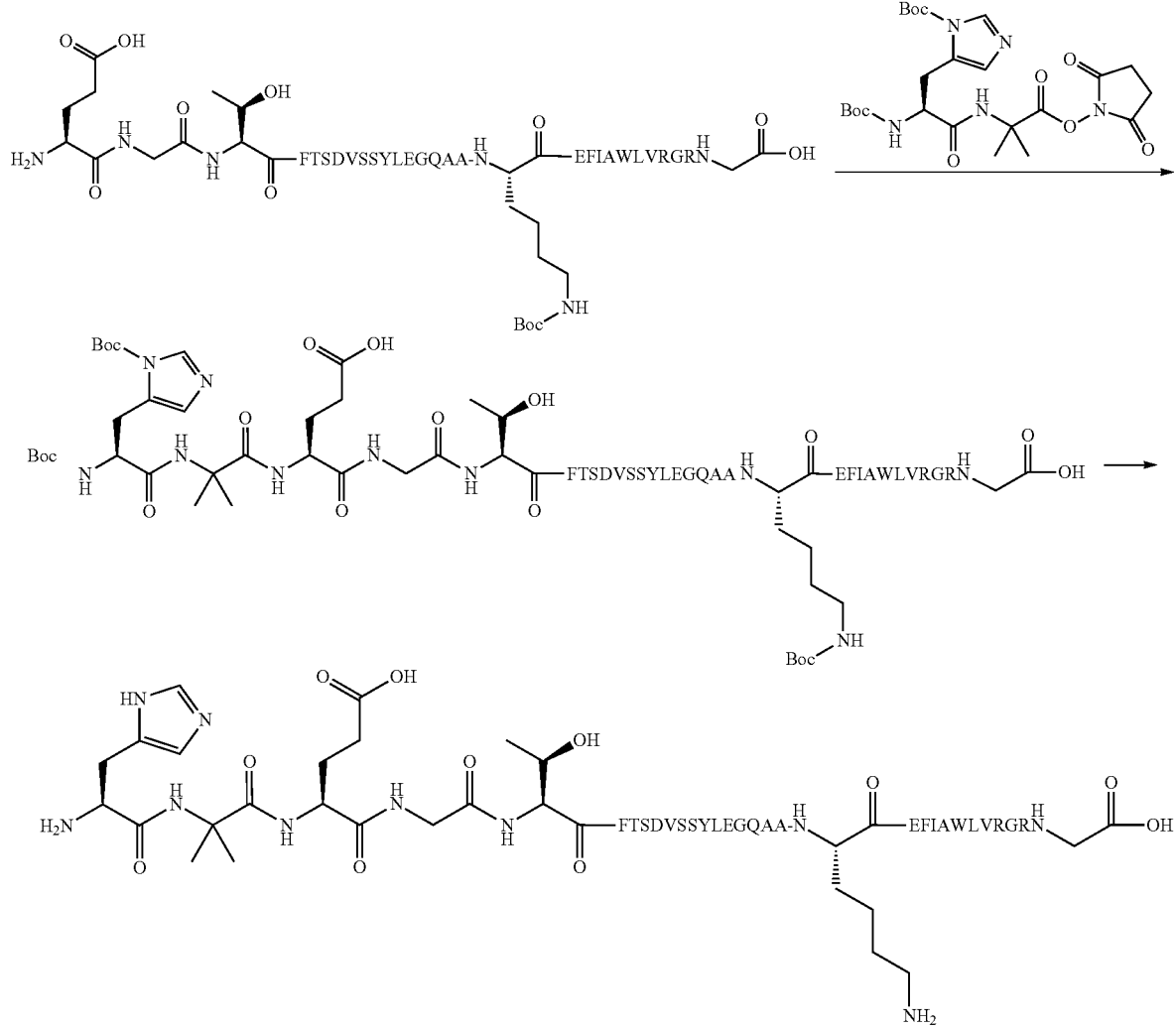

Arg34-GLP-1[9-37]•4TFA (103 mg; 0.028 mmol) was dissolved in 2 mL water and transferred to a titrator reaction chamber with additional 2×1 mL water. The reaction chamber was equipped with a stirring magnet, pH electrode and a titrant tube. The pH of the solution was 1.9. The titrator was programmed to a 'STAT' method at fixed pH=11.3. The titrant, sodium hydroxide (3.27 mL, 0.1 M aq), was added by the titrator to reach pH=11.3. (Boc)$_2$O (186 mg, 0.85 mmol, 3 eq) was dissolved in NMP (2.500 mL) and a 250 µL Hammilton syringe was filled with this solution (i.e. 250 µL; 18.6 mg (Boc)$_2$O, 3 eq).

Water (1.0 mL) was added to the reaction chamber to make a total volume of 8.3 mL and the (Boc)$_2$O NMP solution was then added over 20 min by aid of a syringe pump at room temperature. The titrator was keeping the pH=11.3 by automatic addition of the titrant. After stirring for additional 10 minutes LCMS showed 88% of the Lys26 (NHBoc) product together with a diboc product (9%) and starting material (3%). The pH of the solution was adjusted to 6.5 with a small volume of dilute HOAc (aq) and the titrator was set at pH=7.5 for the further reaction.

A solution of Boc-His(Boc)-Aib-OSu (305 mg, 0.568 mmol, 20 eq) was dissolved in NMP (500 µL) giving a total volume of 715 µL. Of this solution 2×250 µL (2×7 eq) was added to the reaction mixture over 2×30 minutes keeping pH=7.5. Immediate precipitation of the Boc-His(Boc)-Aib-OSu was observed, but upon stirring all dissolved. After end of addition the mixture was stirred for another 2 h at pH=7.5 and at room temperature to allow dissolution and reaction of the reactant.

The mixture was lyophilized and treated with TFA containing 3% TIPS and 3% water for 2 h. The solvents were evaporated and the residue was purified by HPLC to give the desired product.

LCMS m/z: 849.88 (M+4H)$^{4+}$, 1132.86 (M+3H)$^{3+}$. Calcd. 3396.698 (M+H)$^+$.

Example 26

Preparation of Boc-His(Boc)-Aib-OH

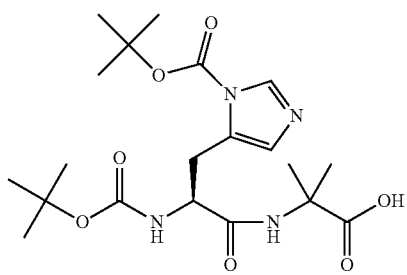 [SMILES: CC(C)(C)OC(=O)N[C@@H](Cc1cncn1C(=O)OC(C)(C)C)C(=O)NC(C)(C)C(=O)O]

Loading of Aib: 2-Chlortritylchloride resin 1% DVB (Load 1.1 mmol/g) (10.0 g, 11 mmol) was pre-swelled in DCM before it was added a solution of Fmoc-Aib-OH (7.16 g, 22 mmol) and DIPEA (9.4 mL, 55 mmol) in DCM (100 mL). The mixture was agitated for 60 min. The resin was washed with NMP (2×100 mL) and DCM-MeOH-DIPEA (80:15:5) (2×100 mL, 10 minutes each), and NMP (3×100 mL). The washed resin was treated with 20% piperidine in NMP (3×100 mL, 10 min each). The resin was washed with NMP (6×100 mL).

Coupling: Boc-His(Boc)-OH (15.64 g, 44 mmol) was dissolved in NMP (100 mL) and DCM (20 mL) and HOBt (5.95 g, 44 mmol) was added followed by slow addition of DIC (6.81 mL, 44 mmol). The mixture was stirred for 15 min before DIPEA (9.40 mL, 55 mmol) was added. The activated mixture was added to the resin and the resin was agitated for 16 h before it was washed with NMP (4×100 mL) and DCM (10×100 mL).

Cleavage: Trifluoroethanol-DCM (1:4, 100 mL) was added and the resin was agitated for 1 hour. The filtrate was collected and a new portion of trifluoroethanol-DCM (1:4, 100 mL) was added and agitated for 15 min and the filtrate was collected. The combined filtrates were evaporated in vacuo and petrolether (50 mL) was added. The resulting precipitate was washed with petrolether, collected and dried in vacuum oven for 16 h at 40° C. to give Boc-His(Boc)-Aib-OH (1.00 g, yield 21%, purity 95%).

LCMS m/z: 441.18 (M+H)$^+$. Calcd. 440.227 (M+H)$^+$.

Example 27

Preparation of Boc-His(Boc)-Aib-Osu

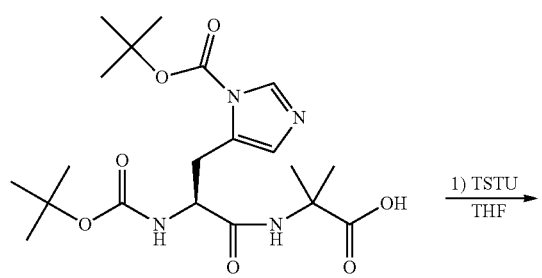

Boc-His(Boc)-Aib-OH (0.70 g, 1.59 mmol) was dissolved in THF (5.0 mL) and TSTU (1.44 g, 4.77 mmol) and DIPEA (1.36 mL, 7.95 mmol) was added. The reaction mixture was stirred at rt. for 2 h. LCMS showed almost complete conversion into the oxazolone product. The reaction mixture was filtered and the solvent was evaporated. The residue was re-dissolved in DCM (10 mL) and N-hydroxysuccinimide (292 mg, 2.56 mmol, 1.6 eq) was added. The mixture was stirred over night at room temperature. HPLC show a major peak of the desired Su-ester (85%), trace of un-reacted starting material and 5% of the ring-closed oxazolone. The solvent was evaporated at room temperature under reduced pressure and H$_2$O (25 mL) was added to dissolve unreacted N-hydroxysuccinimide. The H$_2$O was decanted off and the residue was dissolved in EtOAc (100 mL) dried over MgSO$_4$, filtered and evaporated to give a white foam containing 70% of the desired product.

LCMS m/z: 538.18 (M+H)$^+$. Calcd. 538.251 (M+H)$^+$

Example 28

Preparation of Fmoc-his-Aib-Osu

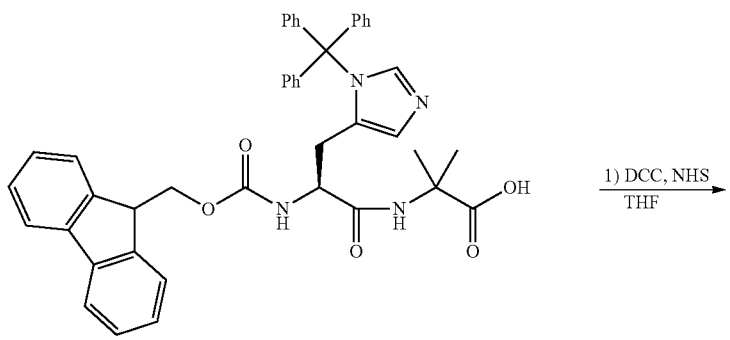

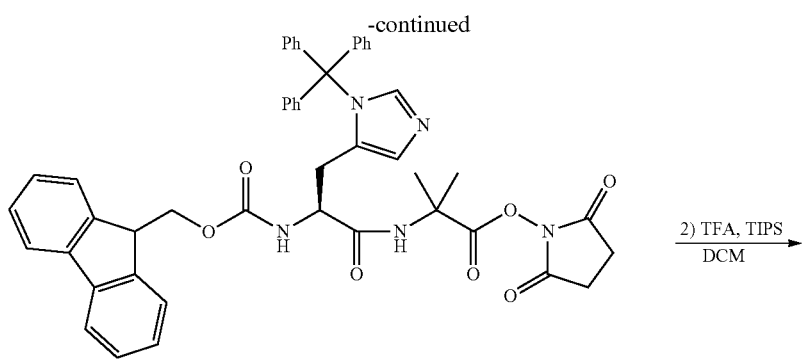

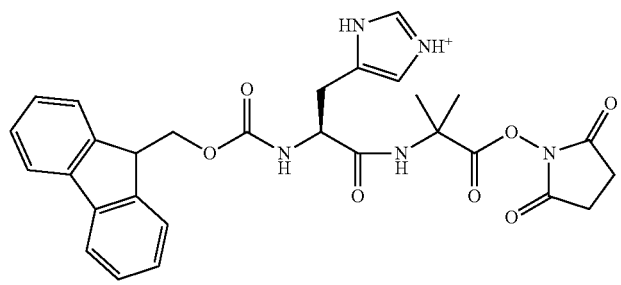

Fmoc-His(Trt)-Aib-OH (5 g, 7.1 mmol) was dissolved in THF (50 ml). DCC (1.61 g, 7.8 mmol) and NHS (0.94 g, 8.2 mmol) was added and the resulting solution was stirred for 16 hr at room temperature. The DCU was filtered and the solution was evaporated in vacuo. The resulting oil was dissolved in DCM (34 ml) and trifluoroacetic acid (34 ml) and TIPS (6 ml) was added. The solution was stirred for 2 hr at room temperature, evaporated in vacuo to 25 ml, added dropwise to TBME (200 ml), stirred for 60 min, and the resulting white percipetate is collected by filtration, and washed with additional TBME. The collected precipitate was dried in vacuum for 16 hr.

LCMS: m/z=560 (M+H)$^+$

Example 29

Preparation of GLP-1 derivative [Aib8,Arg34]GLP-1-(7-37) Peptide

[Arg34] GLP-1(9-37) peptide•4TFA (103 mg; 0.028 mmol) was dissolved in 0.1 M TEA(aq., 7.5 ml) additional TEA was added (140 µl) to a resulting pH of 11.28. FmocOSu (90 mg) was dissolved in NMP (1600 µl) and 334 µl (0.055 mmol) of this solution was added dropwise to the aqueous peptide solution. pH was adjusted to 7 by addition of 1M H$_2$SO$_4$(aq). FmocHisAibOSu trifluoroacetate salt (90 mg, 0.134 mmol) was dissolved in NMP (800 µl) and added dropwise to the solution while maintaining the pH between 7.0 and 7.5 by continuos addition of 1M NaOH(aq). Piperidin (2 ml) was added and the resulting solution was stirred for 60 min. at room temperature. TBME (5 ml) was added and the mixture was stirred for 30 min. The aqueous phase was separated and lyophilised.

LCMS: m/z=1134 (M+3H)$^{3+}$

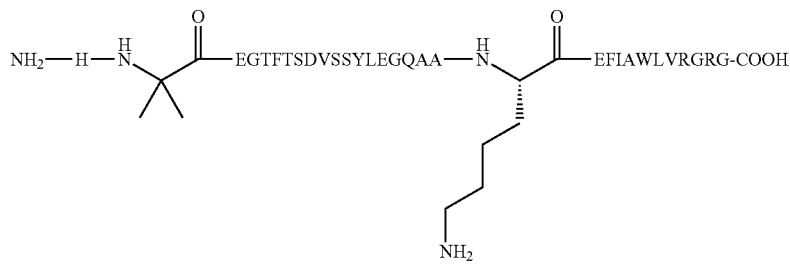

The invention claimed is:

1. A method for making a derivative of a glucagon-like peptide-1 (GLP-1) analogue comprising one or more non-proteogenic amino acids in the N-terminal part, said method comprising the steps of:
   i) culturing a host cell comprising a nucleotide sequence encoding a precursor molecule of said GLP-1 derivative under suitable conditions for expression of said precursor molecule,
   ii) separating the expressed precursor molecule from the culture broth,
   iii) acylating an epsilon amino group of at least one lysine residue in the expressed precursor molecule with an acylating agent, which is optionally activated, to obtain a precursor molecule derivative, and optionally isolating said precursor molecule derivative, wherein the acylation step takes place in an aqueous solvent mixture and the pH in the reaction mixture is between 9 and 13,
   iv) coupling a N-terminal amino acid extension of 1, 2, 3 or 4 amino acids in length comprising 1, 2, 3, or 4 non-proteogenic amino acids to the expressed precursor molecule derivative, and
   v) isolating the resulting derivative of a GLP-1 analogue; wherein the GLP-1 analogue is [Aib8,Arg34]GLP-1-(7-37);
   wherein said one or more non-proteogenic amino acids in the N-terminal amino acid extension are moieties which can be incorporated into a peptide via peptide bonds but is not a proteogenic amino acid that is selected from the group consisting of Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, and Valine;
   wherein the acylating agent is a carboxylic acid analogue of the general formula selected from the group consisting of A-OH, A-C-D-OH, A-B-C-OH and A-B-C-D-OH, which is optionally activated and/or protected with one or more protection group(s), wherein,
   A is selected from the group consisting of

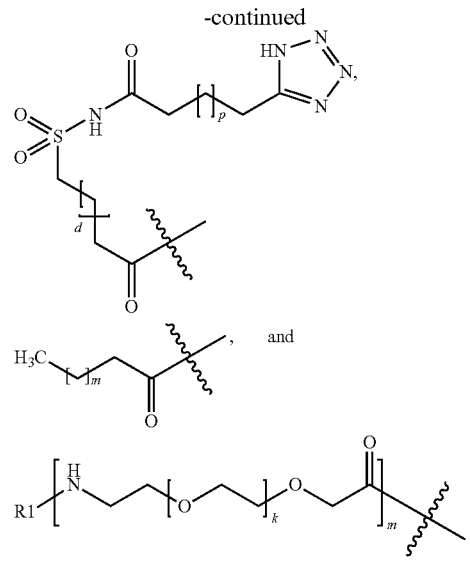

wherein n is selected from the group consisting of 14, 15, 16 17, 18 and 19;

p is selected from the group consisting of 10, 11, 12, 13 and 14;

d is selected from the group consisting of 0, 1, 2, 3, 4 and 5;

m is selected from the group consisting of 11, 12, 13, 14, 15, 16, and 17;

k is selected from the group consisting of 0, 1, 2, 3, 4, 5, 11 and 27;

m' is selected from the group consisting of 0, 1, 2, 3, 4, 5 and 6; and

R1 is a generally accepted protection group;

B is selected from the group consisting of

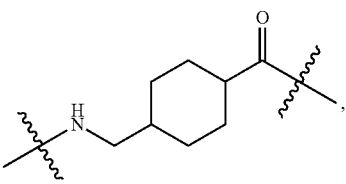

113

-continued

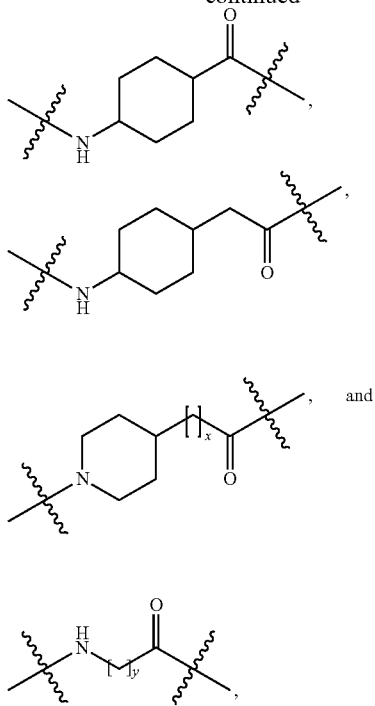

wherein
x is selected from the group consisting of 0, 1, 2, 3 and 4; and
y is selected from the group consisting of 1, 2, 3, 4, 5, 6, 7, 8, 9, 10, 11 and 12;

114

C is selected from the group consisting of

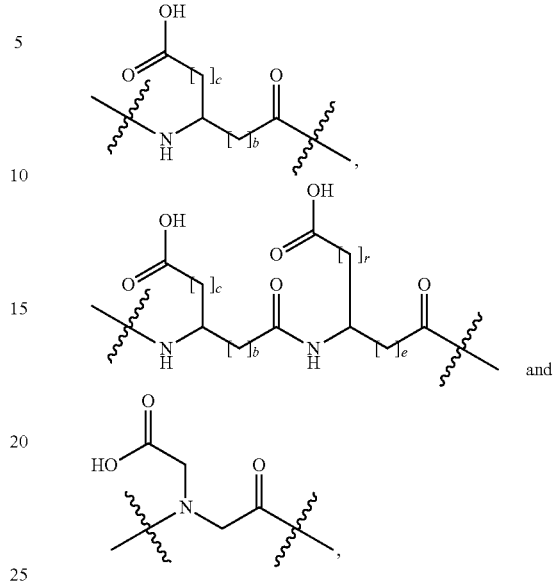

wherein b and e are each independently selected from the group consisting of 0, 1 and 2, and c and f are each independently selected from the group consisting of 0, 1 and 2 with the proviso that b is 1 or 2 when c is 0, or b is 0 when c is 1 or 2, and e is 1 or 2 when f is 0, or e is 0 when f is 1 or 2;

wherein, when one or more free carboxylic acid(s) are present, they are optionally protected with a generally accepted protection group; and D is selected from the group consisting of

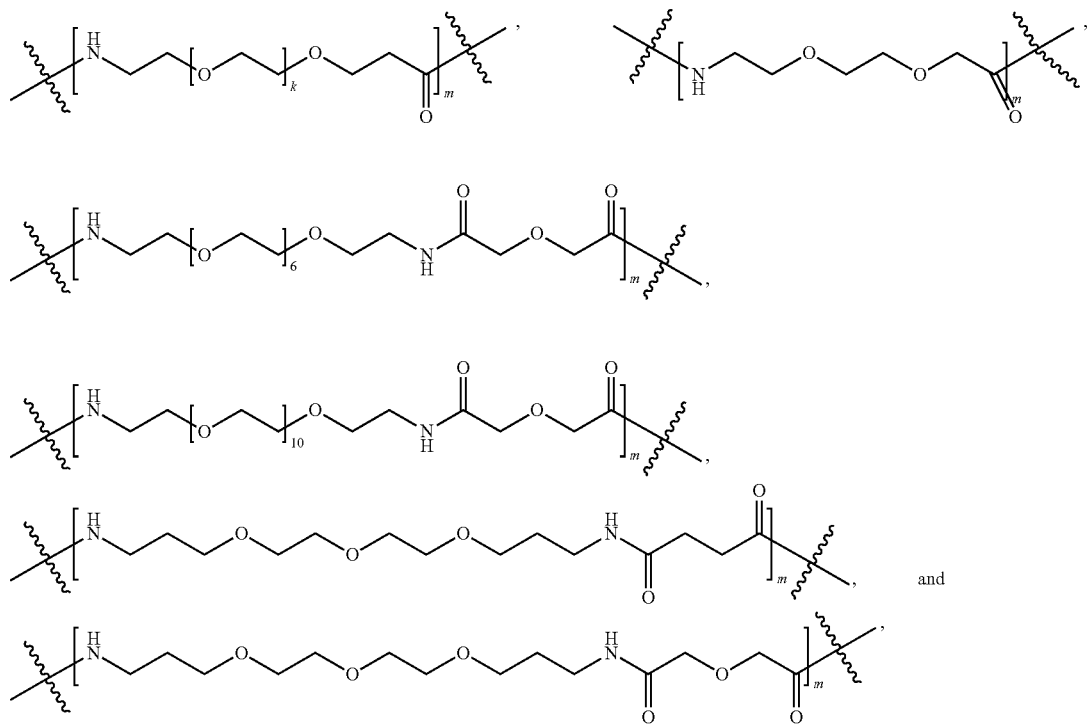

and wherein k is selected from the group consisting of 0, 1, 2, 3, 4, 5, 11 and 27, and m is selected from the group consisting of 0, 1, 2, 3, 4, 5 and 6; and wherein the resulting GLP-1 derivative is resistant to degradation by dipeptidyl peptidase IV (DPP-IV).

2. The method according to claim 1, wherein the host cell is selected from a mammalian host cell, an avian host cell, an insect host cell, a plant host cell, a bacterial host cell, a fungal host cell and a yeast host cell.

3. The method according to claim 1, wherein step (ii) comprises a further step of removing N-terminal and/or C-terminal pro-peptide extensions from the precursor molecule.

4. The method according to claim 1, wherein R1 is selected from the group consisting of 9H-fluoren-9-yl-methoxycarbonyl (Fmoc), tert-butoxycarbonyl (Boc), and Benzylcarbamate (Cbz).

5. The method according to claim 1, wherein the acylating agent is of formula A-C-D-OH, and wherein A-C-D- is selected from the group consisting of:

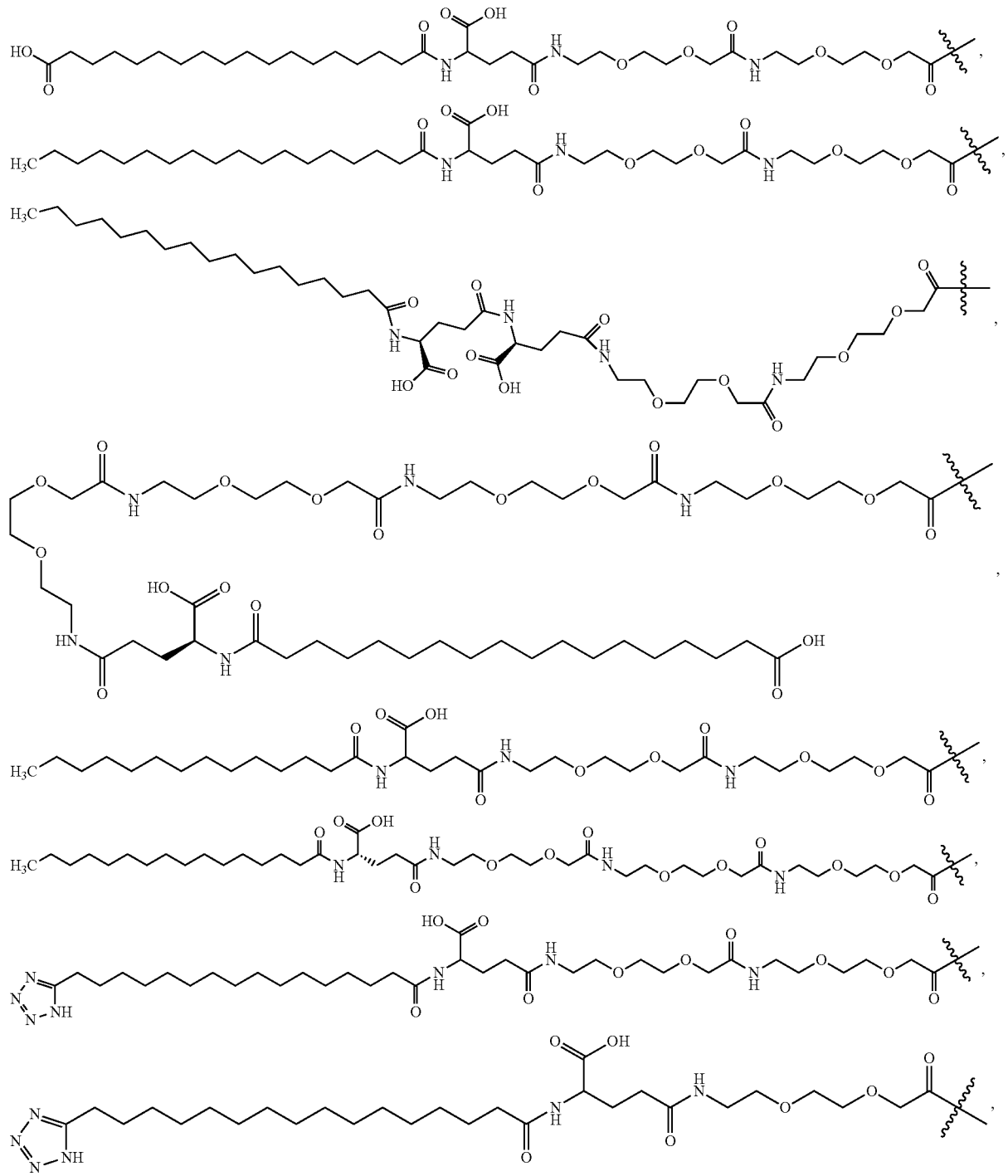

-continued

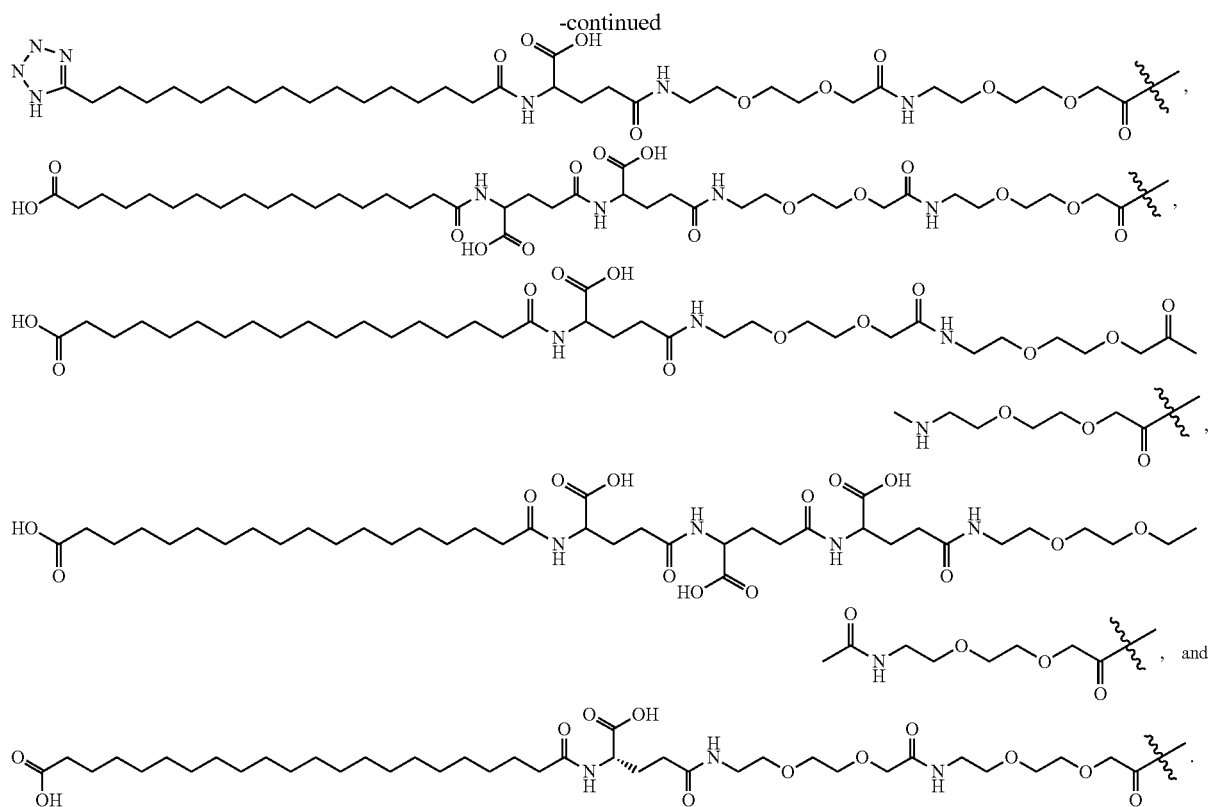

6. The method according to claim 1, wherein the acylating agent is of formula A-C-D-OH, and wherein A-C-D- is

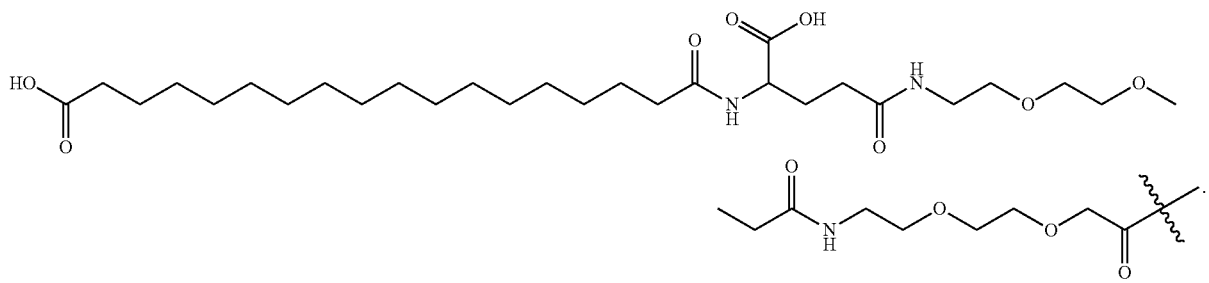

7. The method according to claim 1, wherein said an acylating agent comprises one or more protection groups; and wherein said protection groups are optionally removed from the acylating agent once it has been coupled to the precursor molecule.

8. The method according to claim 1, wherein said acylation step (iii) takes place in an aqueous solvent mixture with a pH between 10 and 12.

9. The method according to claim 1, wherein the coupling of the N-terminal amino acid extension comprising 1, 2, 3 or 4 non-proteogenic amino acids takes place in an organic polar solvent selected from the group consisting of 1-methylpyrrolidin-2-one, acetonitrile, tetrahydrofuran, dimethylsulfoxide, N,N-dimethlyformamide and N-methylformamide.

10. A method according to claim 1, wherein the coupling of the N-terminal amino acid extension comprising 1, 2, 3 or 4 non-proteogenic amino acids takes place in an aqueous solvent mixture.

11. A method according to claim 1, wherein the GLP-1 derivative is N-epsilon26-[2-(2-{2-[2-(2-{2-[(S)-4-Carboxy-4-(17-carboxy-heptadecanoylamino)-butyrylamino] ethoxy }ethoxy)acetylamino]-ethoxy }ethoxy)-acetyl] [Aib8,Arg34]GLP-1-(7-37) peptide.

* * * * *

UNITED STATES PATENT AND TRADEMARK OFFICE
CERTIFICATE OF CORRECTION

PATENT NO. : 9,732,137 B2  
APPLICATION NO. : 12/810934  
DATED : August 15, 2017  
INVENTOR(S) : Jesper Faergeman Lau et al.

Page 1 of 2

It is certified that error appears in the above-identified patent and that said Letters Patent is hereby corrected as shown below:

In the Claims

At Column 112, Claim number 1, Line number 40, please amend as follows:

Delete " " and insert -- --

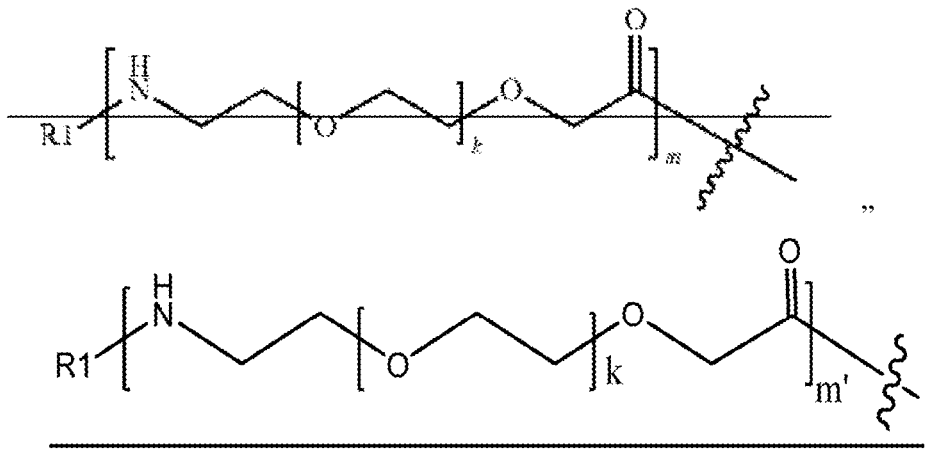

At Column 114, Claim number 1, Line number 13, please amend as follows:

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 9,732,137 B2

Delete " 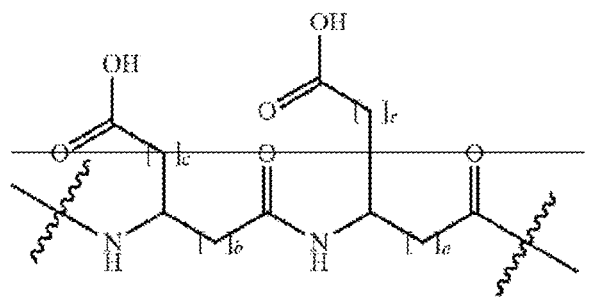 "

And insert -- 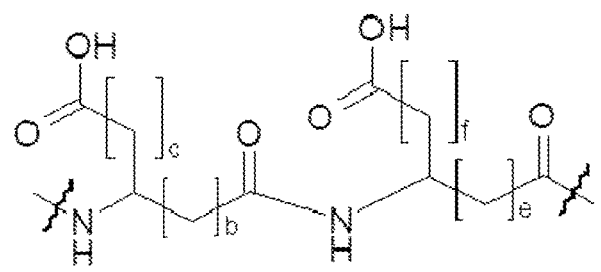 --

SEQUENCE LISTING

<160> NUMBER OF SEQ ID NOS: 46

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly
        35                  40

<210> SEQ ID NO 3
<211> LENGTH: 35
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa in position 6 is Val or Leu
<220> FEATURE:
<221> NAME/KEY: MISC_FEATURE
<222> LOCATION: (8)..(8)
<223> OTHER INFORMATION: Xaa in position 8 is Ser, Lys or Arg
<220> FEATURE:
<221> NAME/KEY: MISC_FEATURE
<222> LOCATION: (9)..(9)
<223> OTHER INFORMATION: Xaa in position 9 is Tyr or Gln
<220> FEATURE:
<221> NAME/KEY: MISC_FEATURE
<222> LOCATION: (10)..(10)
<223> OTHER INFORMATION: Xaa in position 10 is Leu or Met
<220> FEATURE:
<221> NAME/KEY: MISC_FEATURE
<222> LOCATION: (12)..(12)
<223> OTHER INFORMATION: Xaa in position 12 is Gly or Glu
<220> FEATURE:
<221> NAME/KEY: MISC_FEATURE
<222> LOCATION: (13)..(13)
<223> OTHER INFORMATION: Xaa in position 13 is Gln, Glu, Lys or Arg
<220> FEATURE:
<221> NAME/KEY: MISC_FEATURE
<222> LOCATION: (15)..(15)
<223> OTHER INFORMATION: Xaa in position 15 is Ala or Val
<220> FEATURE:
<221> NAME/KEY: MISC_FEATURE
<222> LOCATION: (16)..(16)
<223> OTHER INFORMATION: Xaa in position 16 is Lys, Glu or Arg
<220> FEATURE:
<221> NAME/KEY: MISC_FEATURE
<222> LOCATION: (17)..(17)
<223> OTHER INFORMATION: Xaa in position 17 is Glu or Leu
<220> FEATURE:
<221> NAME/KEY: MISC_FEATURE
<222> LOCATION: (20)..(20)

```
<223> OTHER INFORMATION: Xaa in position 20 is Ala, Glu or Arg
<220> FEATURE:
<221> NAME/KEY: MISC_FEATURE
<222> LOCATION: (23)..(23)
<223> OTHER INFORMATION: Xaa in position 23 is Val, Lys or Arg
<220> FEATURE:
<221> NAME/KEY: MISC_FEATURE
<222> LOCATION: (24)..(24)
<223> OTHER INFORMATION: Xaa in position 24 is Lys, Glu, Asn, His or Arg
<220> FEATURE:
<221> NAME/KEY: MISC_FEATURE
<222> LOCATION: (25)..(25)
<223> OTHER INFORMATION: Xaa in position 25 is Gly
<220> FEATURE:
<221> NAME/KEY: MISC_FEATURE
<222> LOCATION: (26)..(26)
<223> OTHER INFORMATION: Xaa in position 26 is Arg, Gly or Lys
<220> FEATURE:
<221> NAME/KEY: MISC_FEATURE
<222> LOCATION: (27)..(27)
<223> OTHER INFORMATION: Xaa in position 27 is Gly, Ala, Glu, Pro, Lys,
      or is absent
<220> FEATURE:
<221> NAME/KEY: MISC_FEATURE
<222> LOCATION: (28)..(28)
<223> OTHER INFORMATION: Xaa in position 28 is Lys, Ser, or is absent
<220> FEATURE:
<221> NAME/KEY: MISC_FEATURE
<222> LOCATION: (29)..(29)
<223> OTHER INFORMATION: Xaa in position 29 is Ser, Lys, or is absent
<220> FEATURE:
<221> NAME/KEY: MISC_FEATURE
<222> LOCATION: (30)..(30)
<223> OTHER INFORMATION: Xaa in position 30 is Gly, or is absent
<220> FEATURE:
<221> NAME/KEY: MISC_FEATURE
<222> LOCATION: (31)..(31)
<223> OTHER INFORMATION: Xaa in position 31 is Ala, or is absent
<220> FEATURE:
<221> NAME/KEY: MISC_FEATURE
<222> LOCATION: (32)..(32)
<223> OTHER INFORMATION: Xaa in position 32 is Pro, or is absent
<220> FEATURE:
<221> NAME/KEY: MISC_FEATURE
<222> LOCATION: (33)..(33)
<223> OTHER INFORMATION: Xaa in position 33 is Pro, or is absent
<220> FEATURE:
<221> NAME/KEY: MISC_FEATURE
<222> LOCATION: (34)..(34)
<223> OTHER INFORMATION: Xaa in position 34 is Pro, or is absent
<220> FEATURE:
<221> NAME/KEY: MISC_FEATURE
<222> LOCATION: (35)..(35)
<223> OTHER INFORMATION: Xaa in position 35 is Ser, or is absent

<400> SEQUENCE: 3

Thr Phe Thr Ser Asp Xaa Ser Xaa Xaa Xaa Glu Xaa Xaa Ala Xaa Xaa
1               5                   10                  15

Xaa Phe Ile Xaa Trp Leu Xaa Xaa Xaa Xaa Xaa Xaa Xaa Xaa Xaa Xaa
            20                  25                  30

Xaa Xaa Xaa
        35

<210> SEQ ID NO 4
<211> LENGTH: 37
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa in position 1 is Glu or Asp
<220> FEATURE:
<221> NAME/KEY: MISC_FEATURE
```

```
<222> LOCATION: (2)..(2)
<223> OTHER INFORMATION: Xaa in position 2 is Gly or Ala
<220> FEATURE:
<221> NAME/KEY: MISC_FEATURE
<222> LOCATION: (8)..(8)
<223> OTHER INFORMATION: Xaa in position 8 is Val or Leu
<220> FEATURE:
<221> NAME/KEY: MISC_FEATURE
<222> LOCATION: (10)..(10)
<223> OTHER INFORMATION: Xaa in position 10 is Ser, Lys or Arg
<220> FEATURE:
<221> NAME/KEY: MISC_FEATURE
<222> LOCATION: (11)..(11)
<223> OTHER INFORMATION: Xaa in position 11 is Tyr or Gln
<220> FEATURE:
<221> NAME/KEY: MISC_FEATURE
<222> LOCATION: (12)..(12)
<223> OTHER INFORMATION: Xaa in position 12 is Leu or Met
<220> FEATURE:
<221> NAME/KEY: MISC_FEATURE
<222> LOCATION: (14)..(14)
<223> OTHER INFORMATION: Xaa in position 14 is Gly or Glu
<220> FEATURE:
<221> NAME/KEY: MISC_FEATURE
<222> LOCATION: (15)..(15)
<223> OTHER INFORMATION: Xaa in position 15 is Gln, Glu, Lys or Arg
<220> FEATURE:
<221> NAME/KEY: MISC_FEATURE
<222> LOCATION: (17)..(17)
<223> OTHER INFORMATION: Xaa in position 17 is Ala or Val
<220> FEATURE:
<221> NAME/KEY: MISC_FEATURE
<222> LOCATION: (18)..(18)
<223> OTHER INFORMATION: Xaa in position 18 is Lys, Glu or Arg
<220> FEATURE:
<221> NAME/KEY: MISC_FEATURE
<222> LOCATION: (19)..(19)
<223> OTHER INFORMATION: Xaa in position 19 is Glu or Leu
<220> FEATURE:
<221> NAME/KEY: MISC_FEATURE
<222> LOCATION: (22)..(22)
<223> OTHER INFORMATION: Xaa in position 22 is Ala, Glu or Arg
<220> FEATURE:
<221> NAME/KEY: MISC_FEATURE
<222> LOCATION: (25)..(25)
<223> OTHER INFORMATION: Xaa in position 25 is Val, Lys or Arg
<220> FEATURE:
<221> NAME/KEY: MISC_FEATURE
<222> LOCATION: (26)..(26)
<223> OTHER INFORMATION: Xaa in position 26 is Lys, Glu, Asn, His or Arg
<220> FEATURE:
<221> NAME/KEY: MISC_FEATURE
<222> LOCATION: (27)..(27)
<223> OTHER INFORMATION: Xaa in position 27 is Gly
<220> FEATURE:
<221> NAME/KEY: MISC_FEATURE
<222> LOCATION: (28)..(28)
<223> OTHER INFORMATION: Xaa in position 28 is Arg, Gly or Lys
<220> FEATURE:
<221> NAME/KEY: MISC_FEATURE
<222> LOCATION: (29)..(29)
<223> OTHER INFORMATION: Xaa in position 29 is Gly, Ala, Glu, Pro, Lys,
     or is absent
<220> FEATURE:
<221> NAME/KEY: MISC_FEATURE
<222> LOCATION: (30)..(30)
<223> OTHER INFORMATION: Xaa in position 30 is Lys, Ser, or is absent
<220> FEATURE:
<221> NAME/KEY: MISC_FEATURE
<222> LOCATION: (31)..(31)
<223> OTHER INFORMATION: Xaa in position 31 is Ser, Lys, or is absent
<220> FEATURE:
<221> NAME/KEY: MISC_FEATURE
<222> LOCATION: (32)..(32)
<223> OTHER INFORMATION: Xaa in position 32 is Gly, or is absent
<220> FEATURE:
<221> NAME/KEY: MISC_FEATURE
<222> LOCATION: (33)..(33)
<223> OTHER INFORMATION: Xaa in position 33 is Ala, or is absent
```

```
<220> FEATURE:
<221> NAME/KEY: MISC_FEATURE
<222> LOCATION: (34)..(34)
<223> OTHER INFORMATION: Xaa in position 34 is Pro, or is absent
<220> FEATURE:
<221> NAME/KEY: MISC_FEATURE
<222> LOCATION: (35)..(35)
<223> OTHER INFORMATION: Xaa in position 35 is Pro, or is absent
<220> FEATURE:
<221> NAME/KEY: MISC_FEATURE
<222> LOCATION: (36)..(36)
<223> OTHER INFORMATION: Xaa in position 36 is Pro, or is absent
<220> FEATURE:
<221> NAME/KEY: MISC_FEATURE
<222> LOCATION: (37)..(37)
<223> OTHER INFORMATION: Xaa in position 37 is Ser, or is absent

<400> SEQUENCE: 4

Xaa Xaa Thr Phe Thr Ser Asp Xaa Ser Xaa Xaa Xaa Glu Xaa Xaa Ala
1               5                   10                  15

Xaa Xaa Xaa Phe Ile Xaa Trp Leu Xaa Xaa Xaa Xaa Xaa Xaa Xaa Xaa
            20                  25                  30

Xaa Xaa Xaa Xaa Xaa
        35

<210> SEQ ID NO 5
<211> LENGTH: 38
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa in position 1 is Ala, Gly, Val, Leu, Ile or
      Lys
<220> FEATURE:
<221> NAME/KEY: MISC_FEATURE
<222> LOCATION: (2)..(2)
<223> OTHER INFORMATION: Xaa in position 2  is Glu or, Asp
<220> FEATURE:
<221> NAME/KEY: MISC_FEATURE
<222> LOCATION: (3)..(3)
<223> OTHER INFORMATION: Xaa in position 3 is Gly or Ala
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa in position 11 is Ser, Lys or Arg
<220> FEATURE:
<221> NAME/KEY: MISC_FEATURE
<222> LOCATION: (12)..(12)
<223> OTHER INFORMATION: Xaa in position 12 is Tyr or Gln
<220> FEATURE:
<221> NAME/KEY: MISC_FEATURE
<222> LOCATION: (13)..(13)
<223> OTHER INFORMATION: Xaa in position 13 is Leu or Met
<220> FEATURE:
<221> NAME/KEY: MISC_FEATURE
<222> LOCATION: (15)..(15)
<223> OTHER INFORMATION: Xaa in position 15 is Gly or Glu
<220> FEATURE:
<221> NAME/KEY: MISC_FEATURE
<222> LOCATION: (16)..(16)
<223> OTHER INFORMATION: Xaa in position 16 is Gln, Glu, Lys or Arg
<220> FEATURE:
<221> NAME/KEY: MISC_FEATURE
<222> LOCATION: (18)..(18)
<223> OTHER INFORMATION: Xaa in position 18 is Ala or Val
<220> FEATURE:
<221> NAME/KEY: MISC_FEATURE
<222> LOCATION: (19)..(19)
```

<223> OTHER INFORMATION: Xaa in position 19 is Lys, Glu or Arg
<220> FEATURE:
<221> NAME/KEY: MISC_FEATURE
<222> LOCATION: (20)..(20)
<223> OTHER INFORMATION: Xaa in position 20 is Glu or Leu
<220> FEATURE:
<221> NAME/KEY: MISC_FEATURE
<222> LOCATION: (23)..(23)
<223> OTHER INFORMATION: Xaa in position 23 is Ala, Glu or Arg
<220> FEATURE:
<221> NAME/KEY: MISC_FEATURE
<222> LOCATION: (26)..(26)
<223> OTHER INFORMATION: Xaa in position 26 is Val, Lys or Arg
<220> FEATURE:
<221> NAME/KEY: MISC_FEATURE
<222> LOCATION: (27)..(27)
<223> OTHER INFORMATION: Xaa in position 27 is Lys, Glu, Asn, His or Arg
<220> FEATURE:
<221> NAME/KEY: MISC_FEATURE
<222> LOCATION: (28)..(28)
<223> OTHER INFORMATION: Xaa in position 28 is Gly
<220> FEATURE:
<221> NAME/KEY: MISC_FEATURE
<222> LOCATION: (29)..(29)
<223> OTHER INFORMATION: Xaa in position 29 is Arg, Gly or Lys
<220> FEATURE:
<221> NAME/KEY: MISC_FEATURE
<222> LOCATION: (30)..(30)
<223> OTHER INFORMATION: Xaa in position 30 is Gly, Ala, Glu, Pro, Lys,
    or is absent
<220> FEATURE:
<221> NAME/KEY: MISC_FEATURE
<222> LOCATION: (31)..(31)
<223> OTHER INFORMATION: Xaa in position 31 is Lys, Ser, or is absent
<220> FEATURE:
<221> NAME/KEY: MISC_FEATURE
<222> LOCATION: (32)..(32)
<223> OTHER INFORMATION: Xaa in position 32 is Ser, Lys, or is absent
<220> FEATURE:
<221> NAME/KEY: MISC_FEATURE
<222> LOCATION: (33)..(33)
<223> OTHER INFORMATION: Xaa in position 33 is Gly, or is absent
<220> FEATURE:
<221> NAME/KEY: MISC_FEATURE
<222> LOCATION: (34)..(34)
<223> OTHER INFORMATION: Xaa in position 34 is Ala, or is absent
<220> FEATURE:
<221> NAME/KEY: MISC_FEATURE
<222> LOCATION: (35)..(35)
<223> OTHER INFORMATION: Xaa in position 35 is Pro, or is absent
<220> FEATURE:
<221> NAME/KEY: MISC_FEATURE
<222> LOCATION: (36)..(36)
<223> OTHER INFORMATION: Xaa in position 36 is Pro, or is absent
<220> FEATURE:
<221> NAME/KEY: MISC_FEATURE
<222> LOCATION: (37)..(37)
<223> OTHER INFORMATION: Xaa in position 37 is Pro, or is absent
<220> FEATURE:
<221> NAME/KEY: MISC_FEATURE
<222> LOCATION: (38)..(38)
<223> OTHER INFORMATION: Xaa in position 38 is Ser, or is absent

<400> SEQUENCE: 5

Xaa Xaa Xaa Thr Phe Thr Ser Asp Xaa Ser Xaa Xaa Xaa Glu Xaa Xaa
1               5                   10                  15

Ala Xaa Xaa Xaa Phe Ile Xaa Trp Leu Xaa Xaa Xaa Xaa Xaa Xaa
            20                  25                  30

Xaa Xaa Xaa Xaa Xaa Xaa
        35

<210> SEQ ID NO 6
<211> LENGTH: 81
<212> TYPE: DNA
<213> ORGANISM: Artificial Sequence -continued
<220> FEATURE:
<223> OTHER INFORMATION: Synthetic

<400> SEQUENCE: 6
acttttactt ctgatgtttc ttcttatttg gaaggtcaag ctgctaaaga atttattgct    60
tggttggtta gaggtagagg t    81

<210> SEQ ID NO 7
<211> LENGTH: 117
<212> TYPE: DNA
<213> ORGANISM: Artificial Sequence
<220> FEATURE:
<223> OTHER INFORMATION: Synthetic

<400> SEQUENCE: 7
gaagaagctg aaaaggctga aggtactttt acttctgatg tttcttctta tttggaagaa    60
caagctgcta gagaatttat tgcttggttg gttagaggta gaggtaaaga agctgaa      117

<210> SEQ ID NO 8
<211> LENGTH: 114
<212> TYPE: DNA
<213> ORGANISM: Artificial Sequence
<220> FEATURE:
<223> OTHER INFORMATION: Synthetic

<400> SEQUENCE: 8
gaagaagctg aaaaggctga aggtactttt acttctgatg tttcttctta tttggaagaa    60
caagctgcta gagaatttat tgcttggttg gttagaggta gaaagaagc tgaa          114

<210> SEQ ID NO 9
<211> LENGTH: 27
<212> TYPE: PRT
<213> ORGANISM: Artificial Sequence
<220> FEATURE:
<223> OTHER INFORMATION: Synthetic

<400> SEQUENCE: 9

Thr Phe Thr Ser Asp Val Ser Ser Tyr Leu Glu Gly Gln Ala Ala Lys
1               5                   10                  15

Glu Phe Ile Ala Trp Leu Val Arg Gly Arg Gly
            20                  25

<210> SEQ ID NO 10
<211> LENGTH: 39
<212> TYPE: PRT
<213> ORGANISM: Artificial Sequence
<220> FEATURE:
<223> OTHER INFORMATION: Synthetic

<400> SEQUENCE: 10

Glu Glu Ala Glu Lys Ala Glu Gly Thr Phe Thr Ser Asp Val Ser Ser
1               5                   10                  15

Tyr Leu Glu Glu Gln Ala Ala Arg Glu Phe Ile Ala Trp Leu Val Arg
            20                  25                  30

Gly Arg Gly Lys Glu Ala Glu
        35

<210> SEQ ID NO 11
<211> LENGTH: 38
<212> TYPE: PRT
<213> ORGANISM: Artificial Sequence
<220> FEATURE:
<223> OTHER INFORMATION: Synthetic

<400> SEQUENCE: 11

Glu Glu Ala Glu Lys Ala Glu Gly Thr Phe Thr Ser Asp Val Ser Ser
1               5                   10                  15

Tyr Leu Glu Glu Gln Ala Ala Arg Glu Phe Ile Ala Trp Leu Val Arg
            20                  25                  30

Gly Arg Lys Glu Ala Glu
        35

<210> SEQ ID NO 12
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (31)..(31)
<223> OTHER INFORMATION: Pro or Tyr

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa
            20                  25                  30

<210> SEQ ID NO 13
<211> LENGTH: 40
<212> TYPE: PRT
<213> ORGANISM: Heloderma sp.

<400> SEQUENCE: 13

His Ser Asp Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40

<210> SEQ ID NO 14
<211> LENGTH: 43
<212> TYPE: DNA
<213> ORGANISM: Artificial Sequence
<220> FEATURE:
<223> OTHER INFORMATION: Synthetic

<400> SEQUENCE: 14
aggggtatcc atggctaaga gagaaggtac cttcacctct gac         43

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
aatcttagtt tctagagcct gcg                               23

<210> SEQ ID NO 16
<211> LENGTH: 6
<212> TYPE: PRT
<213> ORGANISM: Artificial Sequence
<220> FEATURE:

<223> OTHER INFORMATION: Synthetic

<400> SEQUENCE: 16

Arg Ala Arg Tyr Lys Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Arg Asp Leu Gly Lys Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic

<400> SEQUENCE: 18

Arg Asp Leu Ala Lys Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Arg Ala Arg Ala Lys Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Arg Ala Leu Asp Lys Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

Arg Ala Leu Ala Lys Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic

```
<400> SEQUENCE: 22

Pro Arg Asp Leu Gly Lys Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Arg Pro Leu Gly Lys Arg
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Arg Asp Leu Gly Lys Arg Glu Ala
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Arg Asp Leu Gly Lys Arg Glu Ala Gln
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic

<400> SEQUENCE: 26

Arg Asp Leu Gly Lys Arg Glu Ala Glu Ala
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Arg Asp Leu Gly Lys Arg Glu Ala Leu Glu Lys Arg
1               5                   10
```

```
<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Arg Asp Leu Gly Arg Arg Glu Ala Leu Glu Lys Arg
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic

<400> SEQUENCE: 29

Arg Asp Leu Gly Glu Ala Leu Glu Lys Arg
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Arg Asp Leu Gly Lys Arg Glu Ala Glu Ala Gln
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic

<400> SEQUENCE: 31

Arg Asp Leu Gly Lys Arg Glu Ala Glu Ala Gln Lys Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic

<400> SEQUENCE: 32

Arg Asp Leu Gly Arg Arg Glu Ala Glu Ala Gln Lys Arg
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Arg Asp Leu Gly Glu Ala Glu Ala Gln Lys Arg
1               5                   10
```

```
<210> SEQ ID NO 34
<211> LENGTH: 10
<212> TYPE: PRT
<213> ORGANISM: Artificial Sequence
<220> FEATURE:
<223> OTHER INFORMATION: Synthetic

<400> SEQUENCE: 34

Glu Arg Leu Glu Arg Asp Leu Gly Lys Arg
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic

<400> SEQUENCE: 35

Lys Glu Arg Leu Glu Arg Asp Leu Gly Lys Arg
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Glu Arg Leu Glu Lys Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Lys Glu Arg Leu Glu Lys Arg
1               5

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Pro Glu Arg Leu Glu Arg Asp Leu Gly Lys Arg
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic
```

<400> SEQUENCE: 39

Pro Glu Arg Leu Glu Lys Arg
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Glu Ala Glu Ala Arg Asp Leu Gly Lys Arg
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic

<400> SEQUENCE: 41

Pro Glu Ala Glu Ala Arg Asp Leu Gly Lys Arg
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Glu Glu Ala Glu Lys Arg
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

Glu Glu Ala Glu Arg Asp Leu Gly Lys Arg
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic

<400> SEQUENCE: 44

Arg Asp Leu Gly Glu Glu Ala Glu Lys Arg
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthetic

```
<400> SEQUENCE: 45

Glu Glu Ala Glu Leu Ala Lys Arg
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Glu Glu Ala Glu Leu Gly Lys Arg
1               5
```